(12) United States Patent
Schibli et al.

(10) Patent No.: US 9,295,739 B2
(45) Date of Patent: Mar. 29, 2016

(54) FOLATE CONJUGATES OF ALBUMIN-BINDING ENTITIES

(75) Inventors: Roger Schibli, Baden (CH); Rudolf Moser, Schaffhausen (CH); Cristina Magdalena Muller, Nussbaumen (CH); Harriet Struthers, Basel (CH); Viola Groehn, Dachsen (CH); Simon Mensah Ametamey, Zurich (CH); Cindy Ramona Fischer, Zurich (CH)

(73) Assignee: MERCK & CIE, Schaffhausen (CH)

(*) Notice: Subject to any disclaimer, the term of this patent is extended or adjusted under 35 U.S.C. 154(b) by 0 days.

(21) Appl. No.: 14/238,954

(22) PCT Filed: Aug. 10, 2012

(86) PCT No.: PCT/EP2012/065702
§ 371 (c)(1),
(2), (4) Date: Apr. 11, 2014

(87) PCT Pub. No.: WO2013/024035
PCT Pub. Date: Feb. 21, 2013

(65) Prior Publication Data
US 2014/0234216 A1  Aug. 21, 2014

(30) Foreign Application Priority Data
Aug. 17, 2011  (EP) .................................... 11177732

(51) Int. Cl.
| | | |
|---|---|---|
| A61K 51/00 | (2006.01) | |
| A61K 49/00 | (2006.01) | |
| A61K 51/04 | (2006.01) | |
| A61K 47/48 | (2006.01) | |
| C07D 475/04 | (2006.01) | |
| G01N 33/569 | (2006.01) | |
| C07B 59/00 | (2006.01) | |

(52) U.S. Cl.
CPC ....... *A61K 51/0497* (2013.01); *A61K 47/48107* (2013.01); *A61K 51/0472* (2013.01); *A61K 51/0491* (2013.01); *C07D 475/04* (2013.01); *G01N 33/56966* (2013.01); *C07B 59/002* (2013.01)

(58) Field of Classification Search
CPC ....... A61K 49/00; A61K 51/00; C07D 475/04
See application file for complete search history.

(56) References Cited

U.S. PATENT DOCUMENTS

| | | | |
|---|---|---|---|
| 6,093,382 A | | 7/2000 | Wedeking et al. |
| 6,221,334 B1 * | | 4/2001 | Wedeking ............ A61K 49/085 424/1.11 |
| 7,186,397 B2 | | 3/2007 | Wedeking et al. |
| 7,399,460 B2 | | 7/2008 | Wedeking et al. |
| 2001/0004454 A1 | | 6/2001 | Wedeking et al. |
| 2007/0077197 A1 | | 4/2007 | Wedeking et al. |
| 2011/0092806 A1 | | 4/2011 | Port et al. |

FOREIGN PATENT DOCUMENTS

WO  2007042504 A2  4/2007

OTHER PUBLICATIONS

International Search Report for PCT/EP2012/065702 dated Oct. 16, 2012.

* cited by examiner

*Primary Examiner* — Michael G Hartley
*Assistant Examiner* — Jagadishwar Samala
(74) *Attorney, Agent, or Firm* — Millen White Zelano and Branigan, PC; Csaba Henter; Anthony Zelano

(57) ABSTRACT

The present invention is directed towards new trifunctional folate-conjugates comprising a folate, an albumin binder and a radionuclide-based therapeutic or diagnostic moiety as well as pharmaceutical compositions thereof, their method of production and their use in diagnostic and therapeutic medical applications, such as diagnostic nuclear imaging and radionuclide therapy.

40 Claims, 5 Drawing Sheets

(A)

(B)

(A)

(B)

FOLATE CONJUGATES OF ALBUMIN-BINDING ENTITIES

FIELD OF INVENTION

The present invention is directed towards new trifunctional folate-conjugates comprising a folate, an albumin binder and a radionuclide-based diagnostic or therapeutic moiety as well as pharmaceutical compositions thereof, their method of production and their use in diagnostic and therapeutic medical applications, such as diagnostic nuclear imaging and radionuclide therapy.

BACKGROUND

Cell-specific targeting for delivery of diagnostic or therapeutic agents is a widely researched field and has led to the development of noninvasive diagnostic and/or therapeutic medical applications. In particular in the field of nuclear medicine procedures and treatments, which employ radioisotopes characterized by emission of gamma-rays or beta or alpha particles or Auger electrons, selective localization of these radioactive compounds in targeted cells or tissues is required to achieve either high signal intensity and specificity for visualization (gamma- or positron radiation) of specific tissues, assessing a disease and/or monitoring effects of therapeutic treatments, or to achieve high radiation dose through particle radiation (beta- or alpha-radiation), for delivery of adequate doses of ionizing radiation to a specified diseased site, while preventing damage to healthy tissues.

The folate receptor (FR) is a high-affinity membrane-associated protein, which exhibits limited expression on healthy cells, but is frequently overexpressed on a wide variety of specific cell types, such as epithelial tumor cells (e.g. ovarian, endometrial, breast, colorectal, kidney, lung, nasopharyngeal) and activated (but not resting) macrophages, which are involved in inflammation and autoimmune diseases. This led to the use of folic acid and its derivatives as a targeting agent for the delivery of therapeutic and/or diagnostic agents to these specific cell populations to achieve a selective concentration of pharmaceutical and/or diagnostic agents in these specific cells relative to normal cells. Such folate-conjugates include folate radiopharmaceuticals (Leamon and Low, Drug Discov. Today 2001; 6:44-51; Ke et al., Adv Drug Deliv Rev 2004, 1143-1160, Müller and Schibli, J Nucl Med 2011; 52:1-4; Müller, Curr Pharm Design 2012; 18:1058-1083), folate-conjugates of chemotherapeutic agents (Leamon and Reddy, Adv. Drug Deliv. Rev. 2004; 56:1127-41; Leamon et al, Bioconjugate Chem. 2005; 16:803-11; Vlahov et al. Bioconjug Chem 2012; in press), proteins and protein toxins (Ward et al., J. Drug Target. 2000; 8:119-23; Leamon et al, J. Biol. Chem. 1993; 268:24847-54; Leamon and Low, J. Drug Target. 1994; 2:101-12), antisense oligonucleotides (Li et al, Pharm. Res. 1998; 15:1540-45; Zhao and Lee, Adv. Drug Deliv. Rev. 2004; 56:1193-204), liposomes (Lee and Low, Biochim. Biophys. Acta-Biomembr. 1995; 1233:134-44); Gabizon et al, Adv. Drug Deliv. Rev. 2004; 56:1177-92), hapten molecules (Paulos et al, Adv. Drug Deliv. Rev. 2004; 56:1205-17); MRI contrast agents (Konda et al, Magn. Reson. Mat. Phys. Biol. Med. 2001; 12:104-13) etc.

Known folate radiopharmaceuticals include for example conjugates with $^{125}$I-labeled histamine (U.S. Pat. No. 4,136,159), with small metal-chelates such as deferoxamine (U.S. Pat. No. 5,688,488), acyclic or cyclic polyaminocarboxylates (e.g. DTPA, DTPA-BMA, DOTA and DO3A; U.S. Pat. No. 6,221,334, Fani et al. Eur J Nucl Med Mol Imaging 2011; 38: 108-119; Müller et al. Nucl Med Biol 2011; 38: 715-723), bisaminothiol (U.S. Pat. No. 5,919,934), 6-hydrazinonicotinamido-hydrazido (Shuang Liu, Topics in Current Chemistry, vol 252 (2005), Springer Berlin/Heidelberg), and ethylenedicysteine (U.S. Pat. No. 7,067,111), and small peptides (U.S. Pat. No. 7,128,893).

However, there is still a need for alternative, highly selective radionuclide conjugates, which can be synthesized easily and which exhibit optimal target (i.e. tumor cell, activated macrophage, etc.) to non-target tissue ratios and are eliminated through the kidneys, for use as tumor imaging agents in highly selective and non-invasive procedures permitting early detection and treatment of tumor cells, activated macrophages (and other targeted cells exhibiting high FR expression, not yet identified).

Applicants have now found novel trifunctional folate-conjugates that are able to overcome the drawbacks of known conjugates and meet the current needs by showing several advantages, such as stable complex formation, improved biodistribution and increased target tissue uptake. These novel trifunctional folate-conjugates comprise a folate, an albumin binder and a radionuclide-based therapeutic moiety or diagnostic moiety, e.g. a moiety suitable for diagnostic imaging or radiotherapeutic applications.

SUMMARY OF THE INVENTION

The present invention is in a first aspect directed to new trifunctional folate-conjugates comprising a folate, an albumin binder and a radionuclide-based therapeutic or diagnostic moiety (hereinafter also called compounds of the invention).

In one specific embodiment, the new folate conjugates are compounds of formula I,

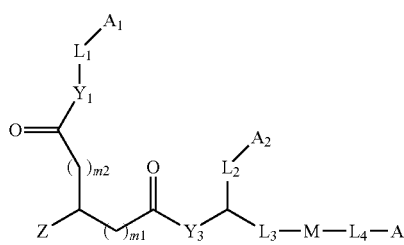

wherein
Z is a pteroate or derivative thereof,
$L_1, L_4$ are independently of each other a covalent bond or a straight-chain or branched C(1-8)alkyl, which is unsubstituted or substituted by at least one CN, Hal, OR', NHR', $CO_2R'$ or $NO_2$, wherein R' represents H or C(1-8)alkyl,
$L_2$ is a covalent bond or a linking group, such as straight-chain or branched C(1-8)alkyl, which is unsubstituted or substituted by at least one OR', NHR', or $CO_2R'$, and wherein one or more of the non-adjacent $CH_2$ groups may independently be replaced by a group selected from —O—, —CO—, —CO—O—, —O—CO—, —NR'—, —NR'—CO—, —CO—NR', wherein R' represents H or C(1-8)alkyl,
$L_3$ is a covalent bond or a linking group, such as straight-chain or branched C(1-8)alkyl, which is unsubstituted or substituted by at least one CN, Hal, OR', NHR', $CO_2R'$ or $NO_2$, and wherein one or more of the non-adjacent $CH_2$ groups may independently be replaced by a group selected from —O—, —CO—, —CO—O—, —O—CO—, —NR'—, —NR'—CO—, —CO—NR'—, —NR'—CO—O—, —O—CO—NR'—, —NR'—CO—NR'—, —CH═CH—, —C≡C—, —O—CO—O—, —S—R'—, —SO$_3$R'—, and a five-membered azaheterocycle, wherein R' represents H or C(1-8)alkyl, $Y_1, Y_3$ are independently of each other O, N or S, $A_1, A_2, A_3$ are independently of each other H, a capping group, or an albumin binder, M is a radionuclide-based therapeutic or diagnostic moiety, $m_1, m_2$ are independently of each other 0, 1, 2 or 3, with the proviso that at least one, preferably one, of $A_1, A_2$ and $A_3$ is an albumin binder.

Preferably, the invention is directed towards compounds of formula II

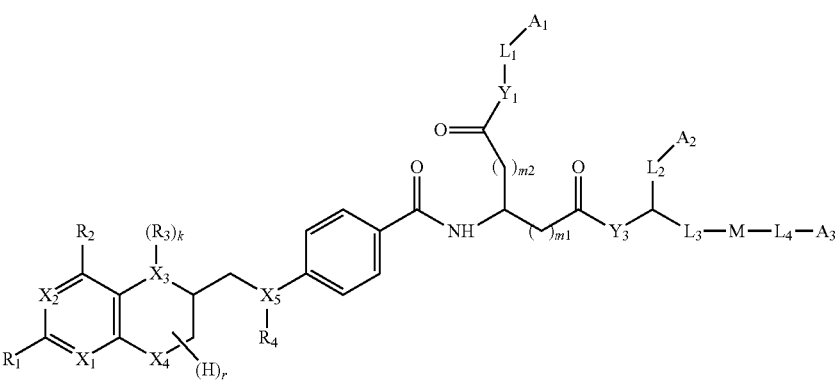

wherein $X_1$ to $X_5$ are independently of each other C, N or O, preferably N or O, $R_1, R_2$ are independently of each other H, halogen, C(1-12)alkyl, C(2-12)alkenyl, C(2-12)alkynyl, —OR$_5$, —COR$_5$, —COOR$_5$, NHR$_5$, —CONHR$_5$, —CONHR$_5$, wherein R$_5$ represents H, halo, C(1-12)alkyl, C(2-12)alkenyl, C(2-12)alkynyl, —OR', —COR', —COOR', or —NHR', wherein R' is H or C(1-8)alkyl, $R_3, R_4$ are independently of each other H, nitroso, C(1-12)alkyl, —OR', —COR' or halosubstituted —COR', wherein R' represents H or C(1-8)alkyl, and $L_1, L_2, L_3, L_4, Y_1, Y_3, A_1, A_2, A_3$, M, $m_1, m_2$, k, and r are as defined above.

The albumin binder is preferably a linear or branched lipophilic group having 12-40 carbon atoms and a distal acidic group, such as a compound of formula III

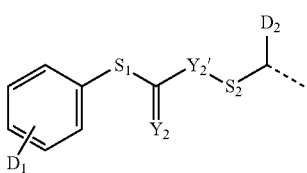

wherein $Y_2, Y_{2'}$ are independently of each other N, O or S, $S_1, S_2$ are independently of each other a single bond or a spacer selected from a straight-chain or branched C(1-12) alkyl, which is unsubstituted or substituted by at least one CN, Hal, OR', NHR', CO$_2$R', SH, SO$_3$H or NO$_2$, and wherein one or more of the non-adjacent CH$_2$ groups may independently be replaced by —O—, —CO—, —CO—O—, —O—CO—, —NR'—, —NR'—CO—, —CO—NR'—, —NR'—CO—O—, —O—CO—NR'—, —NR'—CO—NR'—, —CH═CH—, —C≡C—, —O—CO—O—, —S—R'—, —SO$_3$R'—, wherein R represents H or C(1-8)alkyl, $D_1$ is a group selected from H, halogen, C(1-12)alkyl, C(2-12)alkenyl, C(2-12)alkynyl, —OR$_5$, —COR$_5$, —COOR$_5$, —NHR$_5$, —CONHR$_5$, wherein R$_5$ represents H, C(1-12) alkyl, C(2-12)alkenyl, or C(2-12)alkynyl, $D_2$ is an acidic group, and the broken line represents the linkage to $L_1, L_2$ or $L_4$.

The acidic group is preferably a group capable of ionizing to donate a hydrogen ion to a base to form a salt, preferably selected from the group consisting of —COOH, —SO$_3$H, —SO$_2$H, —NR'SO$_3$H, —P(O)(OH)$_2$, wherein R' represents H or C(1-8)alkyl.

In specific embodiments, either $m_1$ is 2 and $m_2$ is 0 or else $m_1$ is 0 and $m_2$ is 2.

Preferably, M is a radionuclide-based therapeutic or diagnostic moiety $M_1$, which is a chelated metal radionuclide comprising a metal radionuclide and a metal chelator.

Alternatively, M is a radionuclide-based therapeutic or diagnostic moiety $M_2$, which is a gamma- or positron-emitting non-metal radionuclide, optionally in combination with a prosthetic group.

In specific embodiments, $L_3$ is a group $L_{3'}$, which is straight-chain or branched C(1-8)alkyl, which is unsubstituted or substituted by at least one Hal, OR', NHR', or CO$_2$R', and wherein one or more of the non-adjacent CH$_2$ groups may independently be replaced by a group selected from —O—, —CO—, —CO—O—, —NR'—, —NR'—CO—, or $L_3$ is a group of formulae (a), (b), or (c)

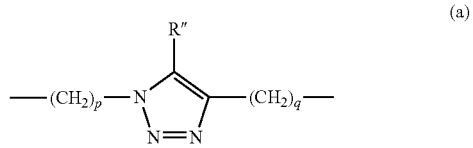

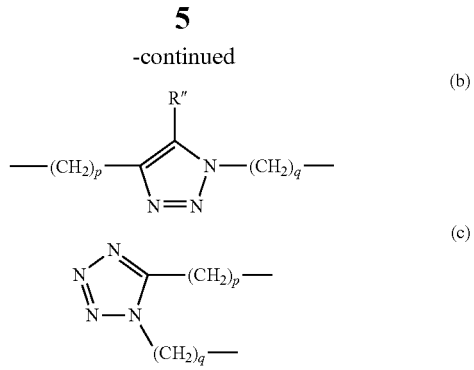

(b)

(c)

wherein

R" is H or a straight-chain or branched C(1-8)alkyl, which is unsubstituted or substituted by at least one CN, Hal, or $NO_2$, and p and q are independently of each other 0, 1, 2, 3, 4, 5 or 6.

In a further aspect the present invention provides methods for synthesizing the compounds of the invention.

In yet a further aspect the invention provides pharmaceutical compositions comprising a diagnostic imaging amount or a therapeutically effective amount of at least one compound of the present invention and a pharmaceutically acceptable carrier therefor.

In a further aspect the present invention provides uses of compounds and/or pharmaceutical compositions of the present invention for convenient and effective administration to a subject in need for diagnostic imaging or radionuclide therapy. The subject of the methods of the present invention is preferably a mammal, such as an animal or a human, preferably a human.

In a further aspect the present invention provides a single or multi-vial or multi-compartment kit containing all of the components needed to prepare the compounds of this invention.

Other features and advantages of the invention will be apparent from the following detailed description thereof and from the claims.

DETAILED DESCRIPTION OF THE INVENTION

Figure 1:
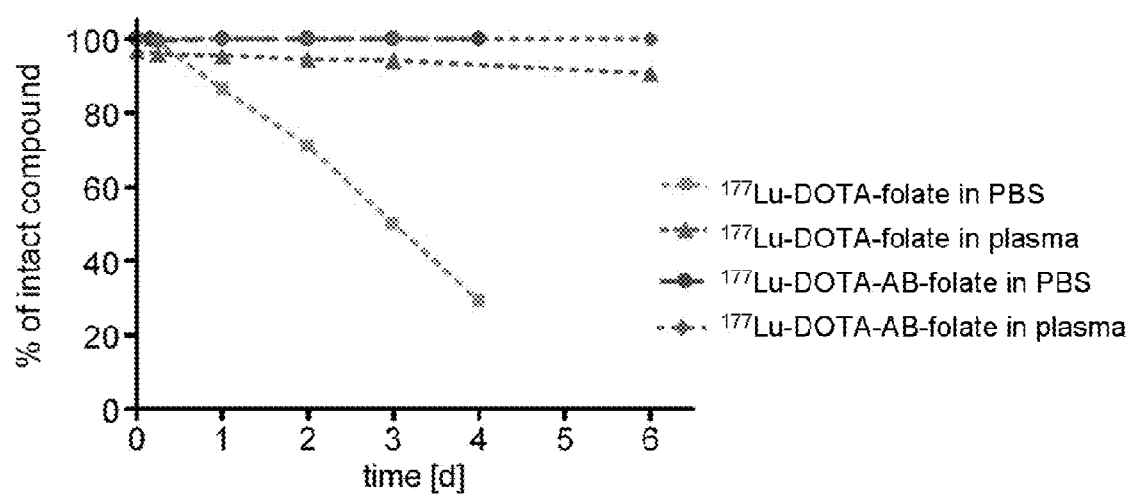
FIG. 1: In vitro stability of $^{177}$Lu-radiolabeled folate conjugates in PBS and human plasma (-■- represents $^{177}$Lu-DOTA-folate in PBS, -▲- represents $^{177}$Lu-DOTA-folate in plasma, -●- represents $^{177}$Lu-DOTA-AB-folate in PBS, -♦- represents $^{177}$Lu-DOTA-AB-folate in plasma).

The present invention is in a first aspect directed to new trifunctional folate-conjugates comprising a folate, an albumin binder and a radionuclide-based therapeutic or diagnostic moiety (hereinafter also called compounds of the invention).

The radionuclide-based therapeutic or diagnostic moiety (hereinafter also called "radionuclide moiety") may be comprising any known metal or non-metal radionuclide such as a radioactive metal ion, a paramagnetic metal ion, a gamma- or positron emitting radiohalogen, a positron-emitting radioactive non-metal, a hyperpolarised NMR-active nucleus, a reporter suitable for in vivo optical imaging, or a beta-emitter suitable for intravascular detection.

Preferred radionuclide moieties for diagnostic purpose are any known moieties for use in the present invention which can be detected externally in a non-invasive manner following administration in vivo. Most preferred radionuclide moieties are a chelated metal radionuclide (i.e. a radiometal) or a gamma- or positron-emitting non-metal radionuclide, i.e. particularly those suitable for detection using SPECT or PET. In some embodiments the folate, albumin binder and radionuclide moiety are in a radial arrangement, i.e. both the albumin binder and radionuclide moiety are attached to the amino acid portion of the folate molecule. In other embodiments, the folate, albumin binder and radionuclide moiety are in a linear arrangement, i.e. only one of the albumin binder and radionuclide moiety is attached to the amino acid portion of the folate molecule. A skilled person will know which arrangements are suitable, for example when $A_2$ is an albumin binder, M is preferably a chelated metal radionuclide (i.e. a radiometal).

Preferred radionuclide moieties for therapeutic purpose are any known moieties for use in the present invention, which can be used for the treatment of any disease responsive to radionuclide treatment, e.g. cancer, following administration in vivo. Most preferred radionuclide moieties are a chelated metal radionuclide (i.e. a radiometal) or a gamma- or positron-emitting non-metal radionuclide. In some embodiments the folate, albumin binder and radionuclide moiety are in a radial arrangement, i.e. both the albumin binder and radionuclide moiety are attached to the amino acid portion of the folate molecule. In other embodiments, the folate, albumin binder and radionuclide moiety are in a linear arrangement, i.e. only one of the albumin binder and radionuclide moiety is attached to the amino acid portion of the folate molecule. A skilled person will know which arrangements are suitable, e.g. when $A_2$ is an albumin binder, M is preferably a chelated metal radionuclide (i.e. a radiometal).

The present invention is specifically directed towards compounds of formula I,

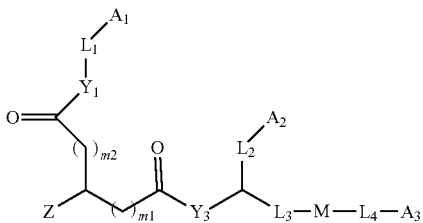

wherein

Z is a pteroate or derivative thereof, $L_1, L_4$ are independently of each other a covalent bond or a straight-chain or branched C(1-8)alkyl, which is unsubstituted or substituted by at least one CN, Hal, OR', NHR', $CO_2R'$ or $NO_2$, wherein R' represents H or C(1-8)alkyl, $L_2$ is a covalent bond or a linking group, such as straight-chain or branched C(1-8)alkyl, which is unsubstituted or substituted by at least one OR', NHR', or $CO_2R'$, and wherein one or more of the non-adjacent $CH_2$ groups may independently be replaced by a group selected from —O—, —CO—, —CO—O—, —O—CO—, —NR'—, —NR'—CO—, —CO—NR'—, wherein R' represents H or C(1-8) alkyl, $L_3$ is a covalent bond or a linking group, such as straight-chain or branched C(1-8)alkyl, which is unsubstituted or substituted by at least one CN, Hal, OR', NHR', $CO_2R'$ or $NO_2$, and wherein one or more of the non-adjacent $CH_2$ groups may independently be replaced by a group selected from —O—, —CO—, —CO—O—, —O—CO—, —NR'—, —NR'—CO—, —CO—NR'—, —NR'—CO—O—, —O—CO—NR'—, —NR'—CO—NR'—, —CH=CH—, —C≡C—, —O—CO—O—, —S—R'—, —$SO_3R'$—, and a five-membered azaheterocycle, wherein R' represents H or C(1-8)alkyl, $Y_1, Y_3$ are independently of each other O, N or S, $A_1, A_2, A_3$ are independently of each other H, a capping group, or an albumin binder, M is a radionuclide-based therapeutic or diagnostic moiety, preferably $M_1$ or $M_2$, wherein $M_1$ is a chelated metal radionuclide, and $M_2$ is a gamma- or positron-emitting non-metal radionuclide, optionally in combination with a prosthetic group, $m_1, m_2$ are independently of each other 0, 1, 2 or 3, with the proviso that at least one, preferably one, of $A_1, A_2$ and $A_3$ is an albumin binder.

Unless specified otherwise all the definitions given hereinafter apply throughout the text (including all structural formulas).

The term "pteroate" ("pteroyl" or "pteroic") refers to compounds based on a condensed pyrimidine heterocycle, which includes a pyrimidine fused with a further 5- or 6-membered heterocycle, such as for example a pteridine or a pyrrolopyrimidine bicycle Such a pteroate may then be linked to an aminobenzoyl moiety, which may then be further derivatized in the para-position with a linker of choice, such as a glutamic acid residue to give a folate. A folate is thus represented by a pteroyl-glutamic acid skeleton (more specifically N-[4(pteridin-6-ylmethylamino)benzoyl]-glutamic acid). Thus, as pteroate structures are precursors of folate structures, pteroate derivatives include the analogous derivatives as those typically known for folate structures, which are for example optionally substituted folic acid, folinic acid, pteropolyglutamic acid, and folate receptor-binding pteridines such as tetrahydropterins, dihydrofolates, tetrahydrofolates, and their deaza and dideaza analogs. The terms "deaza" and "dideaza" analogs refers to the art recognized analogs having a carbon atom substituted for one or two nitrogen atoms in the naturally occurring folic acid structure. For example, the deaza analogs include the 1-deaza, 3-deaza, 5-deaza, 8-deaza, and 10-deaza analogs. The dideaza analogs include, for example, 1,5-dideaza, 5,10-dideaza, 8,10-dideaza, and 5,8-dideaza analogs.

More specifically, the present invention is directed towards compounds of formula II

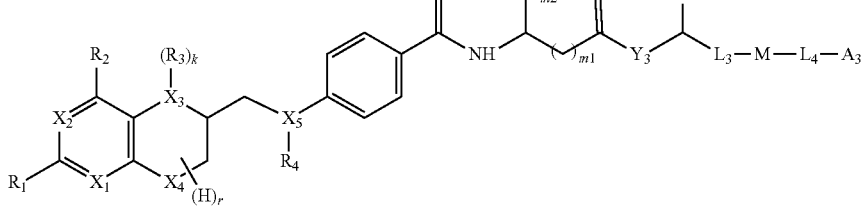

wherein $X_1$ to $X_5$ are independently of each other C, N or O, preferably N or O, $R_1, R_2$ are independently of each other H, halogen, C(1-12)alkyl, C(2-12)alkenyl, C(2-12)alkynyl, —$OR_5$, —$COR_5$, —$COOR_5$, —$NHR_5$, —$CONHR_5$, —$CONHR_5$, wherein $R_5$ represents H, halo, C(1-12)alkyl, C(2-12)alkenyl, C(2-12)alkynyl, —OR', —COR', —COOR', or —NHR', wherein R' is H or C(1-8)alkyl, $R_3, R_4$ are independently of each other H, nitroso, C(1-12)alkyl, —OR', —COR' or halosubstituted —COR', wherein R' represents H or C(1-8)alkyl, $L_1, L_4$ are independently of each other a covalent bond or a straight-chain or branched C(1-8)alkyl, which is unsubstituted or substituted by at least one CN, Hal, OR', NHR', $CO_2R'$ or $NO_2$, wherein R' represents H or C(1-8)alkyl, $L_2$ is a covalent bond or a linking group, such as straight-chain or branched C(1-8)alkyl, which is unsubstituted or substituted by at least one OR', NHR', or $CO_2R'$, and wherein one or more of the non-adjacent $CH_2$ groups may independently be replaced by a group selected from —O—, —CO—, —CO—O—, —O—CO—, —NR'—, —NR'—CO—, —CO—NR', wherein R' represents H or C(1-8)alkyl, $L_3$ is a covalent bond or a linking group, such as straight-chain or branched C(1-8)alkyl, which is unsubstituted or substituted by at least one CN, Hal, OR', NHR', $CO_2R'$ or $NO_2$, and wherein one or more of the non-adjacent $CH_2$ groups may independently be replaced by a group selected from —O—, —CO—, —CO—O—, —O—CO—, —NR'—, —NR'—CO—, —CO—NR'—, —NR'—CO—O—, —O—CO—NR'—, —NR'—CO—NR'—, —CH═CH—, —C≡C—, —O—CO—O—, —S—R'—, —$SO_3$R'—, and a five-membered azaheterocycle, wherein R' represents H or C(1-8)alkyl, $Y_1, Y_3$ are independently of each other O, N or S, $A_1, A_2, A_3$ are independently of each other H, a capping group, or an albumin binder, M is a radionuclide-based therapeutic or diagnostic moiety $M_1$ or $M_2$, wherein $M_1$ is a chelated metal radionuclide, and $M_2$ is a gamma- or positron-emitting non-metal radionuclide, optionally in combination with a prosthetic group, $m_1, m_2$ are independently of each other 0, 1, 2 or 3, k is 0 or 1, and r has a value of 1 to 7, with the proviso that at least one, preferably one, of $A_1, A_2$ and $A_3$ is an albumin binder.

It is understood, that the abbreviations "N" and "C" are representative for all possible degrees of saturation, i.e. N includes —NH— and —N═linkages and C includes —$CH_2$— and —CH═linkages.

It is further understood, that $(H)_r$ represents all hydrogen substituents on the indicated ring (i.e. on $X_3$, C6, C7 and $X_4$). For example r=7 for a fully saturated 5,8-dideaza analog ($X_3$=$X_4$=C) and r=1 for a fully unsaturated analog with $X_3$=$X_4$=N.

The term "alkyl", when used singly or in combination, refers to straight chain or branched alkyl groups containing the indicated number of carbon atoms. Thus, the term "C(1-12)alkyl" refers to a hydrocarbon radical whose carbon chain is straight-chain or branched and comprises 1 to 12 carbon atoms. Preferred alkyl groups include C(1-8)alkyl groups which refer to a hydrocarbon radical whose carbon chain is straight-chain or branched and comprises 1 to 8 carbon atoms, for example methyl, ethyl, propyl, isopropyl, butyl, sec-butyl, isobutyl, tertiary butyl, pentyl, isopentyl, neopentyl, hexyl, 2,3-dimethylbutane, neohexyl, heptyl, octyl. More preferred alkyl groups are C(1-6)alkyl groups containing one to six C-atoms, more preferably one to four carbon atoms. Optionally substituted alkylchains, such as designated by —(CHR)$_x$—, represent an alkyl chain having —$CH_2$— groups of the indicated value x, and wherein each of —$CH_2$— groups may independently of each other be substituted with the indicated group R. Thus, in case of multiple R-groups, the R groups may be the same or different.

The term "alkenyl", singly or in combination with other groups, refers to straight chain or branched alkyl groups as defined hereinabove having one or more carbon-carbon double bonds. Thus, the term "C(2-12)alkenyl" refers to a hydrocarbon radical whose carbon chain is straight-chain or branched and comprises 1 to 12 carbon atoms and one or more carbon-carbon double bonds. Preferred alkenyl groups include C(2-8)alkenyl groups, such as methylene, ethylene, propylene, isopropylene, butylene, t-butylene, sec-butylene, isobutylene, amylene, isoamylene, pentylene, isopentylene, hexylene and the like. The preferred alkenyl groups contain two to six, more preferably two to four carbon atoms.

The term "alkynyl" as used herein refers to a linear or branched alkyl groups as defined hereinabove having one or more carbon-carbon triple bonds. The preferred alkynyl groups contain two to six, more preferably two to four carbon atoms.

As indicated above, the definition for "alkyl" applies both when used singly and in combination with other groups. Thus, alkoxy groups (or —O-alkyl) refer to alkyl groups as defined above, substituted with an oxygen, such as methoxy, ethoxy, propoxy, isopropoxy, butoxy, tert-butoxy and the like. Alkanoyl groups as used herein include formyl and —CO-alkyl-groups, which refer to alkyl groups as defined above, terminally-substituted with a carbonyl such as acetyl, propanoyl, butanoyl, pentanoyl and the like. Alkylamino groups (or —NHR-alkyl or —N(R)$_2$-alkyl) refer to alkyl groups as defined above, substituted with nitrogen, including both monoalkylamino such as methylamino, ethylamino, propylamino, tert-butylamino, and the like, and dialkylamino such as dimethylamino, diethylamino, methylpropylamino, and the like.

The term "halogen" or "halo" as used herein refers to any Group 7 element and includes fluoro, chloro, bromo, iodo.

The term "halosubstituted" as used herein refers to alkyl groups which have halogen moieties in the place of at least one hydrogen.

In preferred embodiments, $R_1$ and $R_2$ may be independently of each other H, C(1-12)alkyl, —$OR_5$, —$NHR_5$, more preferably —$OR_5$, —$NHR_5$; and/or $R_3$ is H, C(1-12)alkyl, or —CO—C(1-8)alkyl; and/or $R_4$ is H, nitroso, —O—C(1-8)alkyl, or —CO—C(1-8)alkyl.

The term "albumin binder" as used herein refers to a group, which binds noncovalently to human serum albumin (typically with a binding affinity less than about 10 μM). Albumin binding properties can be measured by surface plasmon resonance as described in J. Biol. Chem. 277(38), 35035-35042, (2002). Typical albumin binders suitable for use in the compounds of the present invention include linear and branched lipophilic groups having 12-40 carbon atoms and a distal acidic group. Suitable albumin binders for use in the compounds of the present invention are selected from compounds of formula III

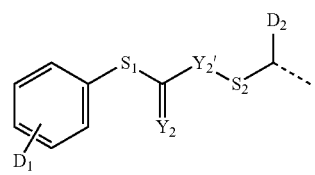

wherein $Y_2, Y_{2'}$ are independently of each other N, O or S, $S_1, S_2$ are independently of each other a single bond or a spacer selected from a straight-chain or branched C(1-12)alkyl, which is unsubstituted or substituted by at least one CN, Hal, OR', NHR', $CO_2R'$, SH, $SO_3H$ or $NO_2$, and wherein one or more of the non-adjacent $CH_2$ groups may independently be replaced by —O—, —CO—, —CO—O—, —O—CO—, —NR'—, —NR'—CO—, —CO—NR'—, —NR'—CO—O—, —O—CO—NR'—, —NR'—CO—NR'—, —CH═CH—, —C≡C—, —O—CO—O—, —S—R'—, —$SO_3$R'—, wherein R represents H or C(1-8)alkyl, D₁ is a group selected from H, halogen, C(1-12)alkyl, C(2-12)alkenyl, C(2-12)alkynyl, —OR₅, —COR₅, —COOR₅, —NHR₅, —CONHR₅, wherein R₅ represents H, C(1-12)alkyl, C(2-12)alkenyl, or C(2-12)alkynyl, D₂ is an acidic group, and the broken line represents the linkage to L₁, L₂ or L₄ (in the compounds of the invention).

Thus in specific embodiments the present invention contemplates compounds of formula IVa, IVb and IVc halo, C(1-12)alkyl, C(2-12)alkenyl, C(2-12)alkynyl, —OR', —COR', —COOR', or —NHR', wherein R' is H or C(1-8)alkyl, R₃, R₄ are independently of each other H, nitroso, C(1-12)alkyl, —OR', —COR' or halosubstituted —COR', wherein R' represents H or C(1-8)alkyl, A₁ is H or a capping group,
A₂ is H or a capping group,
A₃ is H or a capping group,

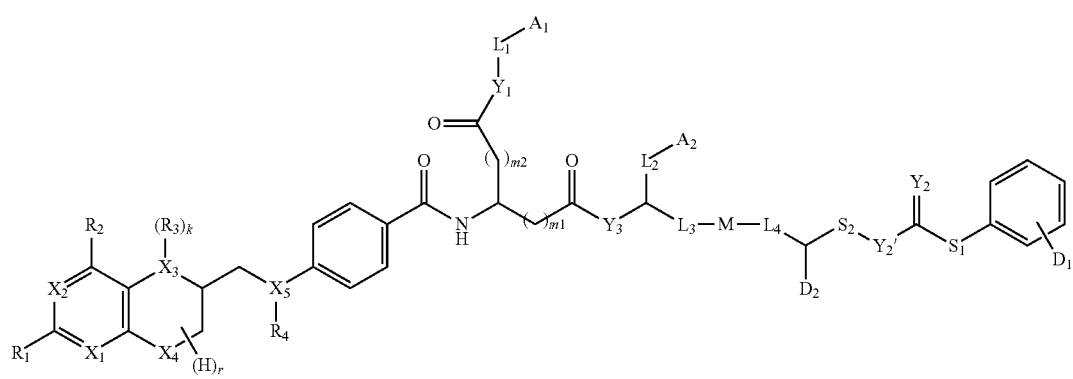

IVa

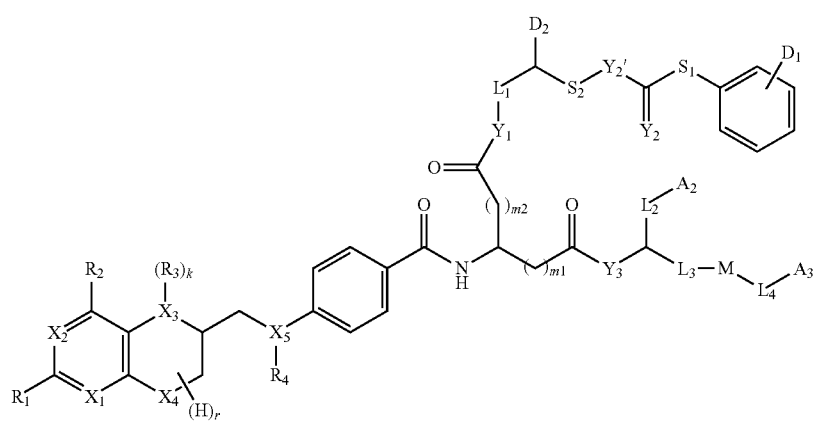

IVb

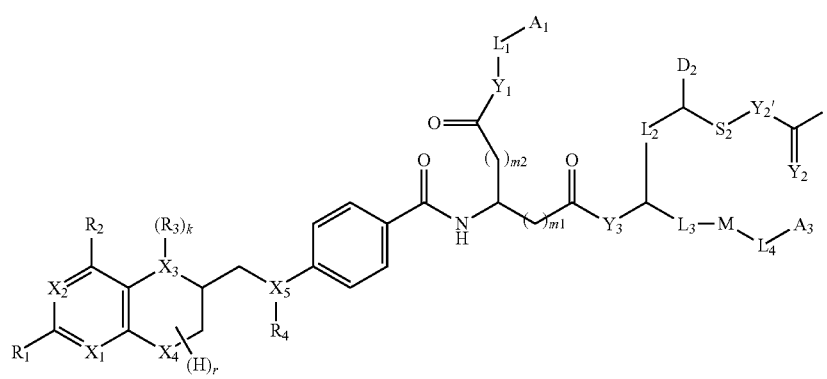

IVc wherein

X₁ to X₅ are independently of each other C, N or O, preferably N or O,

Y₁, Y₃ are independently of each other N, O or S,

Y₂, Y₂' are independently of each other N, O or S,

R₁, R₂ are independently of each other H, halogen, C(1-12)alkyl, C(2-12)alkenyl, C(2-12)alkynyl, —OR₅, —COR₅, —COOR₅, —NHR₅, CONHR₅, wherein R₅ represents H, M is radionuclide-based therapeutic or diagnostic moiety M₁ or M₂, wherein M₁ is a chelated metal radionuclide, and M₂ is a gamma- or positron-emitting non-metal radionuclide, optionally in combination with a prosthetic group, m is 1, 2 or 3, m₁, m₂ are independently of each other 0, 1, 2 or 3, L₁, L₄ are independently of each other a covalent bond or a straight-chain or branched C(1-8)alkyl, which is unsubstituted or substituted by at least one CN, Hal, OR', NHR', $CO_2R'$ or $NO_2$, wherein R' represents H or C(1-8)alkyl, $L_2$ is a covalent bond or a linking group, such as straight-chain or branched C(1-8)alkyl, which is unsubstituted or substituted by at least one OR', NHR', or $CO_2R'$, and wherein one or more of the non-adjacent $CH_2$ groups may independently be replaced by a group selected from —O—, —CO—, —CO—O—, —O—CO—, —NR'—, —NR'—CO—, —CO—NR', wherein R' represents H or C(1-8)alkyl, $L_3$ is a covalent bond or a linking group, such as straight-chain or branched C(1-8)alkyl, which is unsubstituted or substituted by at least one CN, Hal, OR', NHR', $CO_2R'$ or $NO_2$, and wherein one or more of the non-adjacent $CH_2$ groups may independently be replaced by a group selected from —O—, —CO—, —CO—O—, —O—CO—, —NR'—, —NR'—CO—, —CO—NR'—, —NR'—CO—O—, —O—CO—NR'—, —NR'—CO—NR'—, —CH=CH—, —C≡C—, —O—CO—O—, —S—R'—, —$SO_3R'$—, and a five-membered azaheterocycle, wherein R' represents H or C(1-8)alkyl, $S_1$, $S_2$ are independently of each other a single bond or a spacer selected from a straight-chain or branched C(1-12)alkyl, which is unsubstituted or substituted by at least one CN, Hal, OR', NHR', $CO_2R'$, SH, $SO_3H$ or $NO_2$, and wherein one or more of the non-adjacent $CH_2$ groups may independently be replaced by —O—, —CO—, —CO—O—, —O—CO—, —NR'—, —NR'—CO—, —CO—NR'—, —NR'—CO—O—, —O—CO—NR'—, —NR'—CO—NR'—, —CH=CH—, —C≡C—, —O—CO—O—, —S—R'—, —$SO_3R'$—, wherein R represents H or C(1-8)alkyl, $D_1$ is a group selected from H, halogen, C(1-12)alkyl, C(2-12)alkenyl, C(2-12)alkynyl, —$OR_5$, —$COR_5$, —$COOR_5$, —$NHR_5$, —$CONHR_5$, wherein $R_5$ represents H, C(1-12)alkyl, C(2-12)alkenyl, or C(2-12)alkynyl, $D_2$ is an acidic group, k is 0 or 1, and r has a value of 1 to 7.

Groups $L_1$ and $L_4$ are independently of each other preferably a covalent bond or a straight-chain or branched C(1-8)alkyl, which is unsubstituted or substituted by at least one CN, Hal, OR', NHR', $CO_2R'$ or $NO_2$, wherein R' represents H or C(1-8)alkyl, preferably a covalent bond or a straight-chain or branched unsubstituted C(1-6)alkyl, most preferably a covalent bond.

Group $L_2$ is preferably a covalent bond or a linking group, such as straight-chain or branched C(1-8)alkyl, wherein one or more of the non-adjacent $CH_2$ groups may independently be replaced by a group selected from —O—, —CO—, —CO—O—, —O—CO—, —NR'—, —NR'—CO—, —CO—NR', wherein R' represents H or C(1-8)alkyl, Preferably, $m_1$ and $m_2$ are not both 0. In specific embodiments $m_1$ is 2 and $m_2$ is 0, in other specific embodiments $m_1$ is 0 and $m_2$ is 2.

$Y_1$ is N, O, or S, preferably O; $Y_3$ is N, O, or S, preferably O; $Y_2$ is N, O, or S, preferably O; and $Y_{2'}$ is N, O, or S, preferably N.

The acidic group $D_2$ is a group capable of ionizing to donate a hydrogen ion to a base to form a salt, and is preferably selected from the group consisting of —COOH, —$SO_3H$, —$SO_2H$, —NR'$SO_3H$, —P(O)(OH)$_2$, wherein R' represents H or C(1-8)alkyl.

Group $D_1$ may be in ortho-, meta- or para-position, preferably in para-position. $D_1$ is preferably a group selected from H, halogen, or C(1-12)alkyl, more preferably halogen, more preferably iodine (most preferably iodine in para-position).

Preferably, $S_1$ and $S_2$ are independently of each other a single bond or a spacer selected from a straight-chain or branched C(1-8)alkyl, wherein one or more of the non-adjacent $CH_2$ groups may independently be replaced by —O—, —CO—, —COO—, —NR'—, —NR'—CO—, —CO—NR'—, —CH=CH—, wherein R' represents H or C(1-8)alkyl.

In specific embodiments $S_1$ and $S_2$ are independently of each other a single bond or a spacer selected from a straight-chain or branched C(1-6)alkyl.

Thus, in specific embodiments the albumin binder for use in compounds of the present invention is a group of formula IIIa

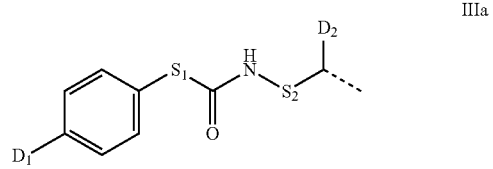

IIIa wherein $S_1$, $S_2$ are independently of each other a single bond or a spacer selected from a straight-chain or branched C(1-8)alkyl, wherein one or more of the non-adjacent $CH_2$ groups may independently be replaced by —O—, —CO—, —COO—, —NR'—, —NR'—CO—, —CO—NR'—, —CH=CH—wherein R' represents H or C(1-8)alkyl, preferably a single bond or a spacer selected from a straight-chain or branched C(1-6)alkyl, $D_1$ is a group selected from H, halogen, or C(1-12)alkyl, preferably halogen, more preferably iodine, $D_2$ is —COOH, —$SO_3H$, —$SO_2H$, —NR'$SO_3H$, preferably —COOH, and the broken line represents the linkage to $L_1$ or $L_2$ (in compounds of formulae I or II).

Thus, in preferred embodiments, compounds of formula IVa, IVb and IVc can be represented by compounds of formula Va, Vb and Vc

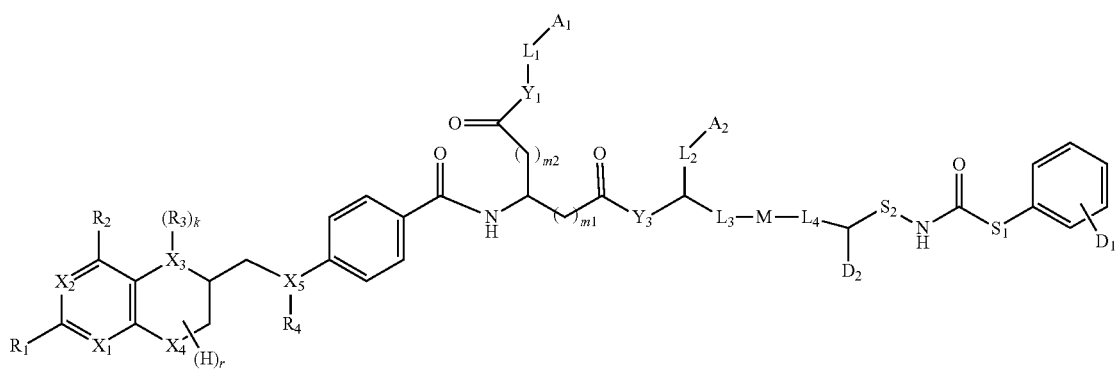

Va

-continued

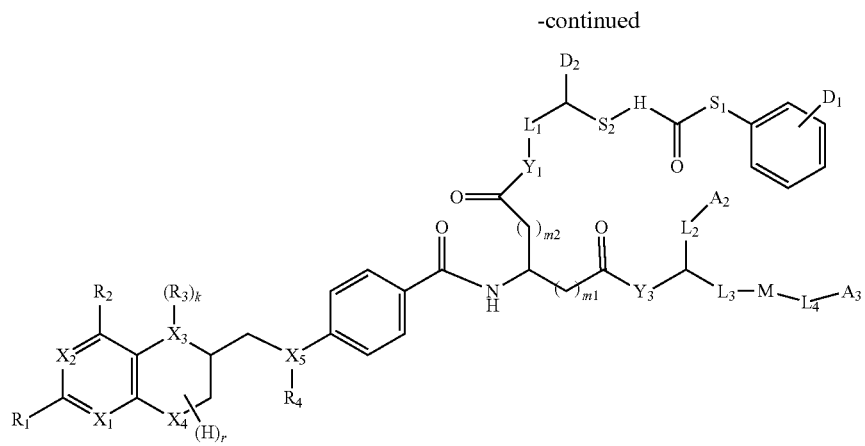

Vb

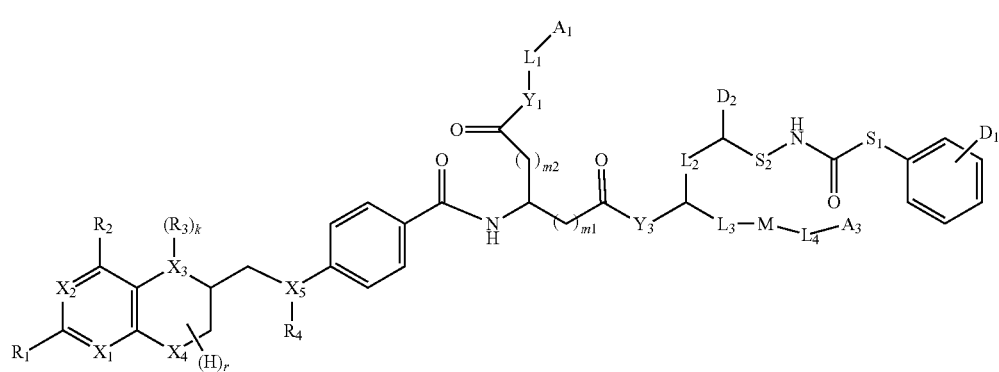

Vc wherein
$X_1$ to $X_5$ are independently of each other C, N or O, preferably N or O,
$Y_1, Y_3$ are independently of each other O, N or S,
$R_1, R_2$ are independently of each other H, halogen, C(1-12)alkyl, C(2-12)alkenyl, C(2-12)alkynyl, —$OR_5$, —$COR_5$, —$COOR_5$, —$NHR_5$, $CONHR_5$, wherein $R_5$ represents H, halo, C(1-12)alkyl, C(2-12)alkenyl, C(2-12)alkynyl, —OR', —COR', —COOR', or —NHR', wherein R' is H or C(1-8)alkyl,
$R_3, R_4$ are independently of each other H, nitroso, C(1-12)alkyl, —OR', —COR' or halosubstituted —COR', wherein R' represents H or C(1-8)alkyl,
$A_1$ is H or a capping group,
$A_2$ is H or a capping group,
$A_3$ is H or a capping group,
M is a radionuclide-based therapeutic or diagnostic moiety $M_1$ or $M_2$, wherein $M_1$ is a chelated metal radionuclide, and $M_2$ is a gamma- or positron-emitting non-metal radionuclide, optionally in combination with a prosthetic group,
m is 1, 2 or 3,
$m_1, m_2$ are independently of each other 0, 1, 2 or 3,
$L_1, L_4$ are independently of each other a covalent bond or a straight-chain or branched C(1-8)alkyl, which is unsubstituted or substituted by at least one CN, Hal, OR', NHR', $CO_2R'$ or $NO_2$, wherein R' represents H or C(1-8)alkyl,
$L_2$ is a covalent bond or a linking group, such as straight-chain or branched C(1-8)alkyl, which is unsubstituted or substituted by at least one OR', NHR', or $CO_2R'$, and wherein one or more of the non-adjacent $CH_2$ groups may independently be replaced by a group selected from —O—, —CO—, —CO—O—, —O—CO—, —NR'—, —NR'—CO—, —CO—NR', wherein R' represents H or C(1-8)alkyl, $L_3$ is a covalent bond or a linking group, such as straight-chain or branched C(1-8)alkyl, which is unsubstituted or substituted by at least one Hal, OR', NHR', or $CO_2R'$, and wherein one or more of the non-adjacent $CH_2$ groups may independently be replaced by a five-membered azaheterocycle selected from a triazolyl or tetrazolyl group wherein R' represents H or C(1-8)alkyl,
$S_1, S_2$ are independently of each other a single bond or a spacer selected from a straight-chain or branched C(1-8)alkyl, wherein one or more of the non-adjacent $CH_2$ groups may independently be replaced by —O—, —CO—, —COO—, —NR'—, —NR'—CO—, —CO—NR'—, —CH=CH—, wherein R' represents H or C(1-8)alkyl, preferably a single bond or a spacer selected from a straight-chain or branched C(1-6)alkyl,
$D_1$ is a group selected from H, halogen, or C(1-12)alkyl, preferably halogen, more preferably iodine
$D_2$ is —COOH, —$SO_3H$, —$SO_2H$, —$NR'SO_3H$, preferably —COOH, and the broken line represents the linkage to $L_1$ or $L_2$ (in compounds of formulae I or II),
k is 0 or 1, and
r has a value of 1 to 7.

In a specific embodiment, the imaging moiety M is a chelated radioimaging metal $M_1$ comprising a radioimaging metal ion and a metal chelator. The term "metal chelator" (or chelator) may be any of the metal chelators known in the art for complexing with a metal ion or radionuclide (and useful for the intended applications). The binding of a chelator to an ion/radionuclide may be determined by measuring the dissociation constant between chelator and ion/radionuclide. For the purposes of the present invention, the dissociation constant $K_D$ between chelator and ion/radionuclide is from about $10^{-3}$ to about $10^{-15}$ M$^{-1}$. Preferably, the dissociation constant $K_D$ between chelator and ion/radionuclide is from about $10^{-6}$ to about $10^{-15}$ M$^{-1}$.

Examples of chelators are well known in the art, and include bidentate, tridentate, and tetradentate ligands in linear, tripodal and macrocyclic form. Typical examples include bipyridyl (bipy); terpyridyl (terpy); crown ethers; aza-crown ethers; succinic acid; citric acid; salicylic acids; histidines; imidazoles; ethyleneglycol-bis-(beta-aminoethyl ether) N,N'-tetraacetic acid (EGTA); nitroloacetic acid; acetylacetonate (acac); sulfate; dithiocarbamates; carboxylates; alkyldiamines; ethylenediamine (en); diethylenetriamine (dien); nitrate; nitro; nitroso; $(C_6H_5)_2PCH_2CH_2P(C_6H_5)_2$ (diphos); glyme; diglyme; bis(acetylacetonate) ethylenediamine (acacen); ethylenediaminotetraacetic acid (EDTA), diethylenetriaminopentaacetic acid (DTPA); N-[2-[bis(carboxymethyl)amino]-3-(4-ethoxyphenyl)propyl]-N-[2-[bis(carboxymethyl)-amino]ethyl]-L-glycine (EOB-DTPA); N,N-bis[2-[bis(carboxymethyl)amino]-ethyl]-L-glutamic acid (DTPA-Glu); N,N-bis[2-[bis(carboxymethyl)amino]-ethyl]-L-lysine (DTPA-Lys); mono- or bis-amide derivatives of DTPA such as N,N-bis[2-[carboxymethyl[(methylcarbamoyl)methyl]amino]-ethyl]glycine (DTPA-BMA); 4-carboxy-5,8,11-tris(carboxymethyl)-1-phenyl-2-oxa-5,8,11-triazamidecan-13-oic acid (BOPTA); DTPA BOPTA, 1,4,7,10-tetraazacyclododecan-1,4,7-triactetic acid (DO3A); 1,4,7,10-tetraazacyclododecan-1,4,7,10-tetraactetic acid (DOTA); 10-(2-hydroxypropyl)-1,4,7,10-tetraazacyclododecan-1,4,7-triacetic acid (HPDO3A); 2-methyl-1,4,7,10-tetraazacyclododecan-1,4,7,10-tetraacetic acid (MCTA); tetramethyl-1,4,7,10-tetraazacyclododecan-1,4,7,10-tetraacetic acid (DOTMA); 3,6,9,15-tetraazabicyclo[9.3.1]pentadeca-1(15);11,13-triene-3,6,9-triacetic acid (PCTA); PCTA12; cyclo-PCTA12; N,N'-Bis(2-aminoethyl)-1,2-ethanediamine (TETA); 1,4,7,10-tetraazacyclotridecane-N,N',N'',N'''-tetraacetic acid (TRITA); 1,12-dicarbonyl, 15-(4-isothiocyanatobenzyl) 1,4,7,10,13-pentaazacyclohexadecane-N,N',N'' triacetic acid (HETA); 1,4,7,10-tetraazacyclododecane-N,N',N'',N'''-tetraacetic acid mono-(N-hydroxysuccinimidyl) ester (DOTA-NHS); N,N'-Bis(2-aminoethyl)-1,2-ethanediamine-N-hydroxy-succinimide ester (TETA-NHS); [(2S,5S,8S,11S)-4,7,10-tris-carboxymethyl-2,5,8,11-tetramethyl-1,4,7,10-tetraazacyclododecan-1-yl]acetic acid (M4DOTA); [(2S,5S,8S,11S)-4,7-bis-carboxymethyl-2,5,8,11-tetramethyl-1;4,7,10-tetraazacyclo-dodecan-1-yl]acetic acid; (M4DO3A); (R)-2-[(2S,5S,8S,11S)-4,7,10-tris-((R)-1-carboxyethyl)-2,5,8,11-tetramethyl-1,4,7,10-tetraazacyclododecan-1-yl]propionic acid (M4DOTMA); 10-phosphonomethyl-1,4,7,10-tetraazacyclododecane-1,4,7-triacetic acid (MPDO3A); hydroxybenzyl-ethylenediamine-diacetic acid (HBED) and N,N'-ethylenebis-[2-(o-hydroxyphenolic)glycine] (EHPG).

Suitable metal chelators for use in the compounds of the present invention include bidentate, tridentate, and tetradentate, ligands in linear, tripodal and macrocyclic form, as identified hereinabove. In specific embodiments, the metal chelators used for the present invention include linear or macrocyclic polyaminocarboxylates, such as DTPA, DOTA, DO3A, HP-DO3A, EDTA, TETA, EHPG, HBED, NOTA, DOTMA, TETMA, PDTA, TTHA, LICAM, MECAM, preferably macrocyclic polyaminocarboxylates, such as DTPA, DOTA, DO3A, HP-DO3A, EDTA, TETA, NOTA, DOTMA.

The metal chelator may or may not be complexed with a radio imaging metal ion or radionuclide, and may include an optional spacer such as a single amino acid. Typical metal radionuclides for scintigraphy or radionuclide therapy include $^{99}$Tc, $^{51}$Cr, $^{67}$Ga, $^{68}$Ga, $^{47}$Sc, $^{51}$Cr, $^{167}$Tm, $^{141}$Ce, $^{111}$In, $^{168}$Yb, $^{175}$Yb, $^{140}$La, $^{90}$Y, $^{88}$Y, $^{153}$Sm, $^{166}$Ho, $^{165}$Dy, $^{166}$Dy, $^{62}$Cu, $^{64}$Cu, $^{67}$Cu, $^{97}$Ru, $^{103}$Ru, $^{186}$Re, $^{188}$Re, $^{203}$Pb, $^{211}$Bi, $^{212}$Bi, $^{213}$Bi, $^{214}$Bi, $^{105}$Rh, $^{109}$Pd, $^{117}$mSn, $^{149}$Pm, $^{161}$Tb, $^{155}$Tb, $^{152}$Tb, $^{149}$Tb, $^{177}$Lu, $^{198}$Au and $^{199}$Au. The choice of metal will be determined based on the desired therapeutic or diagnostic application. For example, for diagnostic purposes radionuclides may include $^{64}$Cu, $^{67}$Ga, $^{68}$Ga, $^{99m}$Tc, and $^{111}$In, while for therapeutic purposes, radionuclides may include $^{64}$Cu, $^{90}$Y, $^{105}$Rh $^{111}$In, $^{117}$mSn, $^{149}$Pm, $^{153}$Sm, $^{161}$Tb, $^{166}$Dy, $^{166}$Ho, $^{175}$Yb, $^{177}$Lu, $^{186/188}$Re, and $^{199}$Au. A skilled person will know which radionuclide to choose for the intended application. Preferred radionuclides include $^{177}$Lu, $^{161}$Tb, $^{213}$Bi, $^{111}$In.

In another specific embodiment, the imaging moiety M is a gamma- or positron-emitting radioimaging non-metal $M_2$ selected from $^{11}$C, $^{13}$N, $^{15}$O, $^{17}$F, $^{18}$F, $^{75}$Br, $^{76}$Br, $^{77}$Br, $^{123}$I, $^{124}$I, $^{131}$I. Preferred are positron-emitting radioimaging non-metal such as $^{11}$C, $^{13}$N, $^{18}$F. more preferably $^{18}$F. A radioimaging non-metal of choice may be in combination with a prosthetic group, i.e. it may be linked directly or via a suitable prosthetic group, such as for example a benzoate derivative or a saccharide group, to its neighbouring group (i.e. groups $L_3$ and/or $L_4$).

The term "saccharide group" encompasses both cyclic monosaccharides and cyclic oligosaccharides based on cyclic saccharide unit(s). The term "saccharide unit" as used herein refers to cyclic saccharide units which refer to intracellular cyclic hemiacetal or hemiketal forms of a linear (mono-/oligo-) saccharide. A monosaccharide comprises one saccharide unit, whereas an oligosaccharide refers to a chain of saccharide units and comprises preferably 2 to 20 saccharide units, preferably 2 to 10 saccharide units, more preferably mono-, di-, and trisaccharides. An oligosaccharide may be linear or branched and the saccharide units within the oligosaccharide are linked to each other by alpha- or beta (1-2), (1-4), or (1-6) linkages. Preferably the oligosaccharide of choice is linear, and more preferably the oligosaccharide is linear and the saccharide units within the oligosaccharide are linked by alpha- or beta (1-4) bonds. In the most preferred embodiment, the oligosaccharide is linear and the saccharide units within the oligosaccharide are linked by alpha (1-4) bonds.

Preferably a saccharide unit is a pyranoside or a furanoside and natural and synthetic derivatives thereof, preferably a pyranoside selected from allose, altrose, glucose, mannose, gulose, idose, galactose, talose and fucose, or a furanoside selected from ribose, arabinose, xylose, and lyxose. The term derivative refers to any chemically or enzymatically modified monosaccharide unit, including those obtained by oxidation, deoxygenation, replacement of one or more hydroxyl groups by preferably a hydrogen atom, a halogen atom, an amino group or thiol group, etc., as well as alkylation, acylation, sulfation or phosphorylation of hydroxy groups or amino groups. Preferred saccharide units of the present invention include for example glucose and galactose.

Thus in one specific embodiment, the saccharide group is a monosaccharide selected from ribose, arabinose, xylose, lyxose, allose, altrose, glucose, mannose, gulose, idose, galactose, talose, fucose, preferably glucose and galactose.

In another specific embodiment, the saccharide group is an oligosaccharide comprising at least two, preferably 2 to 20 saccharide units which are identical or different and each selected from the group consisting of ribose, arabinose, xylose, lyxose, allose, altrose, glucose, mannose, gulose, idose, galactose, talose, fucose, preferably glucose and galactose.

In more specific embodiments an oligosaccharide may be (a) a disaccharide, e.g. lactose, maltose, isomaltose, cellobiose, gentiobiose, melibiose, primeverose, rutinose; (b) a disaccharide homologue, e.g. maltotriose, isomaltotriose, maltotetraose, isomaltotetraose, maltopentaose, maltohexaose, maltoheptaose, lactotriose, lactotetraose; (c) a uronic acid, e.g. glucuronic acid, galacturonic acid; (d) a branched oligosaccharide, e.g. panose, isopanose; (e) an amino monosaccharide, e.g. galactosamine, glucosamine, mannosamine, fucosamine, quinovosamine, neuraminic acid, muramic acid, lactosediamine, acosamine, bacillosamine, daunosamine, desosamine, forosamine, garosamine, kanosamine, kansosamine, mycaminose, mycosamine, perosamine, pneumosamine, purpurosamine, rhodosamine; (f) a modified saccharide, e.g. abequose, amicetose, arcanose, ascarylose, boivinose, chacotriose, chalcose, cladinose, colitose, cymarose, 2-deoxyribose, 2-deoxyglucose, diginose, digitalose, digitoxose, evalose, evernitrose, hamamelose, manninotriose, melibiose, mycarose, mycinose, nigerose, noviose, oleandrose, paratose, rhodinose, rutinose, sarmentose, sedoheptulose, solatriose, sophorose, streptose, turanose, tyvelose.

In a more preferred embodiment, the saccharide group is a monosaccharide or an oligosaccharide, thus comprising one or more of the (same or different) saccharide unit(s) which is (are) selected from the group consisting of glucose, galactose, glucosamine, galactosamine, glucuronic acid, gluconic acid, galacturonic acid, lactose, lactotetraose, maltose, maltotriose, maltotetraose, isomaltose, isomaltotriose, isomaltotetraose, and neuraminic acid.

It is understood that all isomers, including enantiomers, diastereoisomers, rotamers, tautomers and racemates of the compounds of the invention are contemplated as being part of this invention. The invention includes stereoisomers in optically pure form and in admixture, including racemic mixtures. Isomers can be prepared using conventional techniques, either by reacting optically pure or optically enriched starting materials or by separating isomers of a compound of formula I. This applies specifically to saccharide groups, or any other groups, e.g. amino acid groups present in a compound of formula I (and subsequent formulas), which may be present in the natural L- or non-natural D-form, i.e. the glutamic acid portion (or derivatives thereof).

The term "capping group" (or terminal groups) as used herein refers to a moiety attached to the functional groups $L_1$, $L_2$ or $L_4$, which is otherwise H or linked to an albumin binder. More specifically such capping groups represent suitable protecting groups for (i) $Y_1$ if $L_1$ represents a covalent bond, (ii) M if $L_4$ represents a covalent bond, and (iii) $L_2$ if $L_2$ is a functional group or carries a terminal functional group. These protecting groups depend on the nature of the functional group (typically an amino, carboxyl or hydroxy function) and thus are variable. Suitable protecting groups for amino functions include e.g. the t-butoxycarbonyl, the benzyloxycarbonyl, allyloxycarbonyl, methoxy- or ethoxycarbonyl, 2,2,2-trichloroethoxycarbonyl, acetyl or trifluoroacetyl, benzyl or 2,4,6-trimethoxybenzyl, the phthaloyl group, and the trityl or tosyl protecting group. Suitable protecting groups for the carboxyl function include e.g. silyl groups and alkyl, aryl or arylalkyl esters, more specifically alkyl esters such as methyl and t-butyl; alkoxyalkyl such as methoxymethyl; alkyl thioalkyl esters such as methyl, thiomethyl; haloalkyl esters such as 2,2,2-trichloroethyl and aralkyl ester, such as benzyl, p-methoxybenzyl, p-nitrobenzyl, diphenylmethyl. Suitable protecting groups for the hydroxy function include e.g. alkyl esters, t-butyl, benzyl or trityl groups, including methyl ethers, substituted methyl ethers (e.g., MOM (methoxymethyl ether), MTM (methylthiomethyl ether), BOM (benzyloxymethyl ether), PMBM or MPM (p-methoxybenzyloxymethyl ether)), substituted ethyl ethers, substituted benzyl ethers, silyl ethers (e.g., TMS (trimethylsilyl ether), TES (triethylsilyl ether), TIPS (triisopropylsilyl ether), TBDMS (tert-butyldimethylsilyl ether), tribenzyl silyl ether, TBDPS (tert-butyldiphenylsilyl ether)). The present invention is not intended to be limited to these protecting groups; rather, a variety of additional equivalent protecting groups can be readily identified and utilized in the present invention. The above and further protecting groups as well as techniques to introduce and remove them are described in "Protective Groups in Organic Synthesis" Third Ed. Greene, T. W. and Wuts, P. G., Eds., John Wiley & Sons, New York: 1999, the entire contents of which are hereby incorporated by reference.

In specific embodiments $Y_1$ is O and $L_1$ is a covalent bond, and thus $A_1$ may be H or a carboxyl protecting group. Likewise, if M is a polyaminocarboxylate and $L_4$ is a covalent bond, then $A_3$ may be H or a carboxyl protecting group. If $L_2$ is a carboxyl group (i.e. a C1-alkyl, wherein the $CH_2$ group was replaced by —COO—), then $A_2$ may be H or a carboxyl protecting group. Likewise if M is a gamma- or positron-emitting non-metal radionuclide in combination with a prosthetic group such as a saccharide group, then $A_3$ may be a hydroxyl protecting group.

Group $L_3$ is preferably is a covalent bond or a linking group, such as straight-chain or branched C(1-8)alkyl, which is unsubstituted or substituted by at least one Hal, OR', NHR', or COOR', and wherein one or more of the non-adjacent $CH_2$ groups may independently be replaced by a group selected from —O—, —CO—, —CO—O—, —O—CO—, —NR'—, —NR'—CO—, —CO—NR'—, —CH=CH—, and a five-membered azaheterocycle, wherein R' represents H or C(1-8)alkyl.

More preferably, group $L_3$ is straight-chain or branched C(1-8)alkyl, which is unsubstituted or substituted by at least one Hal, OR', NHR', or $CO_2R'$, and wherein one or more of the non-adjacent $CH_2$ groups may independently be replaced by a five-membered azaheterocycle selected from a triazolyl or tetrazolyl group wherein R' represents H or C(1-8)alkyl.

The term "azaheterocycle" refers to a heterocyclic group, which includes at least one nitrogen atom in a ring and may be unsubstituted or substituted. The azaheterocyclic group may also be substituted as recognized in the art, e.g. by a C(1-6) alkyl.

For use in the present compound, the five-membered azaheterocyclic group is preferably a triazolyl or tetrazolyl group, more preferably a group of the following structures

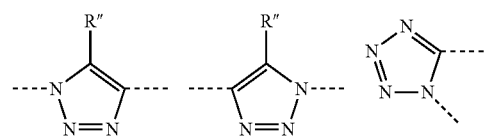

wherein the dotted lines represent linking sites to the adjacent —$CH_2$— groups within $L_3$ and R" is H or a straight-chain or branched C(1-8)alkyl, which is unsubstituted or substituted by at least one CN, Hal, or $NO_2$.

Thus in preferred embodiments $L_3$ is a group $L_{3'}$, which is straight-chain or branched C(1-8)alkyl, which is unsubstituted or substituted by at least one Hal, OR', NHR', or $CO_2R'$, and wherein one or more of the non-adjacent $CH_2$ groups may independently be replaced by a group selected from —O—, —CO—, —CO—O—, —NR'—, —NR'—CO—, or $L_3$ is a group of formulae (a), (b), or (c)

(a)

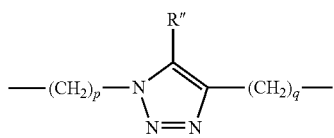

(c)

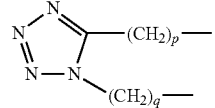

wherein

R″ is H or a straight-chain or branched C(1-8)alkyl, which is unsubstituted or substituted by at least one CN, Hal, or NO$_2$, and p, q are independently of each other 0, 1, 2, 3, 4, 5 or 6.

In preferred embodiments, L$_3$, is straight-chain or branched C(1-6)alkyl, which is unsubstituted or substituted by at least one OH, NH$_2$, or COOH, preferably COOH, and wherein one or more of the non-adjacent CH$_2$ groups may independently be replaced by a group selected from —CO—O— or —CO—NH—.

In some embodiments the present invention provides compounds of formula I having formulae VI a-e VIa

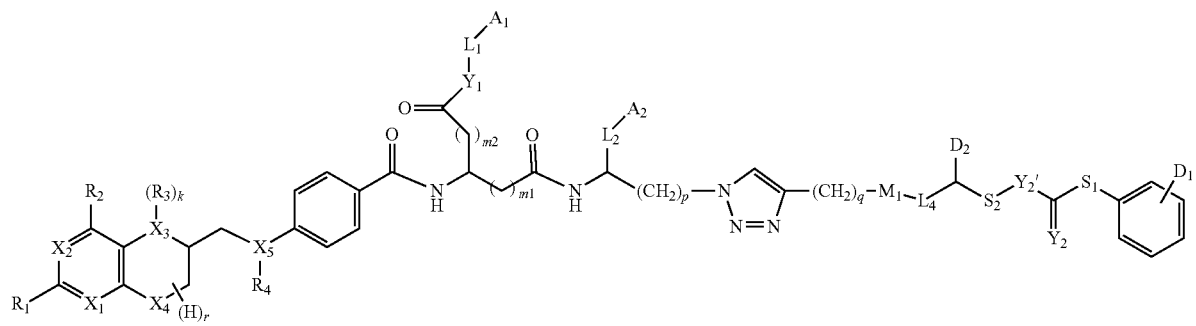

VIb

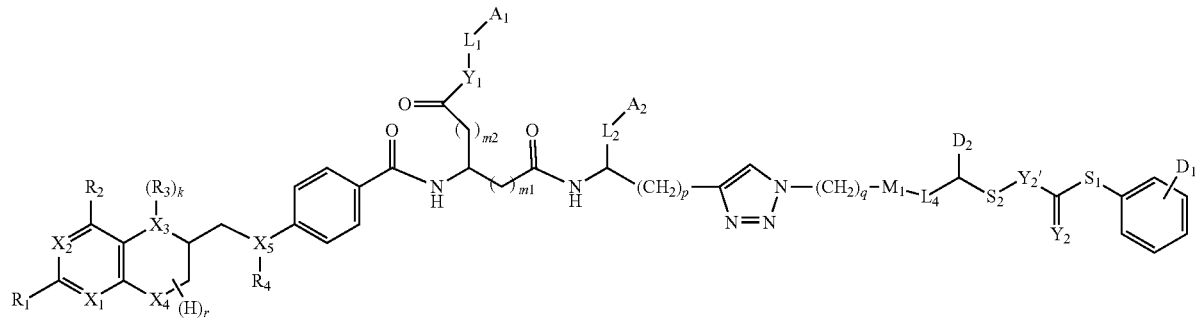

VIc

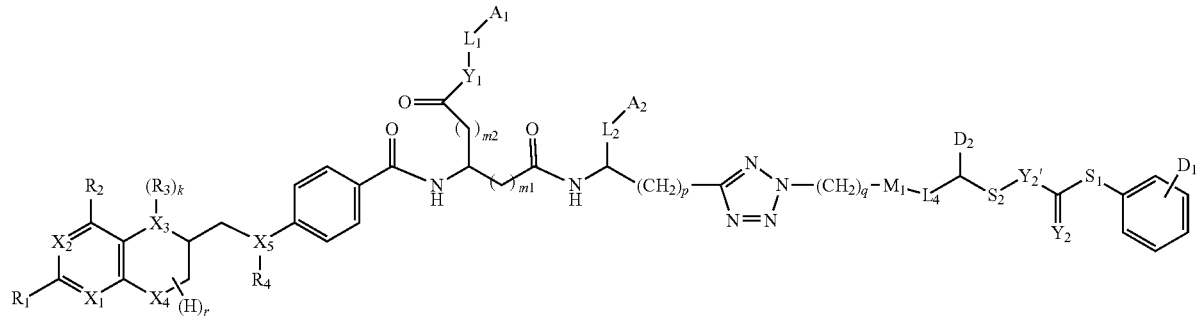

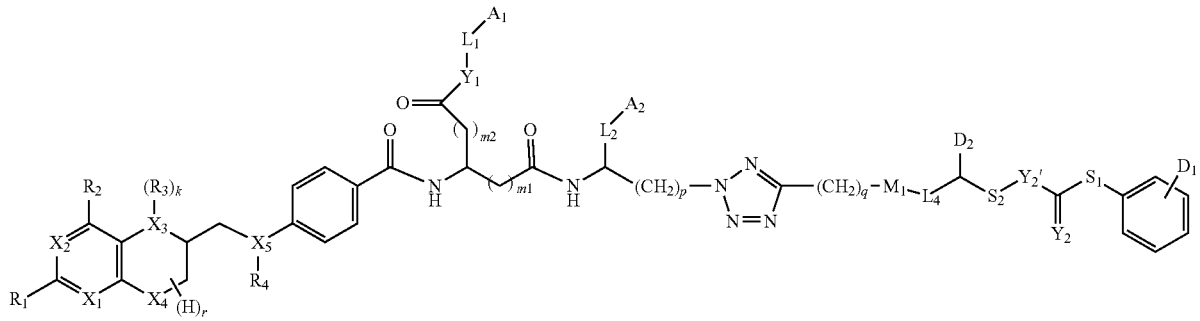

VId

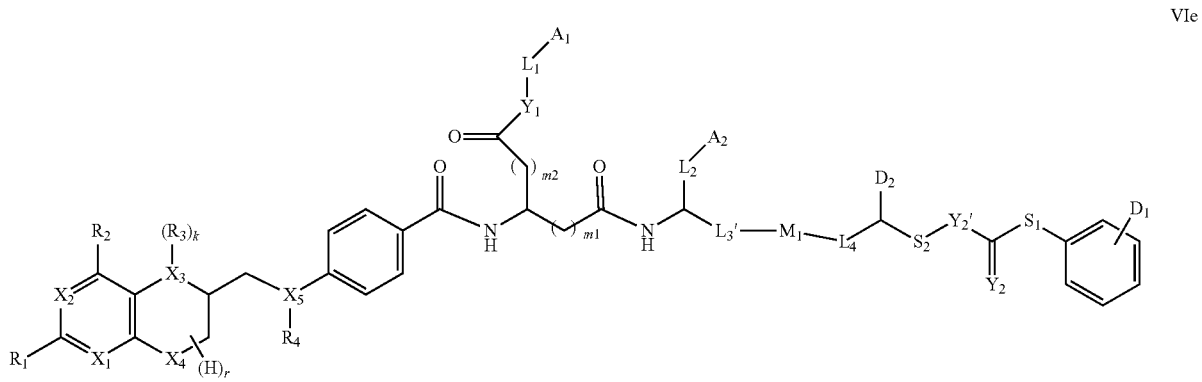

VIe wherein $X_1$ to $X_5$ are independently of each other C, N or O, preferably N or O, $Y_1, Y_2, Y_{2'}$ are independently of each other N, O or S, $R_1, R_2$ are independently of each other H, halogen, C(1-12)alkyl, C(2-12)alkenyl, C(2-12)alkynyl, —$OR_5$, —$COR_5$, —$COOR_5$, —$NHR_5$, $CONHR_5$, wherein $R_5$ represents H, halo, C(1-12)alkyl, C(2-12)alkenyl, C(2-12)alkynyl, —OR', —COR', —COOR', or —NHR', wherein R' is H or C(1-8)alkyl, $R_3, R_4$ are independently of each other H, nitroso, C(1-12)alkyl, —OR', —COR' or halosubstituted —COR', wherein R' represents H or C(1-8)alkyl, $A_1$ is H or a capping group, $A_2$ is H or a capping group, $M_1$ is a linear or macrocyclic polyaminocarboxylate, such as DTPA, DOTA, DO3A, HP-DO3A, EDTA, TETA, NOTA, DOTMA, complexed with a radioimaging metal ion, $m_1, m_2$ are independently of each other 0, 1, 2 or 3, $L_1, L_4$ are independently of each other a covalent bond or a straight-chain or branched C(1-8)alkyl, which is unsubstituted or substituted by at least one CN, Hal, OR', NHR', $CO_2R'$ or $NO_2$, wherein R' represents H or C(1-8)alkyl, $L_2$ is a covalent bond or a linking group, such as straight-chain or branched C(1-8)alkyl, which is unsubstituted or substituted by at least one OR', NHR', or $CO_2R'$, and wherein one or more of the non-adjacent $CH_2$ groups may independently be replaced by a group selected from —O—, —CO—, —CO—O—, —O—CO—, —NR'—, —NR'—CO—, —CO—NR', wherein R' represents H or C(1-8)alkyl, $S_1, S_2$ are independently of each other a single bond or a spacer selected from a straight-chain or branched C(1-12)alkyl, which is unsubstituted or substituted by at least one CN, Hal, OR', NHR', $CO_2R'$, SH, $SO_3H$ or $NO_2$, and wherein one or more of the non-adjacent $CH_2$ groups may independently be replaced by —O—, —CO—, —CO—O—, —O—CO—, —NR'—, —NR'—CO—, —CO—NR'—, —NR'—CO—O—, —O—CO—NR'—, —NR'—CO—NR'—, —CH=CH—, —C≡C—, —O—CO—O—, —S—R'—, —$SO_3R'$—, wherein R represents H or C(1-8)alkyl $D_1$ is a group selected from H, halogen, C(1-12)alkyl, C(2-12)alkenyl, C(2-12)alkynyl, —$OR_5$, —$COR_5$, —$COOR_5$, —$NHR_5$, —$CONHR_5$, wherein $R_5$ represents H, C(1-12)alkyl, C(2-12)alkenyl, or C(2-12)alkynyl, $D_2$ is an acidic group, $L_{3'}$ is straight-chain or branched C(1-8)alkyl, which is unsubstituted or substituted by at least one Hal, OR', NHR', or $CO_2R'$, and wherein one or more of the non-adjacent $CH_2$ groups may independently be replaced by a group selected from —O—, —CO—, —CO—O—, —NR'—, —NR'—CO—, wherein R' represents H or C(1-8)alkyl, p,q are independently of each other 0, 1, 2, 3, 4, 5 or 6, k is 0 or 1, and r has a value of 1 to 7.

In yet further embodiments the present invention provides compounds of formula I having formulae VII a-e
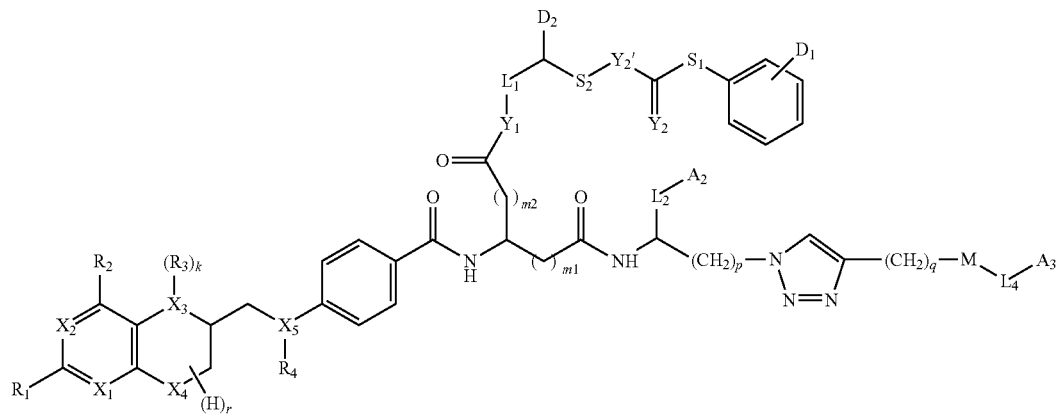
VIIa
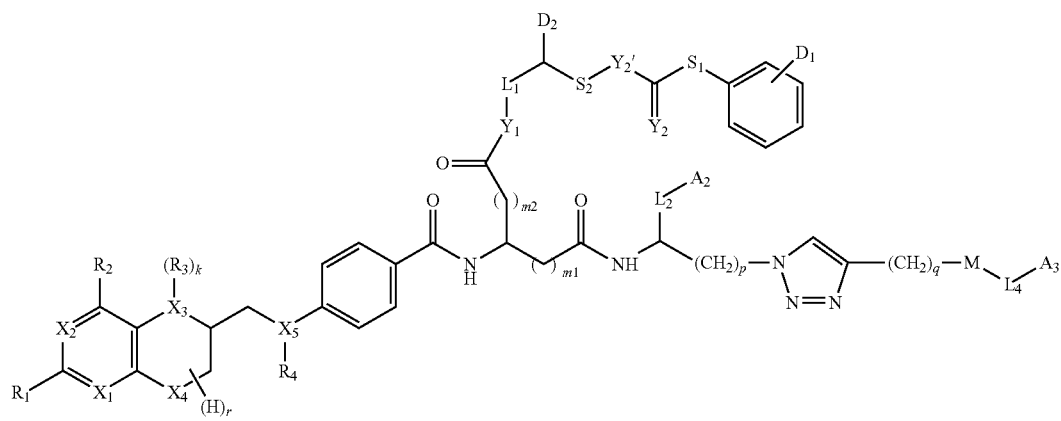
VIIb
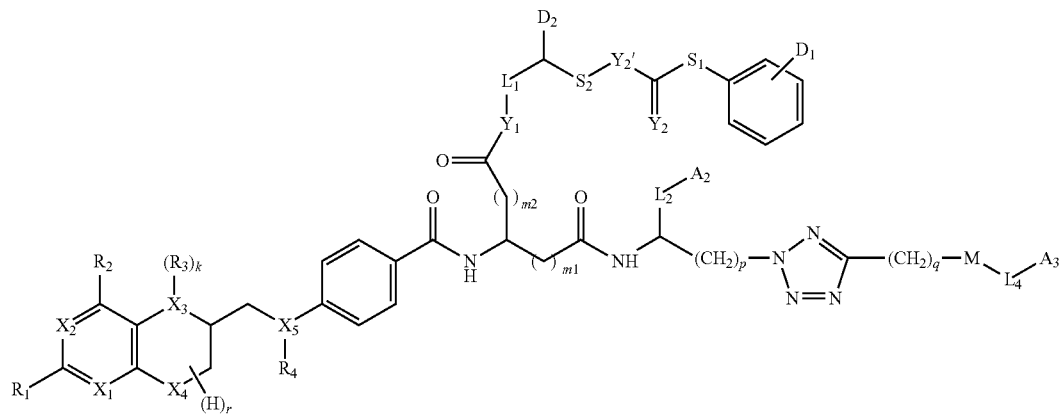
VIIc

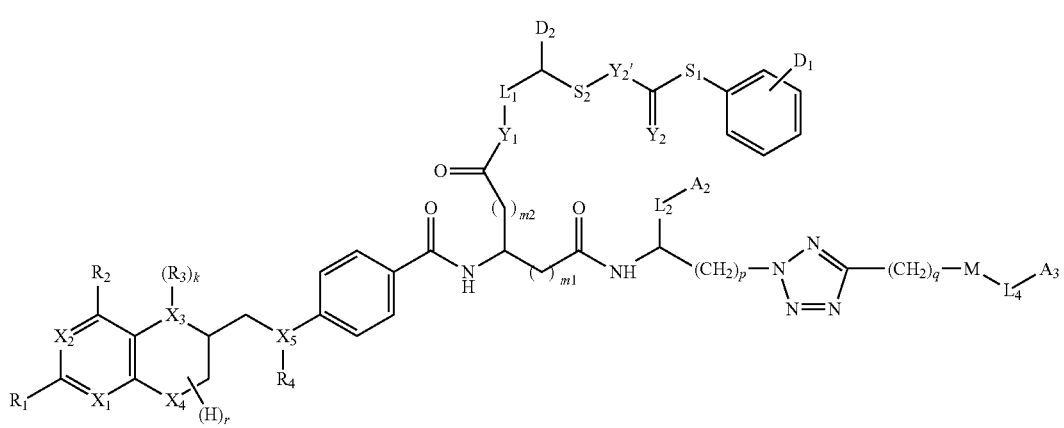

VIId

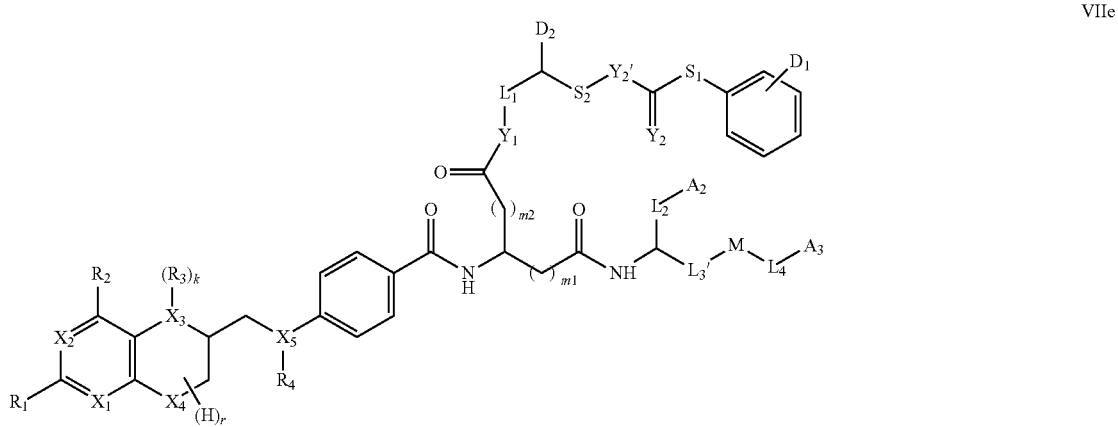

VIIe wherein
$X_1$ to $X_5$ are independently of each other C, N or O, preferably N or O,
$Y_1$, $Y_2$, $Y_2'$ are independently of each other N, O or S,
$R_1$, $R_2$ are independently of each other H, halogen, C(1-12) alkyl, C(2-12)alkenyl, C(2-12)alkynyl, —$OR_5$, —$COR_5$, —$COOR_5$, —$NHR_5$, $CONHR_5$, wherein $R_5$ represents H, halo, C(1-12)alkyl, C(2-12)alkenyl, C(2-12)alkynyl, —OR', —COR', —COOR', or —NHR', wherein R' is H or C(1-8)alkyl,
$R_3$, $R_4$ are independently of each other H, nitroso, C(1-12)alkyl, —OR', —COR' or halosubstituted —COR', wherein R' represents H or C(1-8)alkyl,
$A_2$ is H or a capping group,
$A_3$ is H or a capping group,
M is a radionuclide-based therapeutic or diagnostic moiety $M_1$ or $M_2$, wherein $M_1$ is a chelated metal radionuclide selected from a linear or macrocyclic polyaminocarboxylate, such as DTPA, DOTA, DO3A, HP-DO3A, EDTA, TETA, NOTA, DOTMA, complexed with a metal radionuclide, and wherein $M_2$ is a gamma- or positron-emitting radioimaging non-metal radionuclide, preferably selected from $^{11}$C, $^{13}$N, $^{15}$O, $^{17}$F, $^{18}$F, $^{75}$Br, $^{76}$Br, $^{77}$Br, $^{123}$I, $^{124}$I, $^{131}$I, optionally in combination with a prosthetic group,
$m_1$, $m_2$ are independently of each other 0, 1, 2 or 3,
$L_1$, $L_4$ are independently of each other a covalent bond or a straight-chain or branched C(1-8)alkyl, which is unsubstituted or substituted by at least one CN, Hal, OR', NHR', $CO_2R'$ or $NO_2$, wherein R' represents H or C(1-8)alkyl,
$L_2$ is a covalent bond or a linking group, such as straight-chain or branched C(1-8)alkyl, which is unsubstituted or substituted by at least one OR', NHR', or $CO_2R'$, and wherein one or more of the non-adjacent $CH_2$ groups may independently be replaced by a group selected from —O—, —CO—, —CO—O—, —O—CO—, —NR'—, —NR'—CO—, —CO—NR', wherein R' represents H or C(1-8)alkyl,
$S_1$, $S_2$ are independently of each other a single bond or a spacer selected from a straight-chain or branched C(1-12) alkyl, which is unsubstituted or substituted by at least one CN, Hal, OR', NHR', $CO_2R'$, SH, $SO_3H$ or $NO_2$, and wherein one or more of the non-adjacent $CH_2$ groups may independently be replaced by —O—, —CO—, —CO—O—, —O—CO—, —NR'—, —NR'—CO—, —CO—NR'—, —NR'—CO—O—, —O—CO—NR'—, —NR'—CO—NR'—, —CH=CH—, —C↓C—, —O—CO—O—, —S—R'—, —$SO_3R'$—, wherein R represents H or C(1-8)alkyl,
$D_1$ is a group selected from H, halogen, C(1-12)alkyl, C(2-12)alkenyl, C(2-12)alkynyl, —$OR_5$, —$COR_5$, —$COOR_5$, —$NHR_5$, —$CONHR_5$, wherein $R_5$ represents H, C(1-12)alkyl, C(2-12)alkenyl, or C(2-12)alkynyl,
$D_2$ is an acidic group,
$L_{3'}$ is straight-chain or branched C(1-8)alkyl, which is unsubstituted or substituted by at least one Hal, OR', NHR', or $CO_2R'$, and wherein one or more of the non-adjacent $CH_2$ groups may independently be replaced by a group selected from —O—, —CO—, —CO—O—, —NR'—, —NR'—CO—, wherein R' represents H or C(1-8)alkyl,
p,q are independently of each other 0, 1, 2, 3, 4, 5 or 6,
k is 0 or 1,
r has a value of 1 to 7.

In yet further embodiments the present invention provides compounds of formula I having formulae VIII a-e
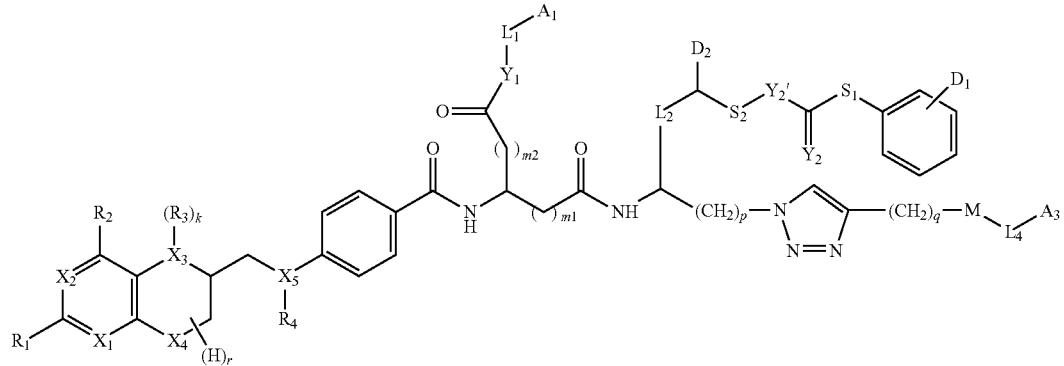
VIIIa
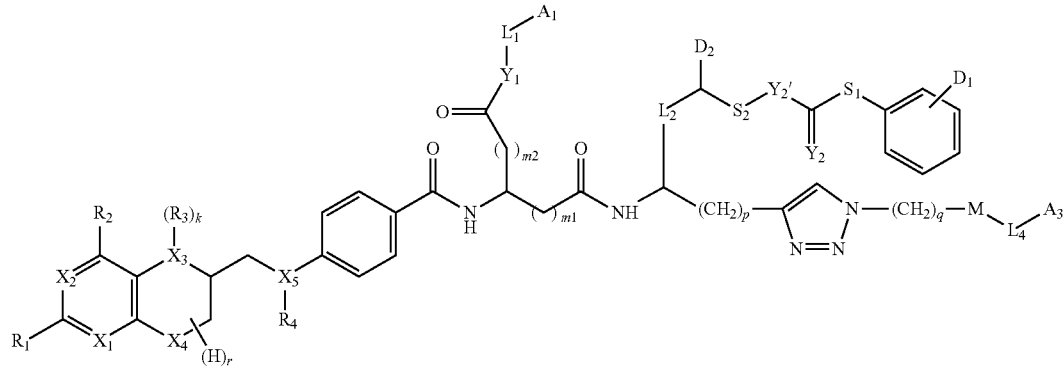
VIIIb
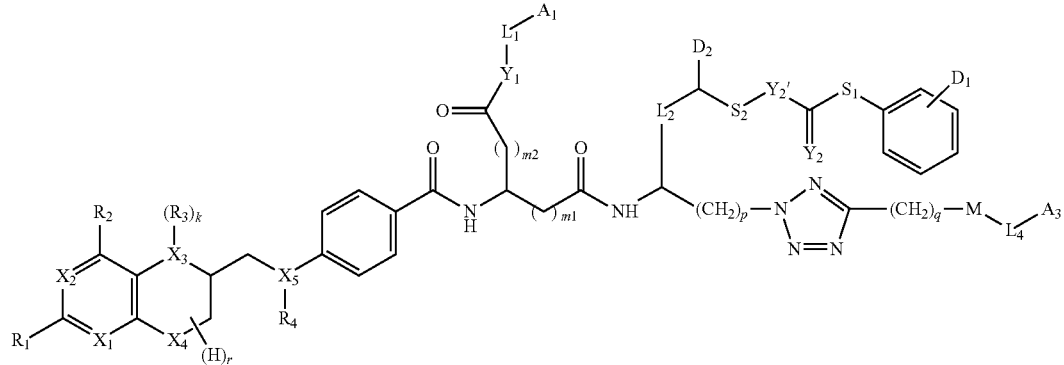
VIIIc
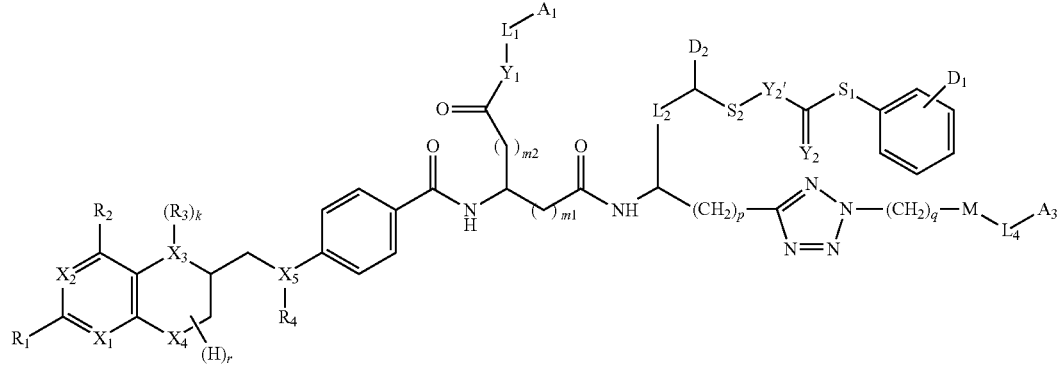
VIIId VIIIe

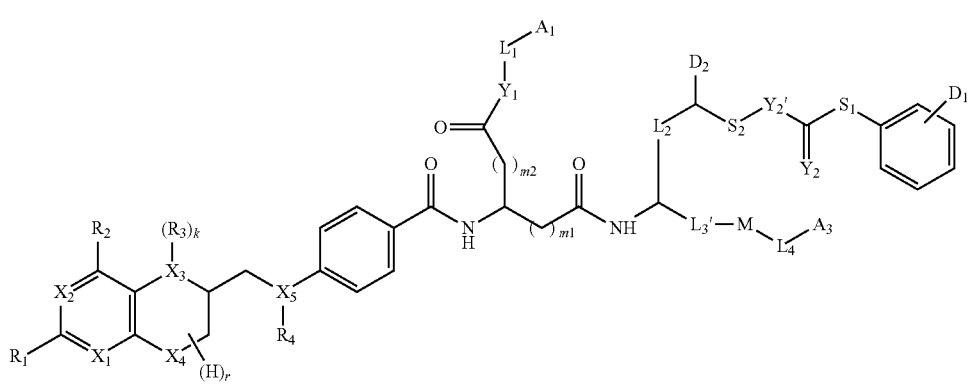

wherein
$X_1$ to $X_5$ are independently of each other C, N or O, preferably N or O, $Y_1, Y_2, Y_{2'}$ are independently of each other N, O or S, $R_1, R_2$ are independently of each other H, halogen, C(1-12)alkyl, C(2-12)alkenyl, C(2-12)alkynyl, —$OR_5$, —$COR_5$, —$COOR_5$, —$NHR_5$, $CONHR_5$, wherein $R_5$ represents H, halo, C(1-12)alkyl, C(2-12)alkenyl, C(2-12)alkynyl, —OR', —COR', —COOR', or —NHR', wherein R' is H or C(1-8)alkyl, $R_3, R_4$ are independently of each other H, nitroso, C(1-12)alkyl, —OR', —COR' or halosubstituted —COR', wherein R' represents H or C(1-8)alkyl, $A_1$ is H or a capping group, $A_3$ is H or a capping group, M is a radionuclide-based therapeutic or diagnostic $M_1$ or $M_2$, wherein $M_1$ is a chelated metal radiometal selected from a linear or macrocyclic polyaminocarboxylate, such as DTPA, DOTA, DO3A, HP-DO3A, EDTA, TETA, NOTA, DOTMA, complexed with a radionuclide metal, and wherein $M_2$ is a gamma- or positron-emitting non-metal radionuclide, preferably selected from $^{11}$C, $^{13}$N, $^{15}$O, $^{17}$F, $^{18}$F, $^{75}$Br, $^{76}$Br, $^{77}$Br, $^{123}$I, $^{124}$I, $^{131}$I, optionally in combination with a prosthetic group, $m_1, m_2$ are independently of each other 0, 1, 2 or 3, $L_1, L_4$ are independently of each other a covalent bond or a straight-chain or branched C(1-8)alkyl, which is unsubstituted or substituted by at least one CN, Hal, OR', NHR', $CO_2R'$ or $NO_2$, wherein R' represents H or C(1-8)alkyl, $L_2$ is a covalent bond or a linking group, such as straight-chain or branched C(1-8)alkyl, which is unsubstituted or substituted by at least one OR', NHR', or $CO_2R'$, and wherein one or more of the non-adjacent $CH_2$ groups may independently be replaced by a group selected from —O—, —CO—, —CO—O—, —O—CO—, —NR'—, —NR'—CO—, —CO—NR', wherein R' represents H or C(1-8)alkyl, $S_1, S_2$ are independently of each other a single bond or a spacer selected from a straight-chain or branched C(1-12)alkyl, which is unsubstituted or substituted by at least one CN, Hal, OR', NHR', $CO_2R'$, SH, $SO_3H$ or $NO_2$, and wherein one or more of the non-adjacent $CH_2$ groups may independently be replaced by —O—, —CO—, —CO—O—, —O—CO—, —NR'—, —NR'—CO—, —CO—NR'—, —NR'—CO—O—, —O—CO—NR'—, —NR'—CO—NR'—, —CH═CH—, —C≡C—, —O—CO—O—, —S—R'—, —$SO_3R'$—, wherein R represents H or C(1-8)alkyl, $D_1$ is a group selected from H, halogen, C(1-12)alkyl, C(2-12)alkenyl, C(2-12)alkynyl, —$OR_5$, —$COR_5$, —$COOR_5$, —$NHR_5$, —$CONHR_5$, wherein $R_5$ represents H, C(1-12)alkyl, C(2-12)alkenyl, or C(2-12)alkynyl, $D_2$ is an acidic group, $L_{3'}$ is straight-chain or branched C(1-8)alkyl, which is unsubstituted or substituted by at least one Hal, OR', NHR', or $CO_2R'$, and wherein one or more of the non-adjacent $CH_2$ groups may independently be replaced by a group selected from —O—, —CO—, —CO—O—, —NR'—, —NR'—CO—, wherein R' represents H or C(1-8)alkyl, p,q are independently of each other 0, 1, 2, 3, 4, 5 or 6, k is 0 or 1, r has a value of 1 to 7.

In preferred embodiments, $Y_2$ is O and $Y_{2'}$ is NH.

Further preferred embodiments of the compounds of the invention include for example compounds wherein $X_1$ to $X_5$ are N, $R_1$ is $NY_6Y_7$, $R_2$ is O, $R_4$ is $Y_8$, k is 0 and r is 1.

Thus the invention contemplates more specifically compounds of formulas IX a-e, wherein $Y_1, Y_2$ are O, $Y_3, Y_{2'}$ are NH and $L_1$ is preferably a covalent bond, IXa

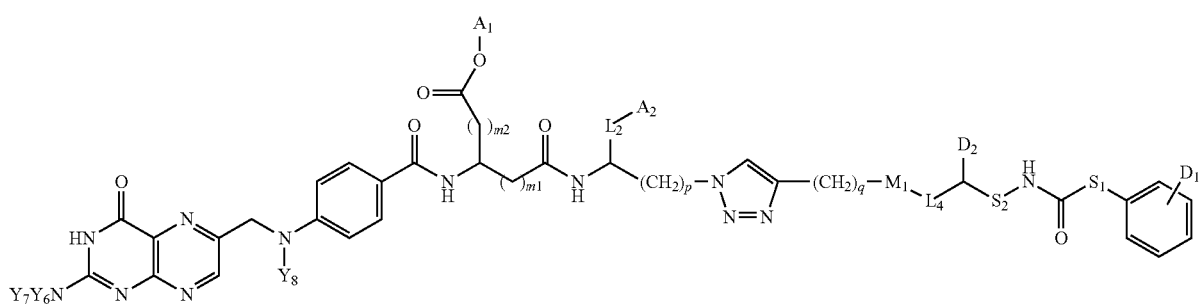

-continued

IXb

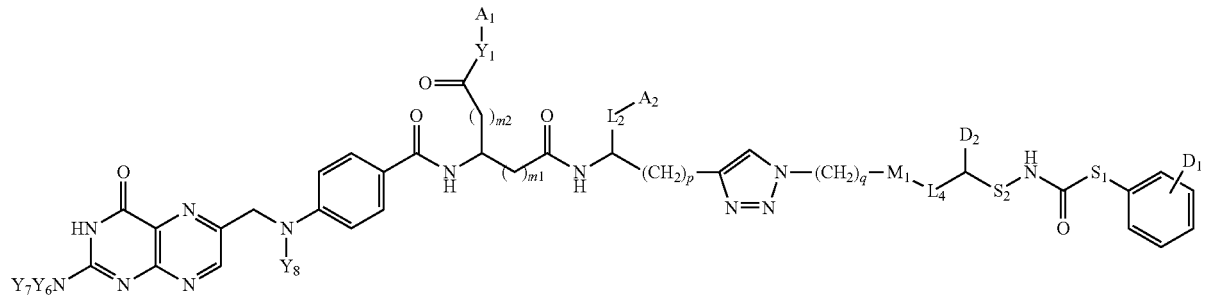

IXc

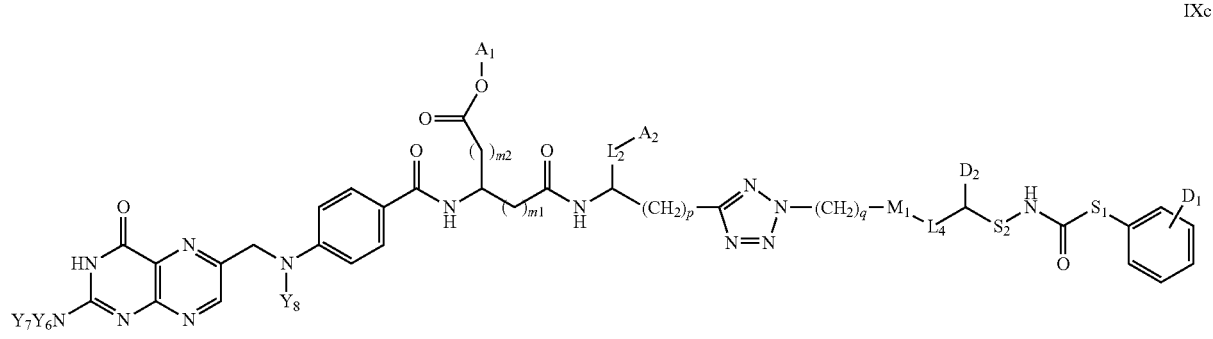

IXd

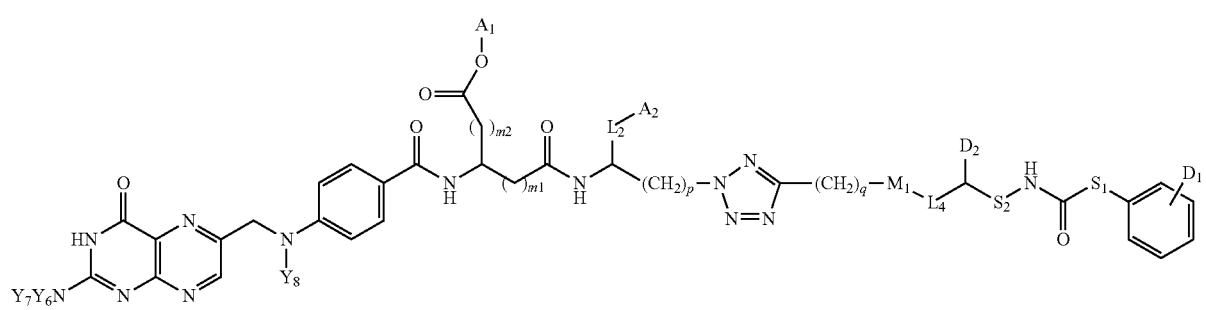

IXe

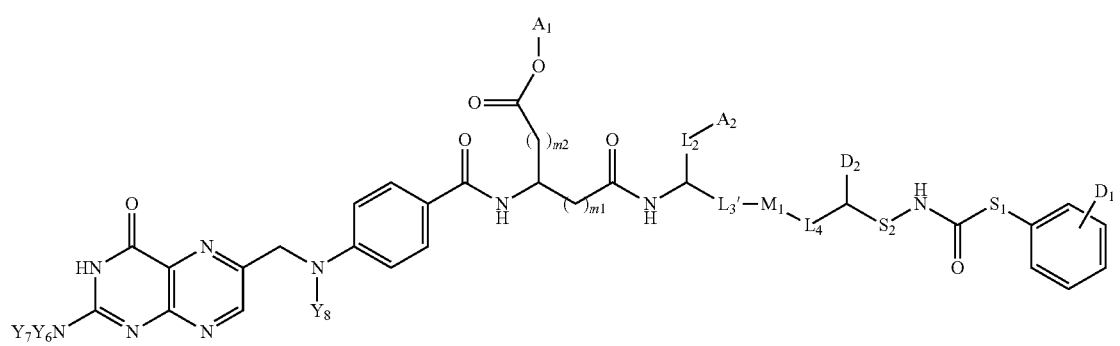

wherein, $Y_6, Y_7$ are independently of each other selected from H, halo, C(1-12)alkyl, C(2-12)alkenyl, C(2-12)alkynyl, —OR', —COR', COOR', and —NHR', wherein R' is H or C(1-8) alkyl, $Y_8$ is selected from H, nitroso, C(1-12)alkyl, —OR', —COR', and halosubstituted —COR', wherein R' is H or C(1-12) alkyl, $A_1$ is H or a carboxy protecting group, $A_2$ is H or capping group $M_1$ is a linear or macrocyclic polyaminocarboxylate, such as DTPA, DOTA, DO3A, HP-DO3A, EDTA, TETA, NOTA, DOTMA, complexed with a radioimaging metal ion, $m_1, m_2$ are independently of each other 0, 1, 2 or 3, preferably $m_1$ is 0 and $m_2$ is 2 or $m_1$ is 2 and $m_2$ is 0, $L_2$ is a covalent bond or a straight-chain or branched C(1-8) alkyl, which is unsubstituted or substituted by at least one OR', NHR', or $CO_2R'$, and wherein one or more of the non-adjacent $CH_2$ groups may independently be replaced by a group selected from —O—, —CO—, —CO—O—, —O—CO—, —NR'—, —NR'—CO—, —CO—NR', wherein R' represents H or C(1-8)alkyl, L$_4$ is a covalent bond or a straight-chain or branched C(1-8) alkyl, which is unsubstituted or substituted by at least one CN, Hal, OR', NHR', CO$_2$R' or NO$_2$, wherein R' represents H or C(1-8)alkyl, S$_1$, S$_2$ are independently of each other a single bond or a spacer selected from a straight-chain or branched C(1-12) alkyl, which is unsubstituted or substituted by at least one CN, Hal, OR', NHR', CO$_2$R', SH, SO$_3$H or NO$_2$, and wherein one or more of the non-adjacent CH$_2$ groups may independently be replaced by —O—, —CO—, —CO—O—, —O—CO—, —NR'—, —NR'—CO—, —CO—NR'—, —NR'—CO—O—, —O—CO—NR'—, —NR'—CO—NR'—, —CH=CH—, —C≡C—, —O—CO—O—, —S—R'—, —SO$_3$R'—, wherein R represents H or C(1-8)alkyl, D$_1$ is a group selected from H, halogen, C(1-12)alkyl, preferably halogen, D$_2$ is an acidic group selected from —COOH, —SO$_3$H, —SO$_2$H, —NR'SO$_3$H, —P(O)(OH)$_2$, L$_3$, is straight-chain or branched C(1-8)alkyl, which is unsubstituted or substituted by at least one Hal, OR', NHR', or CO$_2$R', and wherein one or more of the non-adjacent CH$_2$ groups may independently be replaced by a group selected from —O—, —CO—, —CO—O—, —NR'—, —NR'—CO—, wherein R' represents H or C(1-8)alkyl, p,q are independently of each other 0, 1, 2, 3, 4, 5 or 6.

In preferred embodiments, L$_2$ is a covalent bond or a straight-chain or branched unsubstituted C(1-6)alkyl, most preferably a covalent bond; and/or (i) m1 is 0 and m2 is 2 or (ii) m1 is 2 and m2 is 0; and/or S$_1$ and S$_2$ are independently of each other a single bond or a spacer selected from a straight-chain or branched C(1-8)alkyl, wherein one or more of the non-adjacent CH$_2$ groups may independently be replaced by —O—, —CO—, —COO —, —NR'—, —NR'—CO—, —CO—NR'—, —CH=CH—, wherein R' represents H or C(1-8)alkyl, more preferably a single bond or a spacer selected from a straight-chain or branched C(1-6)alkyl.

Further compounds include compounds of formulas X a-e, wherein Y$_2$ is O; Y$_1$, Y$_3$, Y$_2$' are NH; and L$_4$ is preferably a covalent bond,

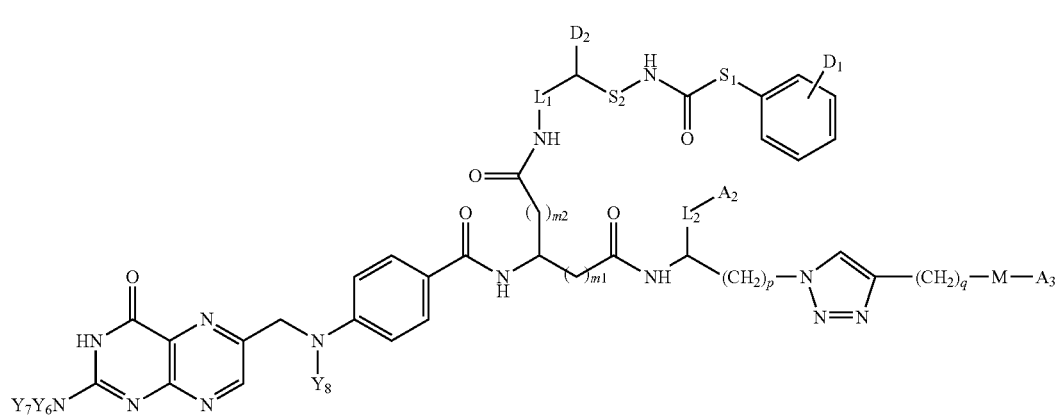

Xa

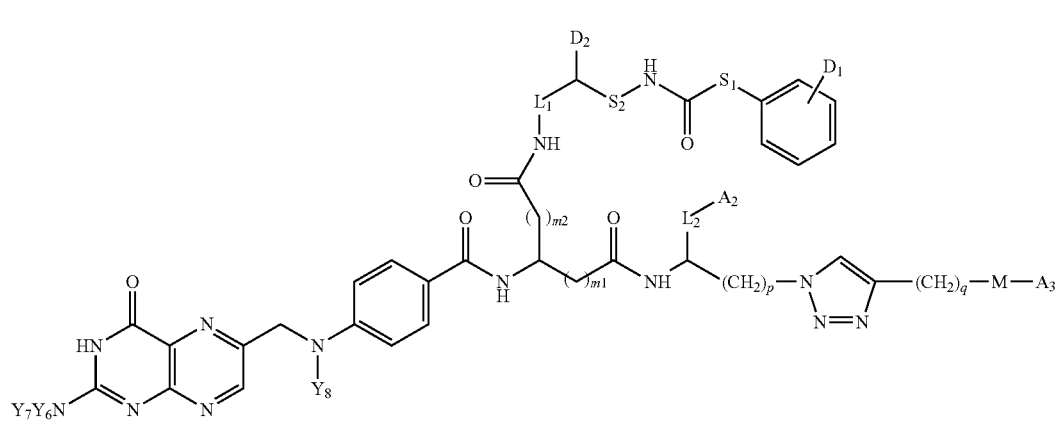

Xb

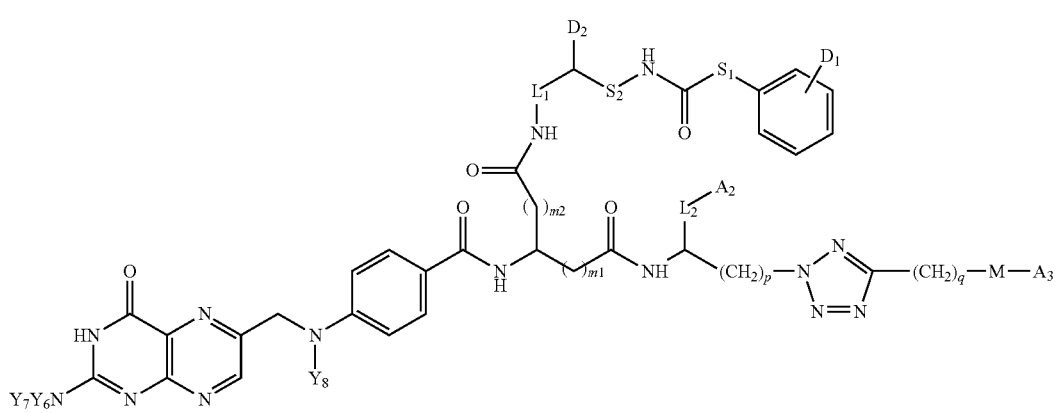

Xc

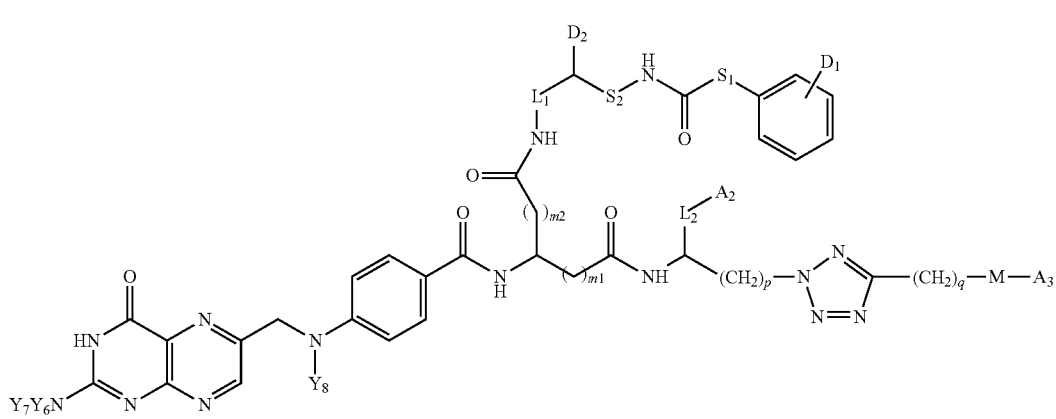

Xd

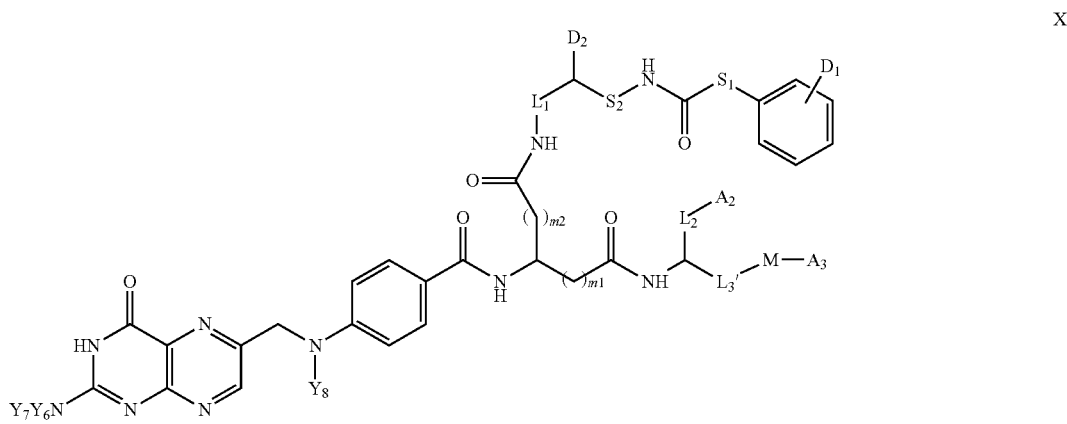

Xe wherein
$Y_6, Y_7$ are independently of each other selected from H, halo, C(1-12)alkyl, C(2-12)alkenyl, C(2-12)alkynyl, —OR', —COR', COOR', and —NHR', wherein R' is H or C(1-8) alkyl, $Y_8$ is selected from H, nitroso, C(1-12)alkyl, —OR', —COR', and halosubstituted —COR', wherein R' is H or C(1-12) alkyl, $A_2$ is H or a capping group, $A_3$ is H or a capping group, e.g. a protecting group, M is a radionuclide-based therapeutic or diagnostic moiety $M_1$ or $M_2$, wherein $M_1$ is a chelated metal radionuclide selected from a linear or macrocyclic polyaminocarboxylate, such as DTPA, DOTA, DO3A, HP-DO3A, EDTA, TETA, NOTA, DOTMA, complexed with a metal radionuclide, and wherein $M_2$ is a gamma- or positron-emitting non-metal radionuclide, preferably selected from $^{11}C$, $^{13}N$, $^{15}O$, $^{17}F$, $^{18}F$, $^{75}Br$, $^{76}Br$, $^{77}Br$, $^{123}I$, $^{124}I$, $^{131}I$, optionally in combination with a prosthetic group, $m_1, m_2$ are independently of each other 0, 1, 2 or 3, preferably $m_1$ is 0 and $m_2$ is 2 or $m_1$ is 2 and $m_2$ is 0, $S_1, S_2$ are independently of each other a single bond or a spacer selected from a straight-chain or branched C(1-12) alkyl, which is unsubstituted or substituted by at least one CN, Hal, OR', NHR', $CO_2R'$, SH, $SO_3H$ or $NO_2$, and wherein one or more of the non-adjacent $CH_2$ groups may independently be replaced by —O—, —CO—, —CO—O—, —O—CO—, —NR'—, —NR'—CO—, —CO—NR'—, —NR'—CO—O—, —O—CO—NR'—, —NR'—CO—NR'—, —CH=CH—, —C≡C—, —O—CO—O—, —S—R'—, —$SO_3R'$—, wherein R represents H or C(1-8)alkyl, $D_1$ is a group selected from H, halogen, C(1-12)alkyl, preferably halogen, $D_2$ is an acidic group selected from —COOH, —SO₃H, —SO₂H, —NR'SO₃H, —P(O)(OH)₂, $L_1$ is a covalent bond or a straight-chain or branched C(1-8) alkyl, which is unsubstituted or substituted by at least one CN, Hal, OR', NHR', CO₂R' or NO₂, wherein R' represents H or C(1-8)alkyl, $L_2$ is a covalent bond or a straight-chain or branched C(1-8) alkyl, which is unsubstituted or substituted by at least one OR', NHR', or CO₂R', and wherein one or more of the non-adjacent CH₂ groups may independently be replaced by a group selected from —O—, —CO—, —CO—O—, —O—CO—, —NR'—, —NR'—CO—, —CO—NR', wherein R' represents H or C(1-8)alkyl, $L_3$, is straight-chain or branched C(1-8)alkyl, which is unsubstituted or substituted by at least one Hal, OR', NHR', or CO₂R', and wherein one or more of the non-adjacent CH₂ groups may independently be replaced by a group selected from —O—, —CO—, —CO—O—, —NR'—, —NR'—CO—, wherein R' represents H or C(1-8)alkyl, p,q are independently of each other 0, 1, 2, 3, 4, 5 or 6.

The invention also contemplates compounds of formulas XI a-e, wherein $Y_1, Y_2$ are O, $Y_{3}, Y_{2'}$ are NH and $L_1$ and $L_4$ are preferably a covalent bond,

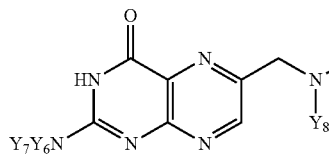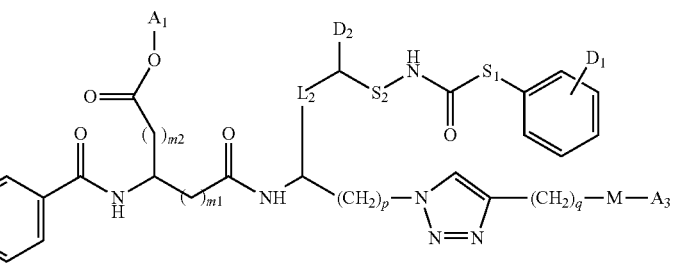

XIa

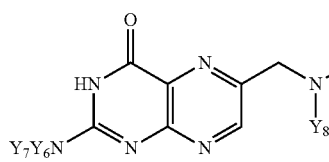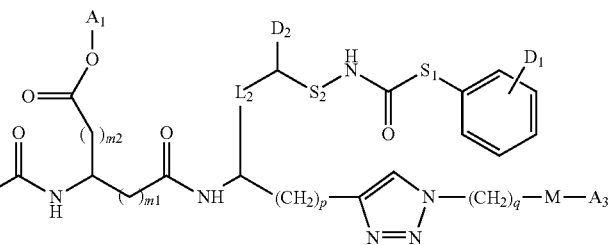

XIb

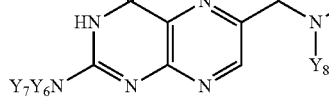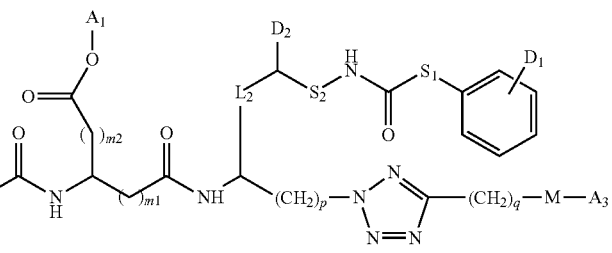

XIc

-continued

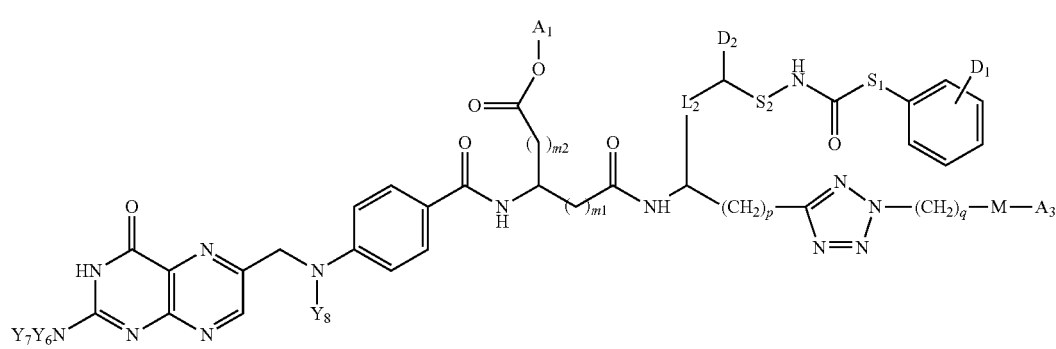

XId

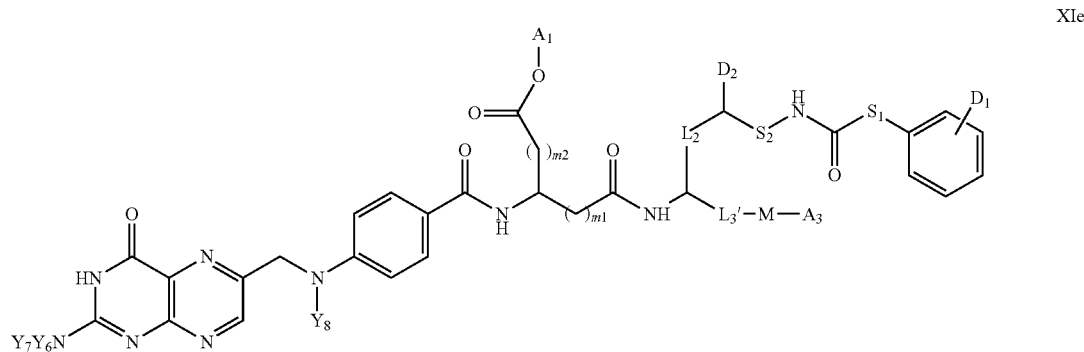

XIe wherein
- $Y_6, Y_7$ are independently of each other selected from H, halo, C(1-12)alkyl, C(2-12)alkenyl, C(2-12)alkynyl, —OR', —COR', —COOR', and —NHR', wherein R' is H or C(1-8)alkyl,
- $Y_8$ is selected from H, nitroso, C(1-12)alkyl, —OR', —COR', and halosubstituted —COR', wherein R' is H or C(1-12)alkyl,
- $A_1$ is H or carboxy protecting group,
- $A_3$ is H or a carboxy protecting group or a hydroxyl protecting group,
- M is a radionuclide-based therapeutic or diagnostic moiety $M_1$ or $M_2$, wherein $M_1$ is a chelated metal radionuclide selected from a linear or macrocyclic polyaminocarboxylate, such as DTPA, DOTA, DO3A, HP-DO3A, EDTA, TETA, NOTA, DOTMA, complexed with a metal radionuclide, and wherein $M_2$ is a gamma- or positron-emitting non-metal radionuclide, preferably selected from $^{11}$C, $^{13}$N, $^{15}$O, $^{17}$F, $^{18}$F, $^{75}$Br, $^{76}$Br, $^{77}$Br, $^{123}$I, $^{124}$I, $^{131}$I, optionally in combination with a prosthetic group,
- $m_1, m_2$ are independently of each other 0, 1, 2 or 3, preferably m1 is 0 and m2 is 2 or m1 is 2 and m2 is 0,
- $S_1, S_2$ are independently of each other a single bond or a spacer selected from a straight-chain or branched C(1-12)alkyl, which is unsubstituted or substituted by at least one CN, Hal, OR', NHR', CO$_2$R', SH, SO$_3$H or NO$_2$, and wherein one or more of the non-adjacent CH$_2$ groups may independently be replaced by —O—, —CO—, —CO—O—, —O—CO—, —NR'—, —NR'—CO—, —CO—NR'—, —NR'—CO—O—, —O—CO—NR'—, —NR'—CO—NR'—, —CH═CH—, —C≡C—, —O—CO—O—, —S—R'—, —SO$_3$R'—, wherein R represents H or C(1-8)alkyl,
- $D_1$ is a group selected from H, halogen, C(1-12)alkyl, preferably halogen,
- $D_2$ is an acidic group selected from —COOH, —SO$_3$H, —SO$_2$H, —NR'SO$_3$H, —P(O)(OH)$_2$,
- $L_2$ is a covalent bond or a straight-chain or branched C(1-8) alkyl, which is unsubstituted or substituted by at least one OR', NHR', or CO$_2$R', and wherein one or more of the non-adjacent CH$_2$ groups may independently be replaced by a group selected from —O—, —CO—, —CO—O—, —O—CO—, —NR'—, —NR'—CO—, —CO—NR', wherein R' represents H or C(1-8)alkyl,
- $L_{3'}$ is straight-chain or branched C(1-8)alkyl, which is unsubstituted or substituted by at least one Hal, OR', NHR', or CO$_2$R', and wherein one or more of the non-adjacent CH$_2$ groups may independently be replaced by a group selected from —O—, —CO—, —CO—O—, —NR'—, —NR'—CO—, wherein R' represents H or C(1-8)alkyl,
- p,q are independently of each other 0, 1, 2, 3, 4, 5 or 6.

In preferred embodiments, $L_1$ is a covalent bond or a straight-chain or branched unsubstituted C(1-6)alkyl, most preferably a covalent bond; and/or (i) $m_1$ is 0 and $m_2$ is 2 or (ii) $m_1$ is 2 and $m_2$ is 0; and/or $S_1$ and $S_2$ are independently of each other a single bond or a spacer selected from a straight-chain or branched C(1-8)alkyl, wherein one or more of the non-adjacent CH$_2$ groups may independently be replaced by —O—, —CO—, —COO—, —NR'—, —NR'—CO—, —CO—NR'—, —CH═CH—, wherein R' represents H or C(1-8)alkyl, more preferably a single bond or a spacer selected from a straight-chain or branched C(1-6)alkyl.

$L_2$ is preferably a covalent bond or a straight-chain or branched C1-, C2-, C3- or C4-alkyl, which is unsubstituted or substituted by at least one OR', NHR', or CO$_2$R', and wherein one or more of the non-adjacent CH$_2$ groups may independently be replaced by a group selected from —O—, —CO—, —CO—O—, —O—CO—.

$L_{3'}$ is preferably straight-chain or branched C(1-8)alkyl, which is unsubstituted or substituted by at least one OR', NHR', or CO$_2$R', and wherein one or more of the non-adjacent CH$_2$ groups may independently be replaced by a group selected from —CO—O— or —NR'—CO—, wherein R' represents H or C(1-8)alkyl.

Most preferred compounds of the invention are e.g.
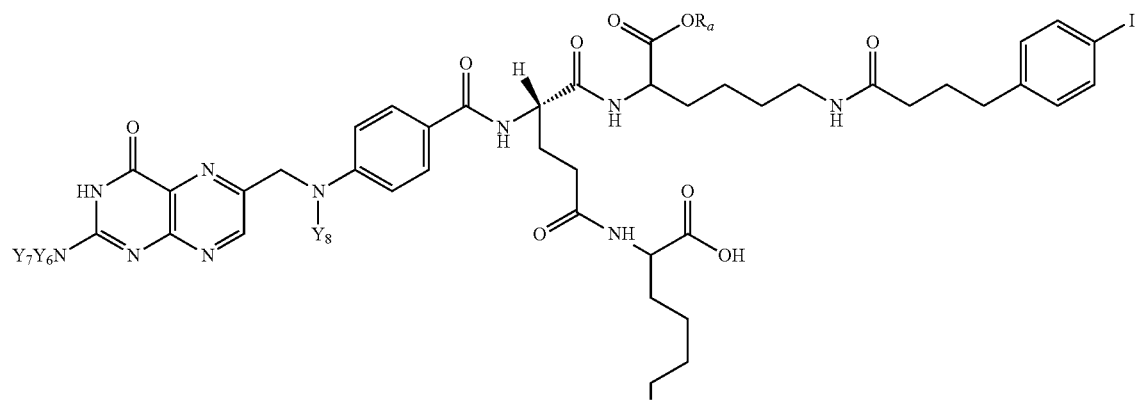
and
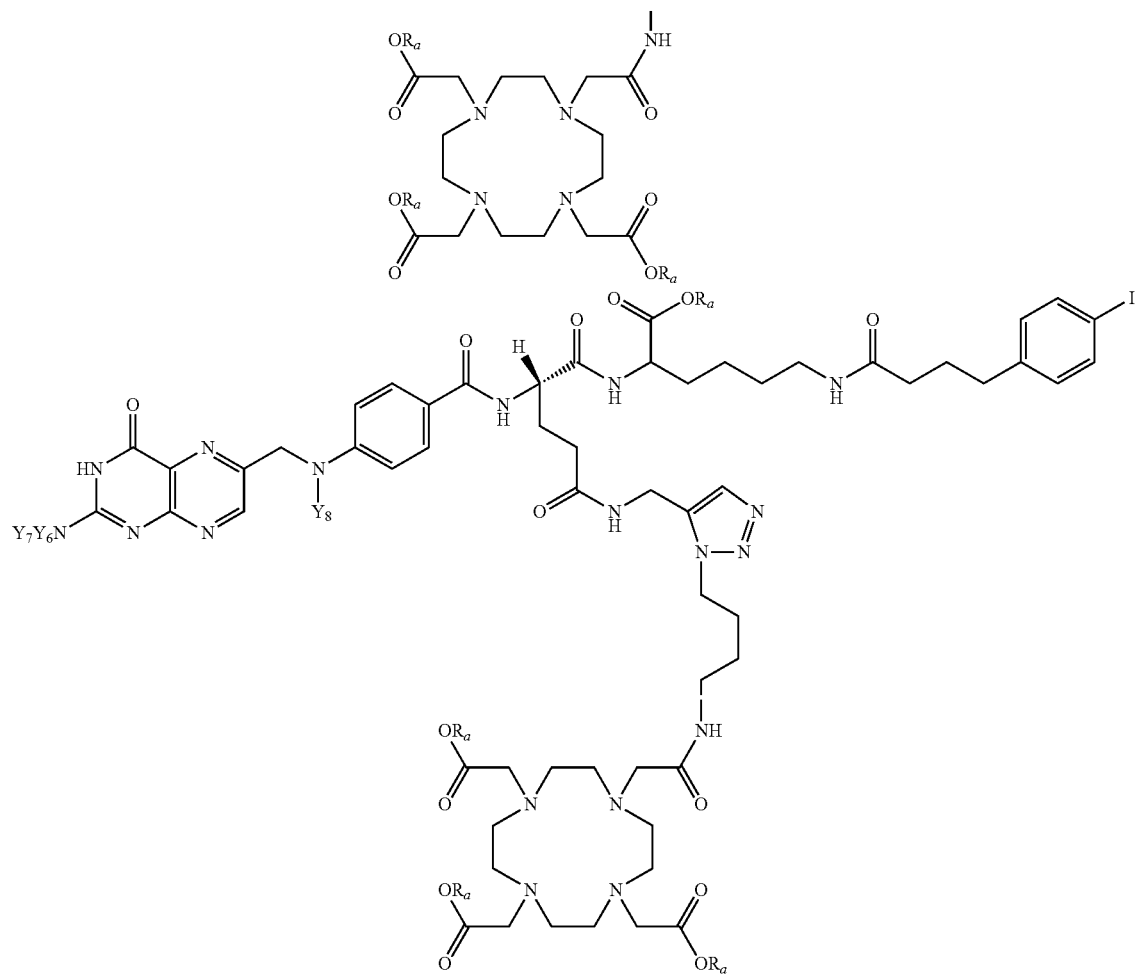

wherein $Y_6, Y_7$ are independently of each other selected from H, halo, C(1-12)alkyl, C(2-12)alkenyl, C(2-12)alkynyl, —OR', —COR', —COOR', and —NHR', wherein R' is H or C(1-8)alkyl, $Y_8$ is selected from H, nitroso, C(1-12)alkyl, —OR', —COR', and halosubstituted —COR', wherein R' is H or C(1-12)alkyl, $R_a$ is H or C(1-8)alkyl;

and compounds

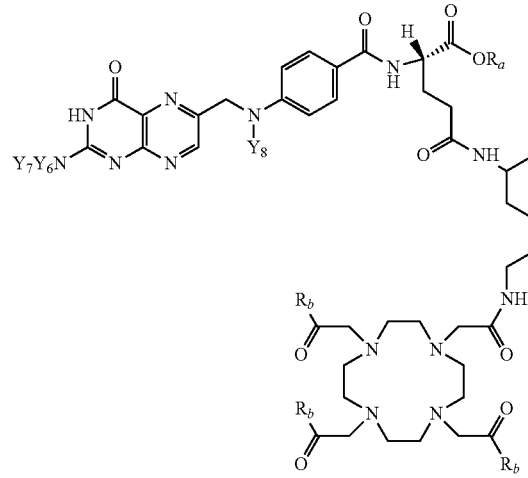

-continued

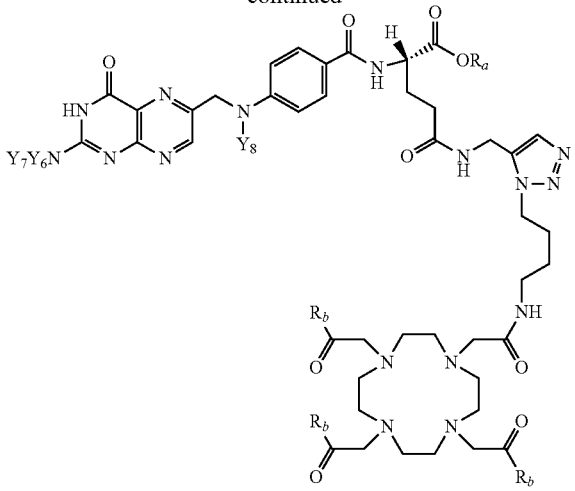

wherein $Y_6, Y_7$ are independently of each other selected from H, halo, C(1-12)alkyl, C(2-12)alkenyl, C(2-12)alkynyl, —OR', —COR', —COOR', and —NHR', wherein R' is H or C(1-8)alkyl, $Y_8$ is selected from H, nitroso, C(1-12)alkyl, —OR', —COR', and halosubstituted —COR', wherein R' is H or C(1-12)alkyl, $R_a$ is H or C(1-8)alkyl, $R_b$ is independently of each other selected from —OH, —OC(1-8)alkyl, or a group of formula (i)

(i)

with the proviso that at least one of groups R is a group of formula (i);
and compounds

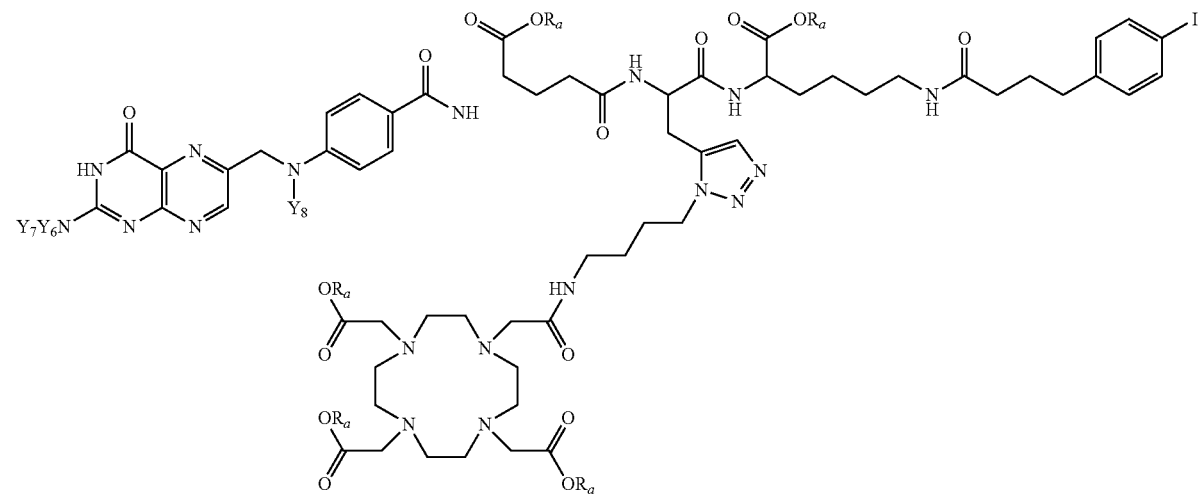

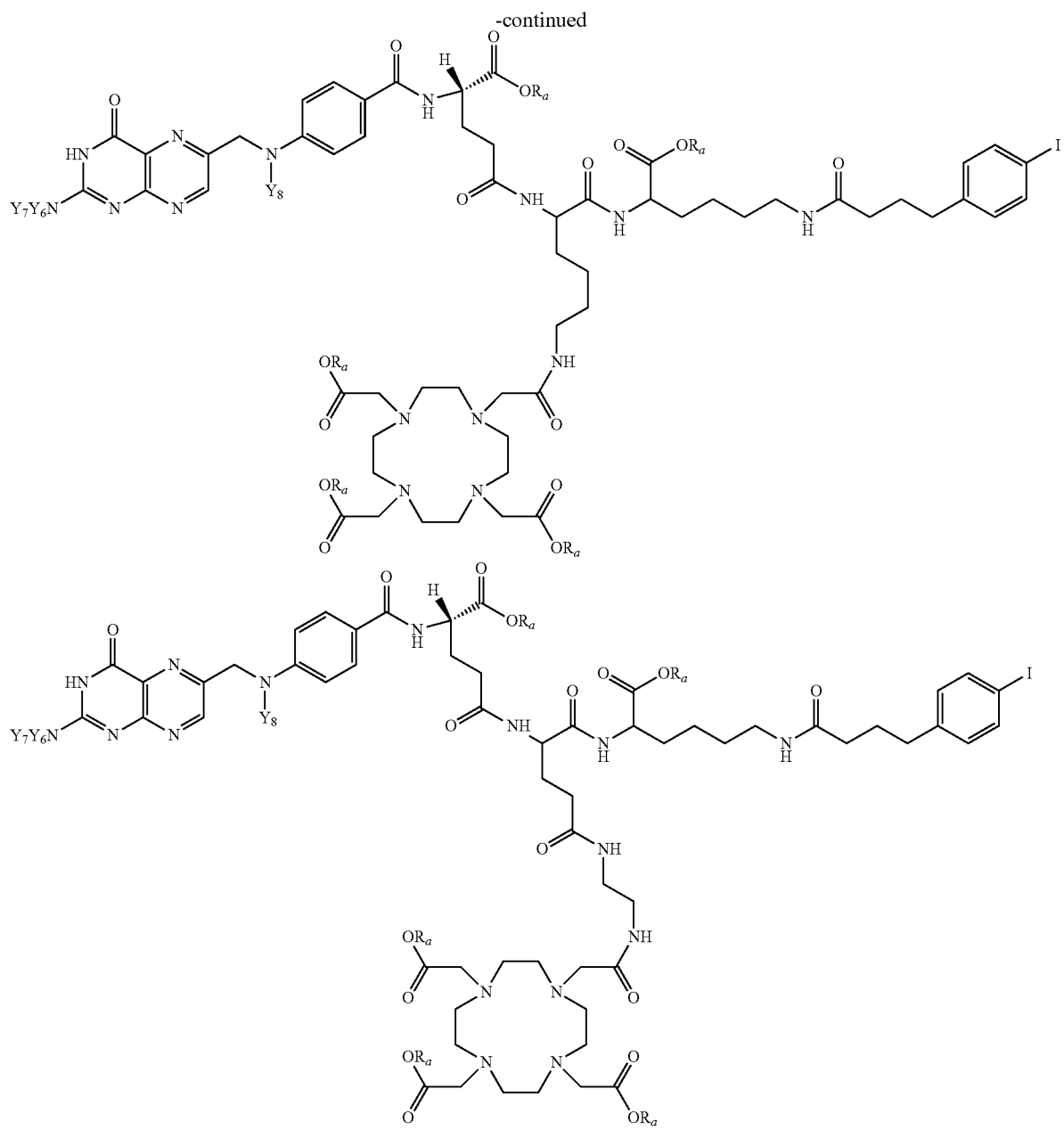

wherein
- $Y_6, Y_7$ are independently of each other selected from H, halo, C(1-12)alkyl, C(2-12)alkenyl, C(2-12)alkynyl, —OR', —COR', —COOR', and —NHR', wherein R' is H or C(1-8)alkyl,
- $Y_8$ is selected from H, nitroso, C(1-12)alkyl, —OR', —COR', and halosubstituted —COR', wherein R' is H or C(1-12)alkyl,
- $R_a$ is H or C(1-8)alkyl.

In another aspect the present invention also provides methods of synthesizing a compound of the invention. The synthesis is preferably based on a modular approach (using appropriately derivatized functionalities, i.e. folate group, albumin binder group and chelating group) and is based on standard coupling chemistries known in the art, including esterification, amidation, and the click-reaction. The latter reaction has been proven to be particularly useful and is based on the coupling of an azide and an alkyne group in a cycloaddition under thermal conditions or in the presence of a catalyst to obtain the final compound of choice (Kolb and Sharpless, Drug Discovery Today 2003, 8, 1128; Kolb et al. Angew. Chem. Int. Ed. 2001, 40, 2004; Rostovtsev, V. V. et al. Angew. Chem. Int. Ed. 2002, 41, 2596; US 2005/02222427; WO 06/116629). These reactions are known as Huisgen 1,3-dipolar cycloaddition (thermal conditions) and Click-Reaction (catalytic conditions) and have been described in the art (Kolb and Sharpless, Drug Discovery Today 2003, 8, 1128; Kolb et al. Angew. Chem. Int. Ed. 2001, 40, 2004; Rostovtsev et al. Angew. Chem. Int. Ed. 2002, 41, 2596; US 2005/02222427; WO 06/116629). More specifically compounds of formula I wherein the fivemembered heterocycle is a triazole are obtained by cycloaddition of an azide $R_a$—$N_3$ with an alkyne $R_b$—C≡C—$R_c$ and compounds of formula I wherein the five-membered heterocycle is a tetrazole are obtained by cycloaddition of an azide $R_a$—$N_3$ with a cyanide $R_b$—C≡N. All possible combinations are contemplated herein, i.e. $R_a$ being the folate derivative and $R_b$ being a chelating moiety or precursor thereof as well as $R_b$ being the folate derivative and $R_a$ being a chelating moiety or precursor thereof. Thus the modular and versatile nature of the reaction allows employing a wide variety of linkers to couple the imaging moiety to folic acid.

It will be obvious for a skilled person to select appropriate conditions for the various coupling steps and choose appropriate protecting groups PG (e.g. see Greene & Wuts, Eds., *Protective Groups in Organic Synthesis*, 2nd Ed., 1991, John Wiley & Sons, NY.) and leaving groups LG (e.g. a halogen, tosylate, mesylate, triflate, carbonate group).

It will also be obvious for a skilled person that the last step in the synthesis of the compounds of the invention preferably includes introducing the metal radionuclide (if the imaging moiety is a chelated metal radionuclide $M_1$) or the gamma- or positron-emitting non-metal radionuclide (if the imaging moiety is a gamma- or positron-emitting non-metal radionuclide $M_2$,)

Thus, if the imaging moiety is a chelated metal radionuclide $M_1$, such as selected from a linear or macrocyclic polyaminocarboxylate, such as DTPA, DOTA, DO3A, HP-DO3A, EDTA, TETA, NOTA, DOTMA, the present invention further provides a method of synthesizing a complex of the invention, which comprises labeling such a compound of the invention, which includes the steps of first obtaining a compound of the invention, and reacting the compound with a radionuclide as specified hereinabove, generally in the presence of a reducing agent to form a metal chelate complex between the compound of the invention and the radionuclide. The reducing agent may be any known reducing agent, but will preferably be a dithionite ion or a stannous ion.

Alternatively, if the imaging moiety is a gamma- or positron-emitting non-metal radionuclide $M_2$, preferably selected from $^{11}C$, $^{13}N$, $^{15}O$, $^{17}F$, $^{18}F$, $^{75}Br$, $^{76}Br$, $^{77}Br$, $^{123}I$, $^{124}I$, $^{131}I$, the present invention further provides a method of synthesizing the respective compound of the invention, which comprises introducing non-metal radionuclide $M_2$ from the corresponding precursor according to known methods in the art.

In a further aspect the invention provides pharmaceutical compositions comprising a diagnostic imaging amount or a therapeutically effective amount of at least one compound of the present invention and a pharmaceutically acceptable carrier therefore. In a preferred embodiment, the pharmaceutical compositions contain at least one compound wherein M is a chelated metal radionuclide $M_1$ selected from DTPA, DOTA, DO3A, HP-DO3A, EDTA, TETA, NOTA, DOTMA, complexed with a metal radionuclide, selected from e.g. $^{177}Lu$, $^{161}Tb$, $^{213}Bi$, or $^{111}In$. In another preferred embodiment, the pharmaceutical compositions contain at least one compound wherein M is a non-metal radionuclide $M_2$ selected from $^{18}F$, $^{123}I$, $^{124}I$, $^{131}I$.

As used herein, a pharmaceutically acceptable carrier, which is present in an appropriate dosage, includes solvents, dispersion media, antibacterial and antifungal agents, isotonic agents, and the like which are physiologically acceptable. The use of such media and agents are well-known in the art.

In a further aspect the present invention provides uses of compounds and/or pharmaceutical compositions of the present invention for convenient and effective administration to a subject in need for diagnostic imaging or radionuclide therapy. The subject of the methods of the present invention is preferably a mammal, such as an animal or a human, preferably a human.

Thus in a particular embodiment the present invention provides a method for diagnostic imaging of a cell or population of cells expressing a folate-receptor, said method comprising the steps of administering at least one compound or composition of the present invention in a diagnostic imaging amount, and obtaining a diagnostic image of said cell or population of cells.

The compounds and/or compositions of the present invention may also be used for radionuclide therapy agents useful for the treatment of a subject in need thereof.

Thus in another particular embodiment the present invention provides a method for radionuclide therapy comprising the steps of administering to a subject in need thereof at least one compound or composition of the present invention in therapeutically effective amounts, and after localization of said at least one compound or composition in the desired tissues, subjecting the tissues to irradiation to achieve the desired therapeutic effect.

In yet another embodiment the present invention provides a method for simultaneous diagnosis and radionuclide therapy comprising the steps of administering to a subject in need thereof at least one compound or composition of the present invention in a diagnostically and therapeutically effective amount, and after localization of said at least one compound or composition in the desired tissues, subjecting the tissues to irradiation, and obtaining a diagnostic image of said tissues to follow the course of treatment.

An image of a cell or tissue expressing the folate receptor, i.e. a tumor cell or tissue, labeled with one or more of the compounds or compositions of the present invention can be detected using a radiation detector, e.g. a γ-radiation detector. One such procedure utilizes scintigraphy. Tomographic imaging procedures such as single photon emission computed tomography (SPECT) or positron emission tomography (PET) can also be used to improve visualization. Selection and use of such radiation detectors is within the skill of one of ordinary skill in the art. Thus, a diagnostic imaging amount of a compound or composition of the present invention to be administered may be selected in an amount sufficient such as to produce a diagnostic image of an organ or other site of the subject as described hereinabove. A therapeutically effective amount of a compound or composition of the present invention to be administered may be selected in an amount sufficient such as to produce a desired radiotherapeutic effect. More specifically a therapeutically effective amount is an amount of at least one of the compounds of the present invention, which will permit sufficient tumor localization of the complex to stop and/or diminish tumor growth or size. As provided herein tumor growth or size can be monitored using the methods of the present invention or any other known diagnostic imaging procedure.

Clearly the specific activity of the metal radionuclide of choice, e.g. $^{99m}Tc$, $^{186/188}Re$, $^{111}In^{+3}$, $^{67/68}Ga^{+3}$, $^{90}Y^{+3}$, $^{109}Pd^{+2}$, $^{105}Rh^{+3}$, $^{177}Lu$, $^{64/67}Cu$ $^{166}Ho$, $^{213}Bi$, preferably $^{99m}Tc$ or $^{186/188}Re$, or the non-metal radionuclide of choice, e.g. $^{11}C$, $^{13}N$, $^{15}O$, $^{17}F$, $^{18}F$, $^{75}Br$, $^{76}Br$, $^{77}Br$, $^{123}I$, $^{124}I$, $^{131}I$, preferably $^{18}F$, $^{123}I$, $^{124}I$, $^{131}I$, will be taken into consideration in determining a dosage for diagnostic imaging or radionuclide therapy.

Generally, the unit dose to be administered has a radioactivity of about 0.01 mCi to about 300 mCi, preferably 10 mCi to about 200 mCi. For a solution to be injected a preferred unit dosage is from about 0.01 mL to about 10 mL. After e.g. intravenous administration, imaging of the organ or tumor in vivo can take place, if desired, from within minutes to hours or even longer, after the radiolabeled reagent has been administered to a subject. Typically, a sufficient amount of the administered dose will accumulate in the targeted area to be imaged within about 1-4 hours.

The compounds and/or compositions of the present invention may be administered by an appropriate route such as parentally (for example, intravenously), intramuscularly or intraperitoneally or by any other suitable method. For example, the compounds and/or compositions of this invention may be administered to a subject by bolus or slow infusion intravenous injection. The suitable forms for injection include sterile aqueous solutions or dispersions and sterile powders of the above mentioned compounds and/or compositions of the present invention.

The compounds or pharmaceutical compositions are preferably sterile. Sterilization can be accomplished by any art recognized technique, including but not limited to, addition of antibacterial of antifungal agents, for example, paraben, chlorobutanol, phenol, sorbic acid, thimerosal, and the like.

The compounds and/or compositions of the invention may also be used for in vitro detection of a cell expressing the folate receptor in a tissue biopsy taken from a subject. Thus in a further embodiment the present invention provides a method for in vitro detection of a cell expressing the folate receptor, e.g. a tumor cell, in a tissue sample which includes contacting said tissue sample with a compound or composition of the present invention in effective amounts and for sufficient time and conditions to allow binding to occur and detecting such binding by imaging techniques.

Samples can be collected by procedures known to the skilled person, e.g., by collecting a tissue biopsy or a body fluid, by aspirating for tracheal or pulmonary samples and the like.

Tissue samples to be tested include any tissue suspected to contain a cell expressing a folate receptor, such as tumor cells, epithelial cells, kidneys, gastrointestinal or the hepatobiliary system, and others. Samples can be sectioned, e.g., with a microtome, to facilitate microscopic examination and observation of bound complex. Samples can also be fixed with an appropriate fixative either before or after incubation with one of the compounds or compositions of the present invention to improve the histological quality of sample tissues.

Time and conditions sufficient for binding of a complex of the present invention to a folate receptor on the cell include standard tissue culture conditions, i.e. samples can be cultured in vitro and incubated with one of the compounds or compositions of the present invention in physiological media. Such conditions are well known to the skilled person. Alternatively, samples can be fixed and then incubated with a complex or composition of the present invention in an isotonic or physiological buffer.

A typical amount of said complex of the present invention for in vitro detection of a tumor cell can range from about 1 ng/l to about 1000 µg/l. A preferred amount is about 1 µg/l to about 100 µg/l. Preferred compounds of the invention, wherein the imaging moiety is a chelated metal radionuclide $M_1$ to be used for in vitro diagnosis of a tumor cell are the same as for in vivo applications and include $^{99m}Tc$, $^{186/188}Re$, $^{111}In^{+3}$, $^{67/68}Ga^{+3}$, $^{90}Y^{+3}$, $^{109}Pd^{+2}$, $^{105}Rh^{+3}$, $^{177}Lu$, $^{64/67}Cu$, $^{161}Tb$, $^{213}Bi$, preferably $^{177}Lu$, $^{161}Tb$, $^{213}Bi$, or $^{111}In$.

Likewise, preferred compounds of the invention, wherein the imaging moiety is a non-metal radionuclide $M_2$ to be used for in vitro diagnosis of a tumor cell are the same as for in vivo applications and include $^{11}C$, $^{13}N$, $^{15}O$, $^{17}F$, $^{18}F$, $^{75}Br$, $^{76}Br$, $^{77}Br$, $^{123}I$, $^{124}I$, $^{131}I$, preferably $^{18}F$, $^{123}I$, $^{124}I$, $^{131}I$.

For detection of cellular binding of one of the present compounds, samples can be incubated in the presence of a selected compound, then washed and counted in a standard scintillation counter. Alternative methods apply and are known to the skilled person.

It is understood that the above methods of the invention may be performed in combination with any other methods of cancer diagnosis or therapy including methods using other already developed diagnostic and/or therapeutic agents and utilizing x-ray computed tomography (CT), magnetic resonance imaging (MRI), functional magnetic resonance imaging (fMRI), single photon emission computed tomography (SPECT), optical imaging, and ultrasound.

For diagnostic or radionuclide therapy applications it may be convenient to prepare the compounds of the present invention at, or near, the site where they are to be used. Thus for the compounds of the invention, wherein M is a chelated metal radionuclide $M_1$, the present invention provides in a further aspect a single or multi-vial kit containing all of the components needed to prepare those compounds or compositions of this invention, other than the radioimaging metal ion itself. Thus a preferred single-vial kit of the present invention comprises a compound of the present invention, wherein M is a chelated metal radionuclide $M_1$, and a source of a pharmaceutically acceptable reducing agent such as a stannous salt. In addition, the kit comprises optionally further additives, for example the kit is buffered with a pharmaceutically acceptable acid or base to adjust the pH to a desired value for complex formation. Such a single vial kit may optionally contain exchange ligands such as glucoheptonate, gluconate, mannitol, maleate, citric or tartaric acid and may also contain reaction modifiers, such as diethylenetriaminepentaacetic acid or ethylenediamine tetraacetic acid. Additional additives, such as solubilizers (for example a cyclodextrin), antioxidants (for example ascorbic acid) and/or fillers (for example, NaCl) may be employed to improve the radiochemical purity and stability of the final product, or to aid in the production of the kit. The radionuclide, e.g. Lu, Tb, Bi, or In, will preferably be added separately in the form of a solution.

Likewise, a preferred multi-vial kit of the present invention comprises, in one vial, the components, other than the radionuclide itself, required to form a labile radionuclide complex, that is, an exchange ligand and a pharmaceutically acceptable reducing agent such as a stannous salt. A compound of the present invention, wherein M is a chelated metal radionuclide $M_1$, is contained in a second vial, as well as optional additives such as buffers appropriate to adjust the pH to its optimal value. Optionally the radionuclide will be provided in form of a solution to be added.

All components of a kit may be in liquid, frozen or dry form. In a preferred embodiment, kit components are provided in lyophilized form.

All of the compounds, compositions and/or methods disclosed and claimed herein can be made and executed without undue experimentation in light of the present disclosure. It will be apparent to those of skill in the art that variations may be applied to the present invention without departing from the scope of the invention. The Examples provided herein are intended to be illustrative and are not exhaustive; therefore the illustrated Examples should not be viewed as limiting the invention in any way.

EXAMPLES

Materials and Methods

All chemicals were purchased from Sigma-Aldrich or Fluka, Buchs, Switzerland. All chemicals and solvents were of reagent grade and were used without further purification unless otherwise stated. The Boc-protected amino acids were purchased from Bachem AG, Bubendorf, Switzerland. The pteroic acid precursor was a kind gift from Merck Eprova AG, Schaffhausen, Switzerland and DOTA-azide and DOTA-NHS-Ester was received from Macrocyclics, Dallas, USA. [Na][$^{99m}$TcO$_4$] was eluted from a $^{99}$Mo/$^{99m}$Tc-generator (Mallinckrodt-Tyco, Petten, the Netherlands) with a 0.9% saline solution. $^{67}$GaCl$_3$ was received from Mallincrodt-Tyco, Petten, the Netherlands and $^{177}$LuCl$_3$ was received from Nuclear Research and Consultancy Group, NRG, Petten, the Netherlands.

Reactions were monitored by HPLC or by thin-layer chromatography (TLC) using precoated silica gel 60 F254 aluminium sheets (Merck), and visualized by UV absorption or stained with a solution of ninhydrin in EtOH (0.2 g in 100 ml). Column chromatography was performed using silica gel 60 (Fluka; particle size 0.04-0.063 mm). Analytical HPLC was performed using a Merck-Hitachi L-7000 system equipped with an L-7400 tunable absorption detector and an XBridge™ C-18 reverse phase column (5 µM, 4.6×150 mm, Waters). HPLC solvents were either water with 0.1% TFA (solvent A) and MeCN (solvent B), or 0.1% TFA in water (solvent A) and MeOH (solvent B) with a flow rate of 1 mL/min. The gradient was as follows: 0-15 min: gradient from 95% A to 20% A. Sep-PakR columns (Waters) were washed with methanol and water prior to use. Analytical radio-HPLC was performed on a Merck-Hitachi L-2130 system equipped with a L-2450 diode array detector and a Berthold radiodetector with a reversed-phase column (Gemini C18, 5 µm, 4.6×250 mm, Phenomenex) using 0.05 M NH$_4$HCO$_3$ (solvent A) and acetonitrile (solvent B) as solvent system with a gradient from 0-15 min 80% A, 15-20 min 80-30% A, 20-25 min 30% A and a flow rate of 1 mL/min. Semipreparative radio-HPLC was performed on a HPLC system equipped with a Smartline pump 1000, Smartline Manager 5000, a Smartline UV detector 2500 (Knauer) and a GabiStar radiodetector (Raytest) using a reversed-phase semipreparative column (Gemini C18, 5 µm, 250×10 mm, Phenomenex) at a flow rate of 4 mL/min with 0.05 M NH$_4$HCO$_3$ (solvent A) and acetonitrile (solvent B) as solvent system and a gradient as follows: 0-20 min 80% A, 20-25 min 80-30% A, 25-30 min 30% A.

Nuclear magnetic resonance spectra were recorded on a 400 MHz Bruker spectrometer. 1H and 13C chemical shifts were reported relative to residual solvent peaks or water as a reference. Values of the coupling constant J were given in Hertz (Hz). The following abbreviations are used for the description of $^1$H-NMR spectra: singlet (s), doublet (d), triplet (t), quartet (q), multiplet (m). The chemical shifts of complex multiplets are given as the range of their occurrence. Low resolution mass spectra were recorded with a Micromass Quattro Micro™ API LC-ESI using either the negative or positive ionization mode. High resolution mass spectra were recorded with a Bruker FTMS 4.7T BioAPEXII.

Cell culture: KB cells (human nasopharyngeal carcinoma cell line) were purchased from the American Type Culture Collection (CCL-17). JK24-FBP cells were a kind gift from Dr. Patrick Hwu (National Cancer Institute, Bethesda, Md.). The cells were cultured as monolayers at 37° C. in a humidified atmosphere containing 5% CO$_2$. Importantly, the cells were cultured in a special RPMI cell culture medium herein referred as FFRPMI (modified RPMI 1640 medium, without folic acid, vitamin B12, and phenol red; Cell Culture Technologies GmbH). FFRPMI medium was supplemented with 10% heat-inactivated fetal calf serum (FCS, as the only source of folate), L-glutamine, and antibiotic (penicillin 100 IU/ml, streptomycin 100 µg/ml, fungizone 0.25 µl/ml). Eighteen to twenty hours prior to each experiment, the cells were seeded in 12-well plates (7×10$^5$ cells/2 ml) to form confluent monolayers over night.

Uptake and internalization studies: Receptor binding studies were performed according to the following general procedure: The monolayers of the cells were rinsed with PBS pH 7.4. Pure FFRPMI medium (without FCS, L-glutamine, antibioticas, 975 µl) only, FFRPMI medium (475 µl) and a folic acid solution for receptor blocking studies (500 µl, 200 µM in medium) or FFRPMI medium containing 4% BSA were added into the corresponding wells. The well plates were pre-incubated at 37° C. for 15 min. Solutions of the 67Ga-labelled compounds 16 or 6 (25 µl, 1.5 MBq/ml) were added to each well. Plates were incubated at 37° C. for up to 4 h. Then, each well was rinsed twice with PBS buffer pH 7.4 or once with PBS pH 7.4 and once with an acidic stripping buffer (aqueous solution of 0.1 M acetic acid and 0.15 M NaCl), respectively, to remove bound complex from the FR on the cell surface. The monolayers were dissolved in 1 ml NaOH (1M) and transferred to 4 ml tubes. Samples as well as 4 standard-samples (25 µl labelled $^{67}$Ga-16 or $^{67}$Ga-6) were counted for radioactivity using a Cobra™ II γ-counter. The concentration of proteins was determined for each sample in order to normalize measured radioactivity of the samples with respect to the averaged sample protein content that accounted for 0.5 mg or 0.3 mg (as indicated under results) protein per well (Thermo Scientific Pierce BCA Protein Assay, Product #23225).

Albumin binding studies: Albumin binding studies using HPLC and a Superose™ 12 size exclusion column were performed according to the following general procedure: Compound 16 and 6 were radiolabelled according to the above described protocol. Samples of 1 MBq were injected onto the column, using 0.05% tweenR 20 in PBS pH 7.4 as eluent. The radioactive compounds $^{67}$Ga-16 and $^{67}$Ga-6 (12 µl, approximately 1 MBq) were incubated for 30 min at 37° C. with either HSA solution 20% (100 µl) or human plasma (100 µl). A volume of 100 µl of the incubated solution was injected on the Superose™ 12 size exclusion column. Elution of the plasma proteins and of the radiolabelled compound was monitored by HPLC in the UV trace (220 nm) and the radioactive γ-trace, respectively. Albumin binding studies using ultracentrifugation devises were performed according to the following general procedure83: The HPLC-purified radiolabelled compounds 16, 6, FA2, FA4 and 22 (2.5-3.0 66 MBq) were incubated for 10 min at 37° C. with 350 µl of human plasma or 350 µl of 1×PBS, pH 7.4. The samples were loaded onto the ultrafilter (CentrifreeR, Ultracel YMT devises from Millian, Geneva) and centrifugated for min at 2000 rpm. The filtrate (3×25 µl) and initially incubated solution (3×25 µl, standard) were counted for radioactivity using a Cobra™ II γ-counter. For standardization, the filtrate of the compounds in PBS was indicated being 100%. This 100% fraction was compared to the fraction of active compound found in the filtrate of the plasma sample and the activity of the plasma sample were expressed in % of the activity in the PBS filtrate.

In vitro autoradiography: The slides with mouse tissue sections (KB tumour xenographs and kidneys) were preincubated in Tris-HCl buffer (170 mM, pH 7.6, with 5 mM MgCl$_2$) with 0.25% (w/v) BSA for 10 min at room temperature. Then, the sections were incubated with a solution of $^{67}$Ga-16 and $^{67}$Ga-6 (0.5 MBq/ml in Tris-HCl buffer containing 1% BSA) for 60 min at room temperature. After incubation, the sections were rinsed twice for 5 min in cold Tris-HCl buffer (with 25% BSA), then washed for 5 min in pure TrisHCl buffer, and finally rinsed with cold distilled water. The sections were air-dried and exposed to phosphor imaging screens.

Example 1

Synthesis of Trifunctional Conjugate 16

(a)

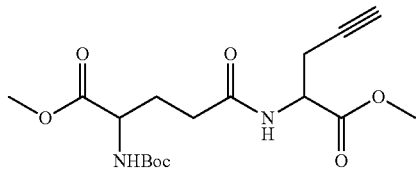

1

Boc-Glu-OMe (181.5 mg, 0.65 mmol) was dissolved in DMF (1.5 ml), HBTU (314.2 mg, 0.83 mmol, 1.2 eq.) and NEt$_3$ (2 eq.) were added. The solution was stirred at 0° C. for 1 h. The solution was added to H-Pra-OMe.HCl (120.2 mg, 0.74 mmol, 1.06 eq.) in DMF (2 ml) and NEt$_3$ (4 eq.). The suspension was stirred over night, 0° C.→RT. MeOH was added to dissolve remaining particles. The solution was stirred at 0° C. for 3 h. The product was extracted with citric acid (1 M) and ethyl acetate. The organic phase was rinsed with brine, dried over Na2SO4 and concentrated under reduced pressure. Purification was achieved by CC (SiO$_2$, MeOH/CH$_2$Cl$_2$ 1:50) to give a clear oil. 233 mg (0.63 mmol, 90%). LC-MS [M-C$_5$H$_7$O$_2$(Boc)]H+=270.87 (calc. for C$_{17}$H$_{26}$N$_2$O$_7$, 370.17). 1H-NMR (DMSO-d6) δ 8.3, 7.17, 4.36-3.31, 3.92-3.87, 3.57, 3.55, 3.24, 2.8, 2.52, 2.15, 1.87-1.79/1.72-1.62, 1.3 ppm.

(b)

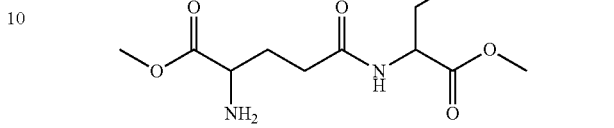

2

1 (233 mg, 0.63 mmol) was dissolved in TFA (10% in CH$_2$Cl$_2$). The solution was stirred at RT for 3 h. The solvent was evaporated under reduced pressure. Purification was achieved by CC (SiO$_2$, MeOH/CH$_2$Cl$_2$ 1:30) to give the TFA salt as a clear solid. 224 mg (0.58 mmol, 92%). LC-MS [M+H]+=270.84 (calc. for C$_{12}$H$_{18}$N$_2$O$_5$, 270.12). 1H-NMR (MeOH-d4) δ 7.98, 4.58, 4.10, 3.85, 3.74, 2.82, 2.71, 2.54, 2.19.

(c)

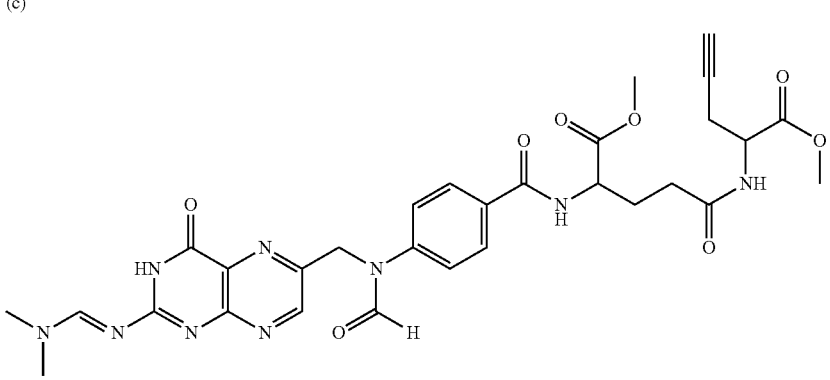

3

Pteroic acid (166.9 mg, 0.41 mmol, 1.04 eq.) was dissolved in DMF (3 ml). HBTU (208.9 mg, 0.55 mmol, 1.4 eq.) and NEt$_3$ (2 eq.) were added. The suspension was stirred at 0° C. for 1.5 h. The suspension was added to 2 (105.2 mg, 0.39 mmol, 1 eq.) in DMF (2 ml) and NEt$_3$ (2 eq.). The solution was stirred at 0° C. for 4 h. The solvent was evaporated under reduced pressure. Purification was achieved by CC (SiO$_2$, MeOH/CH$_2$Cl$_2$ 1:20) to give a yellow powder. 90 mg (0.14 mmol, 36%). LC-MS [M+H]+=647.93 (calc. for C$_{30}$H$_{33}$N$_9$O$_8$, 647.25).

(d)

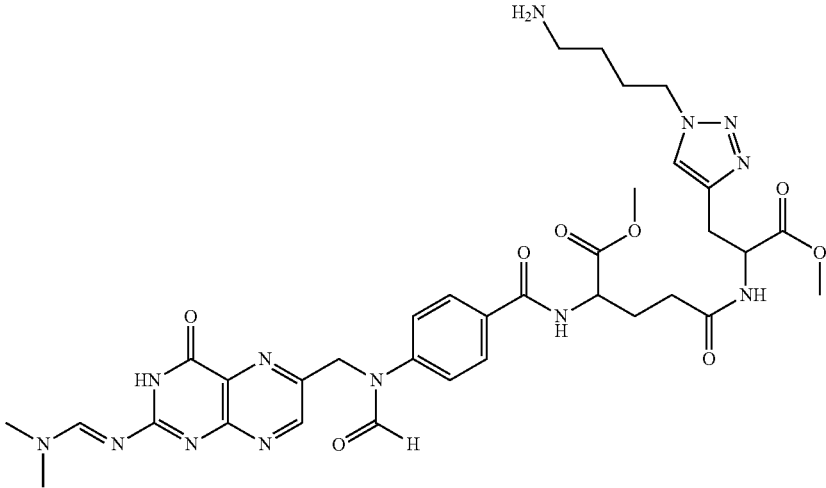

4

3 (22.88 mg, 35 pmol) and 4-azidobutyl-1-amine.TFA (27.7 mg, 0.12 mmol, 3.4 eq.) were mixed in 3:1 tBuOH/H$_2$O (1.1 ml). Cu(OAc)$_2$.H$_2$O (31 µl, from a 100 mM stem solution, 0.1 eq.) and Na ascorbate (1.5 mg, from a 100 mM stem solution, 0.2 eq.) were added drop wise. The solution was stirred at RT for several h. Some of the solvent was evaporated under reduced pressure. Purification was achieved by semi-preparative HPLC using 0.1% TFA in H$_2$O and acetonitrile as the eluent to give a yellow powder. 8.64 mg (11.3 pmol, 32%). LC-MS [M-C$_3$H$_7$N (dimethylformamide protecting group)]+= 706.95 (calc. for C$_{34}$H$_{43}$N$_{13}$O$_8$, 761.34).

(f)

(e)

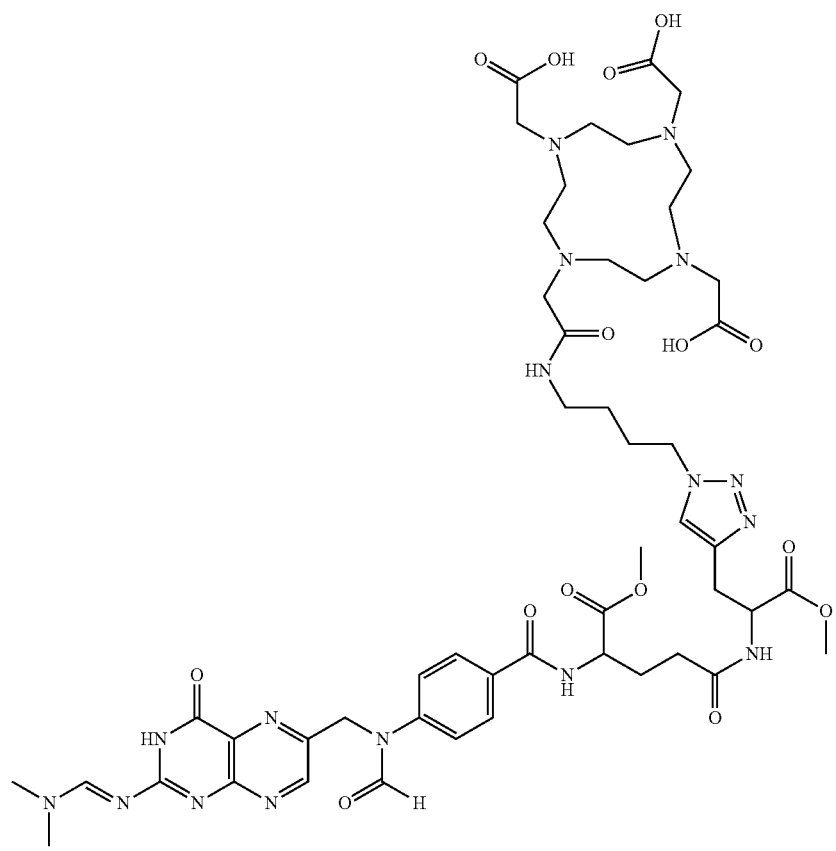

4 (8.64 mg, 11.3 pmol) and NHS-DOTA.PF$_6$ (8.05 mg, 12.4 pmol, 1.1 eq.) were dissolved in a mixture of DMF (0.4 ml) and DIPEA (4 eq.). The reaction was stirred at 40° C. for several h. The reaction was forced to completion by adding more NHS-DOTA PF$_6$. The solvent was removed under reduced pressure and the product was used without further purification. LC-MS [M-C$_3$H$_7$N (dimethylformamide protecting group]+=1093.02 (calc. for C$_{50}$H$_{69}$N$_{17}$O$_{15}$, 1147.52).

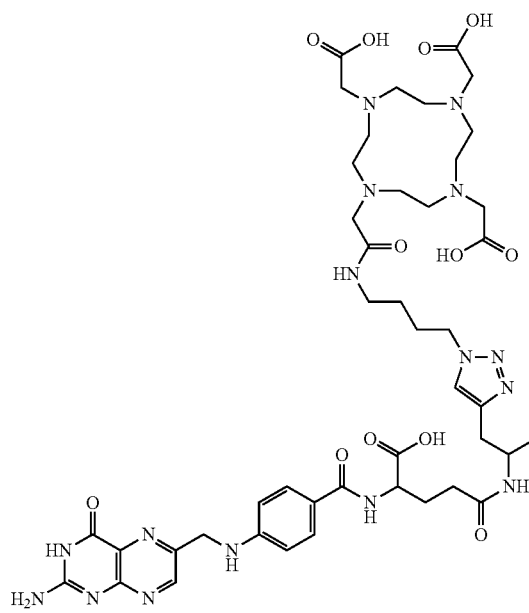

6

5 was dissolved in a 1:1 mixture of MeOH/H$_2$O and adjusted to pH 13 using NaOH (1M). The solution was stirred at RT for 2 h. The solvent was evaporated under reduced pressure. The resulting solid was redissolved in H$_2$O and the solution was neutralized using HCl (1M). Final purification was achieved by solid phase extraction using a reverse phase SepPak column with H$_2$O and increasing concentrations of MeOH as the eluent. Some of the solvent was evaporated under reduced pressure. The compound was lyophilized to give a bright yellow powder. 4.1 mg (3.95 pmol, 35%). LC-MS [M+Na]+=1059.44, (calc. for C$_{44}$H$_{60}$N$_{16}$O$_{14}$, 1036.45).

(g)

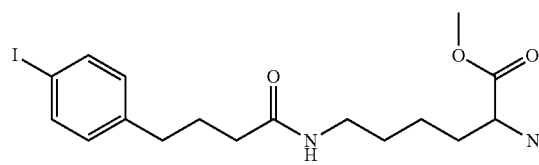

7

4-p-iodophenyl-butric acid (502 mg, 1.7 mmol, 1.07 eq.) was dissolved in DMF (1.5 ml) and NEt$_3$ (2 eq.). HBTU (751 mg, 1.98 mmol, 1.23 eq.) was added. The solution was stirred at 0° C. for 1 h. The solution was added drop wise to Boc-Lys-OMe (428 mg, 1.6 mmol) in DMF (1.5 ml) and NEt$_3$ (2 eq.). The solution was stirred at 0° C. for 4 h. The product was extracted with citric acid (1 M) and ethyl acetate/n-Hexane (9:1). The organic phase was rinsed with brine, dried over Na$_2$SO$_4$ and concentrated under reduced pressure. Purification was achieved by CC (SiO$_2$, MeOH/CH$_2$Cl$_2$ 1:50) to give a clear oil. 653.5 mg (1.23 mmol, 75%). LC-MS [M+H]+= 532.77 (calc. for C$_{22}$H$_{33}$IN$_2$O$_5$, 532.14). 1H-NMR (MeOH-d4) δ 7.59, 6.98, 4.09, 3.69, 3.15, 2.59, 2.29, 2.18, 1.88, 1.78/1.64, 1.51, 1.42 ppm.

(h)

8

7 (568.5 mg, 1.07 mmol) was deprotected with TFA 10% in CH$_2$Cl$_2$ at RT for 2 h. The solvent was evaporated under reduced pressure. Purification was achieved by CC (SiO$_2$, MeOH/CH$_2$Cl$_2$ 1:30) to give the TFA salt as a slightly yellow tar. 478.9 mg (0.88 mmol, 82%). LC-MS [M+H]+=432.94, (calc. for C$_{17}$H$_{25}$IN$_2$O$_3$, 432.09). 1H-NMR (MeOH-d4) δ 7.60, 6.99, 3.96, 3.80, 3.17, 2.58, 2.19, 1.88, 1.53, 1.4 ppm.

(i)

9

Boc-Pra-OH (50.7 mg, 0.24 mmol, 1.06 eq.) was dissolved in DMF (1 ml) and NEt$_3$ (1.8 eq.). HBTU (101.4 mg, 0.27 mmol, 1.2 eq.) was added. The solution was stirred at 0° C. for 1 h. The solution was added drop wise to 8•TFA (122.6 mg, 0.224 mmol) in DMF (1.5 ml) and NEt$_3$ (1.8 eq.). The solution was stirred at 0° C. for 4 h. The solvent was evaporated under reduced pressure. Purification was achieved by CC (SiO$_2$, first CH$_2$Cl$_2$, then MeOH/CH$_2$Cl$_2$ 1:50) to give a yellow oil. 125 mg (0.2 mmol, 89%). LC-MS [M+H]+=627.86 (calc. for C$_{27}$H$_{38}$IN$_3$O$_6$, 627.18). 1H-NMR (MeOH-d4) δ 7.98, 6.99, 4.42, 4.25, 3.69, 3.15, 2.68/2.63, 2.58, 2.38, 2.18, 1.87, 1.72, 1.45, 1.45 ppm.

(j)

10

9 (122.2 mg, 0.195 mmol) was deprotected with 10% TFA in CH$_2$Cl$_2$ (10 ml). The solvent was evaporated under reduced pressure. Purification was achieved by CC (SiO$_2$, first MeOH/CH$_2$Cl$_2$ 1:30, than MeOH/CH$_2$Cl$_2$ 1:20) to give the TFA salt as a yellow oil. 92.5 mg (0.144 mmol, 74%). LC-MS [M+H]+= 527.87 (calc. for C$_{22}$H$_{30}$IN$_3$O$_4$, 527.13). 1H-NMR (MeOH-d4) δ 7.6, 6.99, 4.45, 3.7, 3.59, 3.15 2.59, 2.44 1.28, 1.88, 1.76, 1.51, 1.41 ppm.

(k)

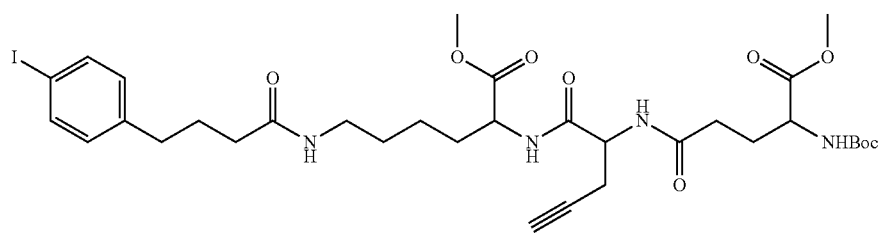

11

Boc-Glu-OMe (38.9 mg, 0.149 mmol, 1.01 eq.) was dissolved in DMF (1 ml) and NEt$_3$ (2 eq.). HBTU (60.2 mg, 0.159 mmol, 1.08 eq.) was added. The solution was stirred at 0° C. for 1 h. The solution was added to 10•TFA (90 mg, 0.147 mmol) in DMF (1.5 ml) and NEt$_3$ (2 eq.). The reaction was stirred at 0° C. for 3 h and stored 48 h at 5° C. The solvent was evaporated under reduced pressure. Purification was achieved by CC (SiO2, MeOH/CH$_2$Cl$_2$ 1:20) to give a clear oil. 53.9 mg (0.07 mmol, 48%). LC-MS [M+H]+=771.02 (calc. for C$_{33}$H$_{471}$N$_4$O$_9$, 770.24). 1H-NMR (CDCl$_3$/MeOH-d4) δ 7.55, 7.45, 6.92, 4.49, 4.42, 4.17, 3.70, 3.68, 3.12, 2.63, 2.55, 2.14, 1.84, 1.68, 1.45, 1.40, 1.32 ppm.

(l)

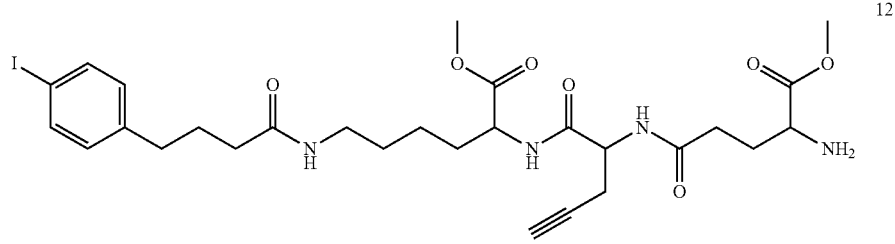

12

11 (319 mg, 0.414 mmol) was deprotected with 10% TFA in CH$_2$Cl$_2$ (10 ml). The solvent was evaporated under reduced pressure. Purification was achieved by CC (SiO$_2$, first CH$_2$Cl$_2$, then MeOH/CH$_2$Cl$_2$ 1:20) to give the multiple TFA salt as a clear oil. 331.5 mg. LC-MS [M+H]+=670.96 (calc. for C$_{28}$H$_{39}$IN$_4$O$_7$, 670.19). 1H-NMR (MeOH-d4) δ 7.6, 6.99, 4.58-4.50, 4.4, 3.86, 3.79, 3.69, 3.20-3.09, 2.73-2.62, 2.47, 2.43-2.41, 2.18, 2.14-2-0, 1.93-1.81, 1.76-1.67, 1.53-1.46, 1.43-1.34, 1.33-1.25, 1.18 ppm.

(m)

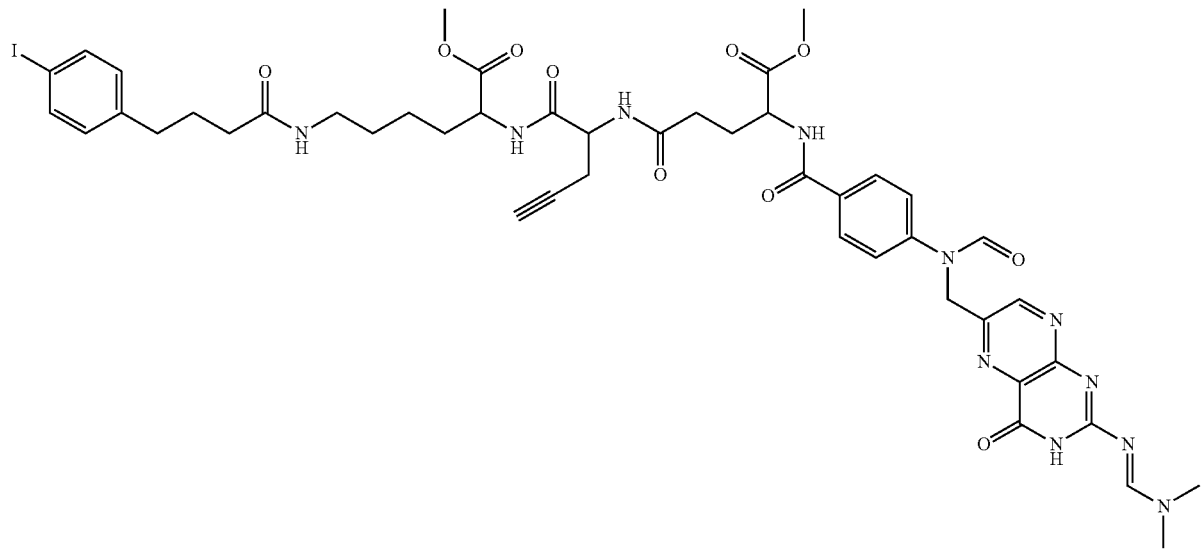

13

Pteroic acid (167.6 mg, 0.41 mmol, 1.05 eq.) was dissolved in DMF (1 ml) and NEt$_3$ (2 eq.). HBTU (177.9 mg, 0.47 mmol, 1.2 eq.) was added. The solution was stirred at 0° C. for 1 h. The solution was added to 12•TFA (305.5 mg, 0.39 mmol, 1.0 eq.) in DMF (1.5 ml) and NEt$_3$ (2 eq.). The reaction was stirred at 0° C. for 4 h. The solvent was evaporated under reduced pressure. Purification was achieved by CC (SiO$_2$, first CH$_2$Cl$_2$, then MeOH/CH$_2$Cl$_2$ 1:10) to give a yellow solid. 178.4 mg (0.17 mmol, 44%).

(n)

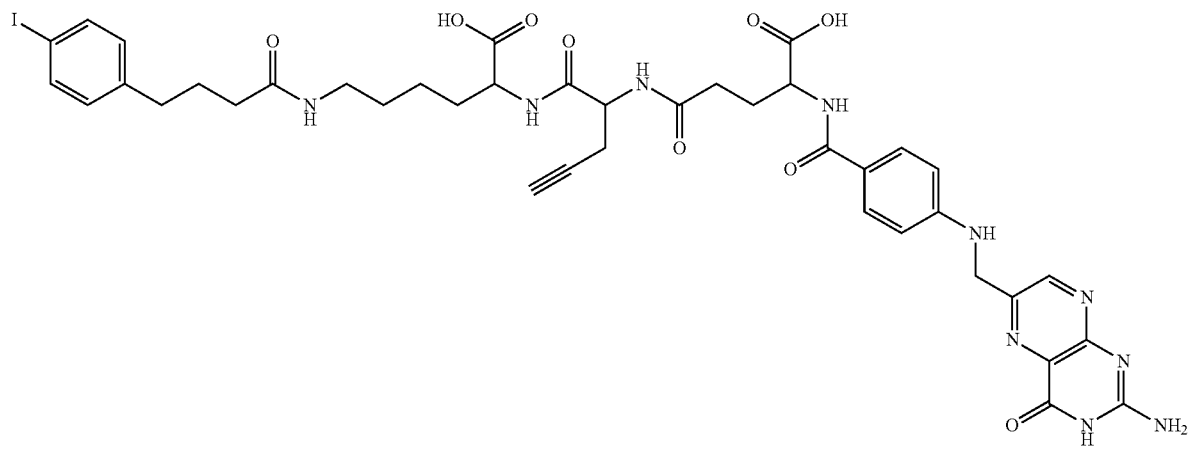

14

13 (178.4 mg, 0.17 mmol) was deprotected in MeOH/NaOH (aq.) pH 12.8 (10 ml) over night at RT. Purification was achieved by solid phase extraction using a reverse phase SepPak column, elution with H$_2$O and increasing amounts of MeOH and NaOH (aq.). 211.36 mg (0.23 mmol). LC-MS [M+H]+=936.93 (calc. for C$_{40}$HtIN$_{10}$O$_9$, 936.24).

(o)

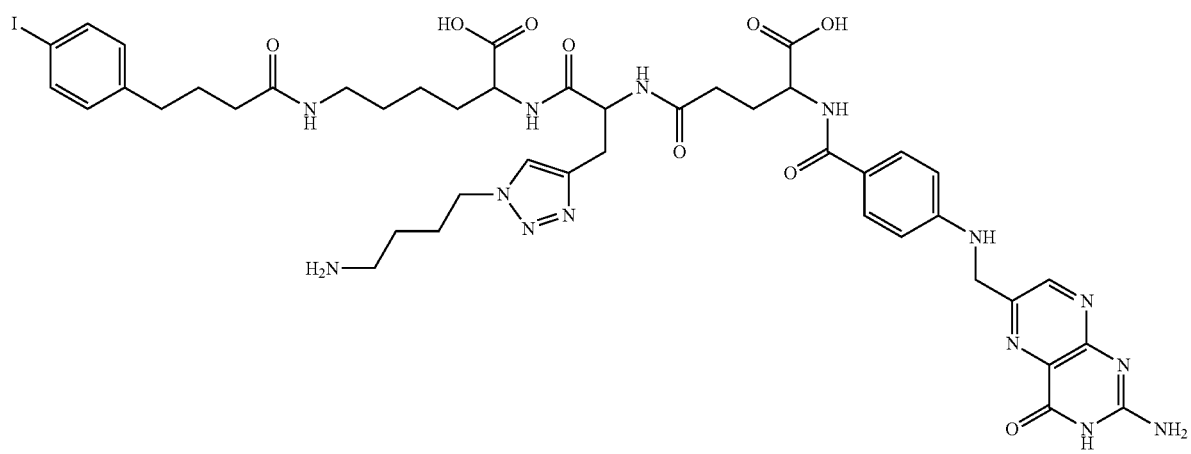

15

14 (21.9 mg, 23.4 pmol) and 4-azidobutyl-1-amine.TFA (5.24 mg, 4.7 pmol, 2 eq.) were mixed in 1:1 tBuOH/H$_2$O (1.2 ml). Cu(OAc)$_2$.H$_2$O (0.43 mg, from a 100 mM stem solution, 0.1 eq.) and Na ascorbate (0.93 mg, from a 100 mM stem solution, 0.2 eq.) were added drop wise. The solution was stirred over night at RT and at 50° C. for some h. The solvent was evaporated under reduced pressure. Purification was achieved by solid phase extraction using a reverse phase SepPak column, elution with H$_2$O, slightly basic EDTA and increasing concentrations of MeOH and NaOH (aq.). 10.58 mg (10.1 pmol, 43%). LC-MS [M+H]+=1050.95 (calc. for C$_{44}$H$_{551}$N$_{14}$O$_9$, 1050.33).

(p)

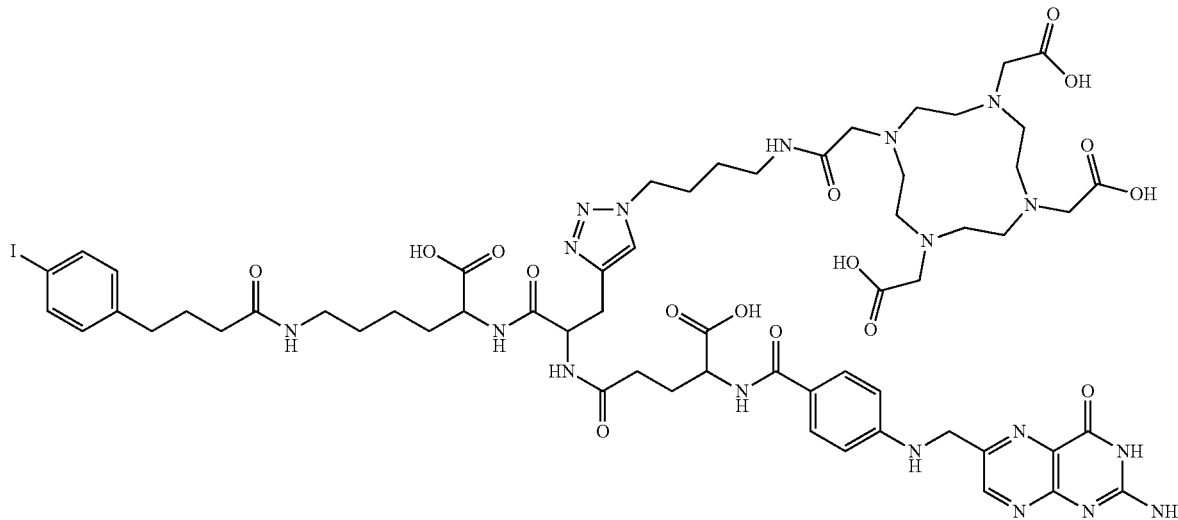

16

15 (10.58 mg, 10.1 pmol) and NHS-DOTA.PF$_6$ (9.7 mg, 15.0 pmol, 1.5 eq.) were dissolved in DMF (1 ml) and DIPEA (2.03 eq.). The reaction was stirred at 40° C. for several h. The solvent was removed under reduced pressure. The solid was redissolved in basic water and precipitated in acid. The precipitate was centrifuged and dried under high vacuum to give a yellow powder. 6.7 mg (4.7 pmol, 46%). LC-MS [M+H]+= 1437.76 (calc. for $C_{60}H_{81}1N_{18}O_{16}$, 1436.51).

CH$_2$Cl$_2$, then MeOH/CH$_2$Cl$_2$ 1:50) to give a clear oil. 164.1 mg (0.55 mmol, 56%). LC-MS [M+H]+=298.89 (calc. for $C_{15}H_{26}N_2O_4$, 298.19). 1H-NMR (CDCl$_3$-d) δ 7.97, 3.68, 3.38-3.36, 3.35-3.33, 3.05, 2.17, 1.81, 1.72-1.53, 1.48-1.28, 1.39 ppm.

(a)

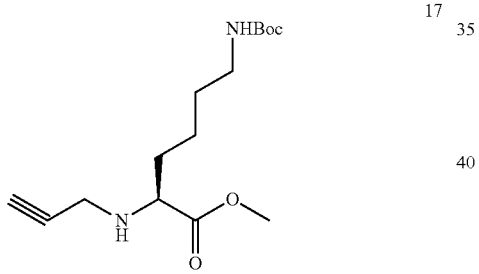

17

H-Lys-(Boc)OMe.HCl (291.9 mg, 0.98 mmol), 3-Bromo-1-propyne (80% in Toluene, 110.85 μl, 1.16 mmol, 1.2 eq.) and Cs$_2$CO$_3$ (643 mg, 2.0 mmol, 2.05 eq.) were stirred in DMF (4.5 ml) at RT and 60° C. for several h. The suspension was filtered and the solvent was evaporated under reduced pressure. Purification was achieved by CC (SiO$_2$, first pure

18

17 (164.1 mg, 0.55 mmol) was deprotected in 10% TFA in CH$_2$Cl$_2$ at RT for 3 h. Purification was achieved by solid phase extraction using a reverse phase SepPak column with H$_2$O as eluent to give a clear oil. 144 mg (0.46 mmol, 84%). LC-MS [M+H]+=198.92 (calc. for $C_{10}H_{18}N_2O_2$, 198.14).

Example 2

Synthesis of Trifunctional DOTA-Lys-Conjugate 26

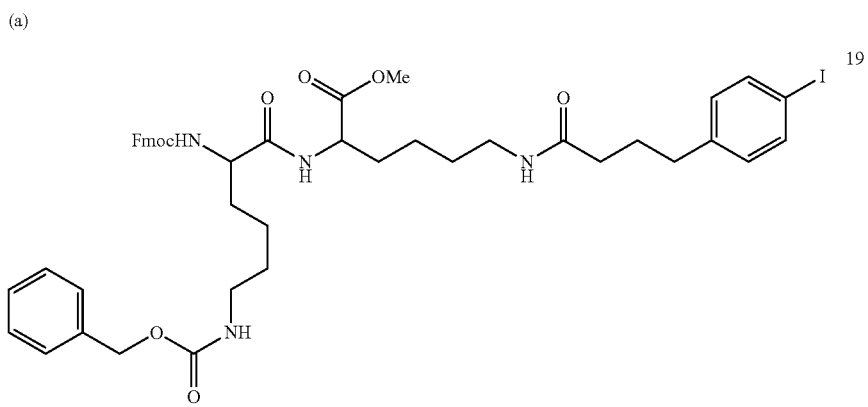

19

To 5 g of Fmoc-Lys(Z)—OH (Z=benzyloxycarbonyl) in 50 ml abs. DMF were added 2.2 ml triethylamine and 4.1 g HBTU (N,N,N',N'-tetramethyl-O-(1H-benzotriazol-1-yl)-uronium-hexafluoro-phosphate). The mixture was stirred for 15 min. at 25° C. Then a mixture of 4.9 g of compound 8 and 2.2 ml triethylamine in 50 ml DMF was added. After stirring for 20 hours, the solvent was removed in vacuum and the residue was dissolved in 50 ml methylene chloride. The methylene chloride solution was washed twice with 30 ml 5% aqueous citric acid solution, twice with 30 ml aqueous 5% sodium bicarbonate solution and twice with 30 ml of water. The organic layer was dried over magnesium sulphate and then evaporated to dryness to give 8.4 g of a waxy residue which was purified by chromatography on silica gel using CH$_2$Cl$_2$/MeOH 95:5 as eluent to give 7.3 g of pure 19.

(b)

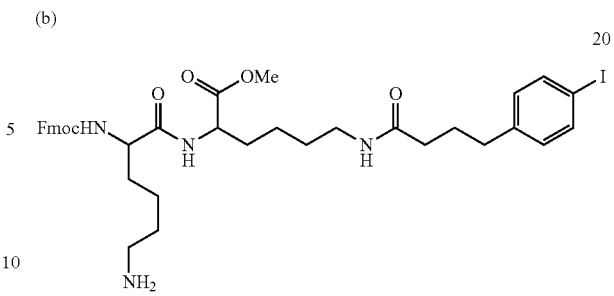

5 g of compound 19 were dissolved in 100 ml of methanol and 200 mg of Pd/C were added. The mixture was hydrogenated at 25° C. using 3 bar hydrogen for 24 hours. Solids were removed by filtration and the filtrate was evaporated to dryness to give compound 20.

(c)

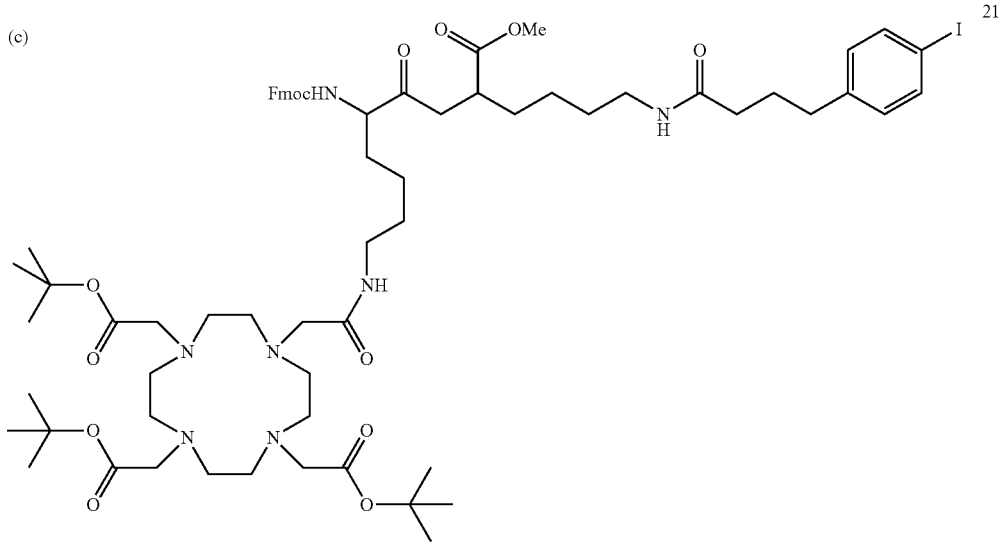

Compound 20 (1 equivalent) was dissolved in CH$_2$Cl$_2$ and an equimolar amount of DOTA-NHS-ester (purchased from Macrocyclics) was added. The mixture was stirred for 20 hours at 25° C. The solvent was evaporated and the residue was purified by chromatography on silica gel to give pure 21.

(d)

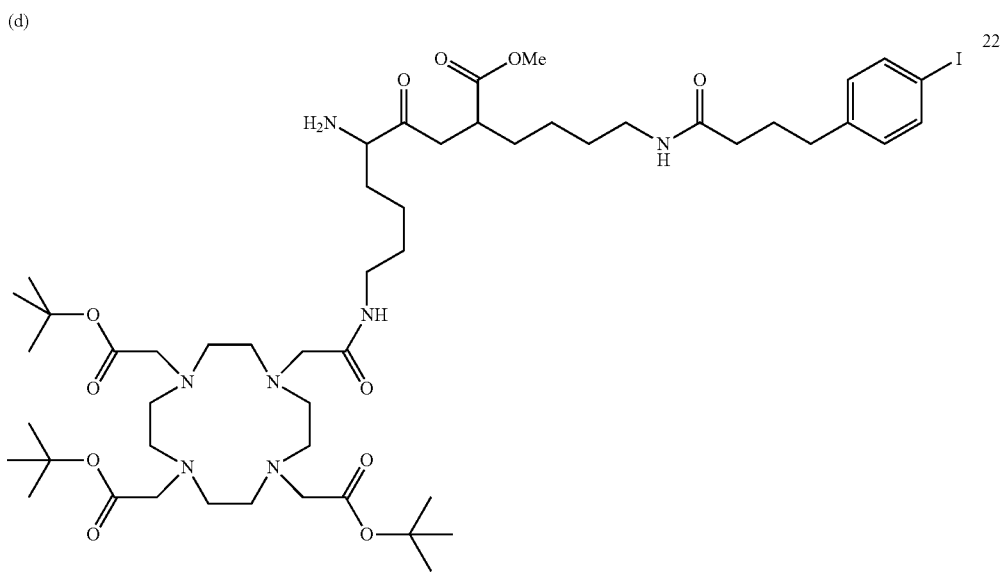

Compound 21 (1 equivalent) was dissolved in $CH_2Cl_2$. After addition of 30 equivalents of diethylamine the mixture was stirred for 20 hours. After evaporation to dryness the residue was purified by chromatography on silica gel to give pure 22.

(e)

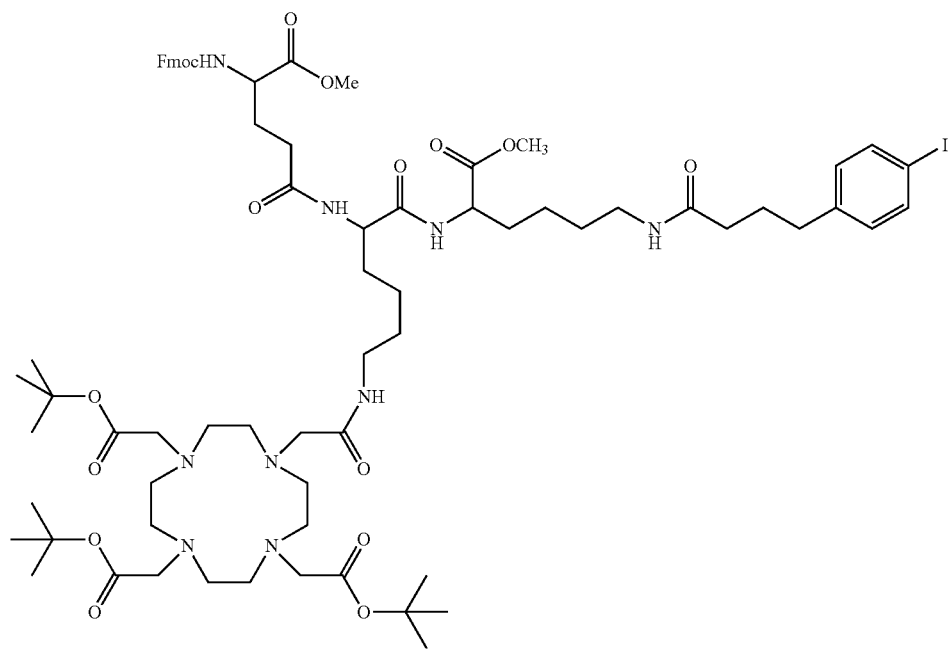

23

Fmoc-Glu-OMe (1 equivalent) was dissolved in abs. DMF. After addition of 2 equivalents of diisopropylethylamine and 1.1 equivalents of HBTU (N,N,N',N'-tetramethyl-O-(1H-benzotriazol-1-yl)-uronium-hexafluoro-phosphate) the mixture was stirred for 15 min. at 25° C. Then a solution of 1 equivalent of compound 22 in DMF was added and the mixture was stirred for 20 hours. The solvent was removed in vacuum and the residue was dissolved in methylene chloride. The methylene chloride solution was washed twice with 5% aqueous citric acid solution, twice with aqueous 5% sodium bicarbonate solution and twice with water. The organic layer was dried over magnesium sulphate and then evaporated to dryness to give a residue, which was purified by chromatography on silica gel to give pure 23.

(f)

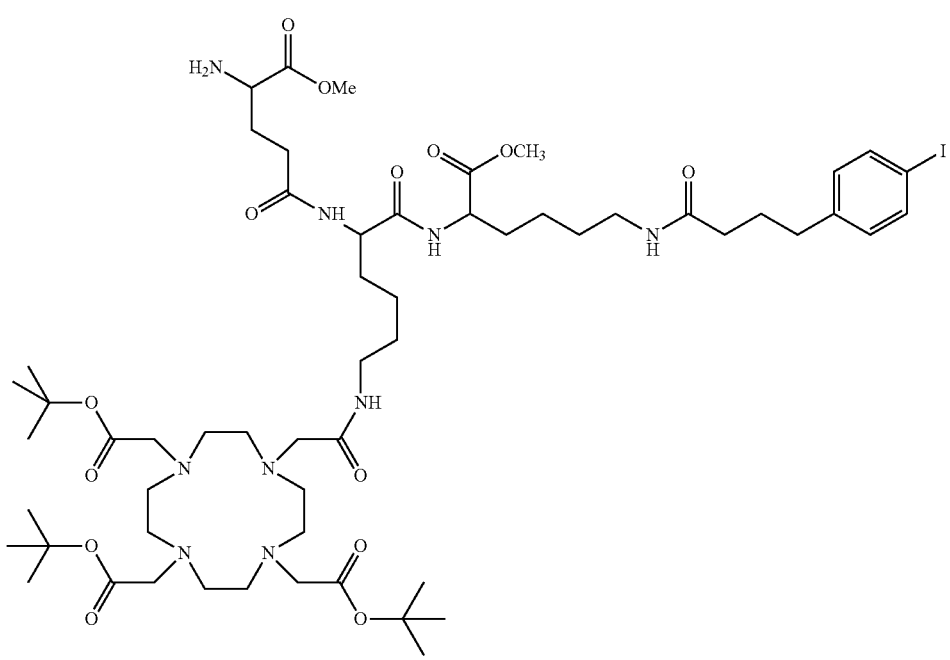

24

Compound 23 (1 equivalent) was dissolved in $CH_2Cl_2$. After addition of 30 equivalents of diethylamine the mixture was stirred for 20 hours. After evaporation to dryness the residue was purified by chromatography on silica gel to give pure 24.

(g)

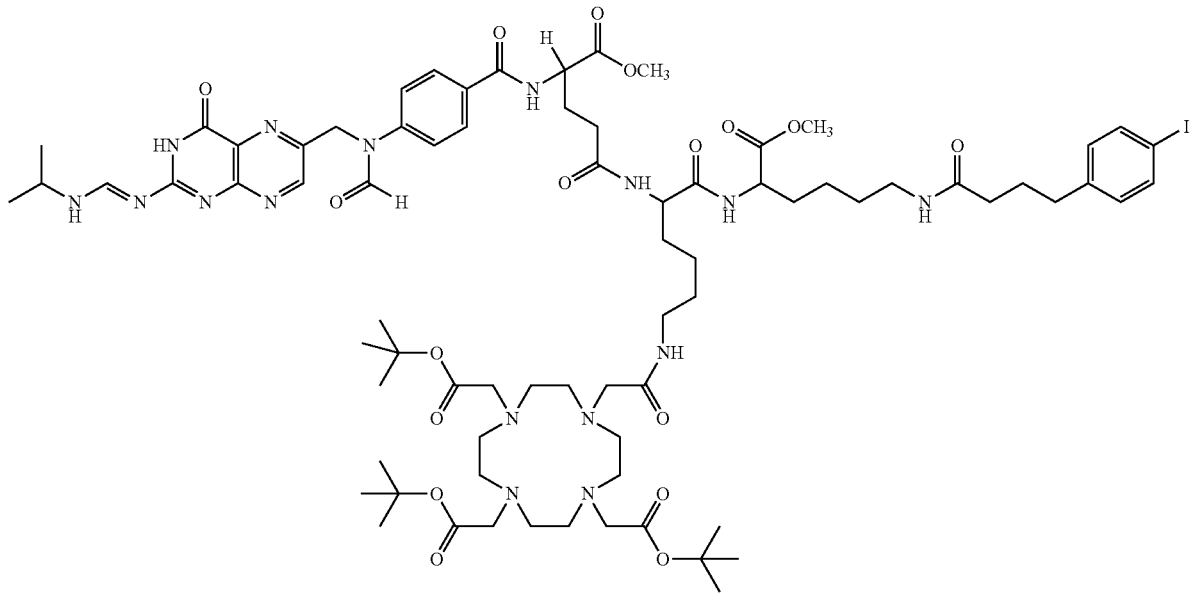

25

$N^2$—(N,N-dimethylaminomethylene)-10-formylpteroic acid (1 equivalent) was dissolved in abs. DMF. 2 Equivalents of triethylamine and 1.2 equivalents of HBTU (N,N,N',N'-tetramethyl-O-(1H-benzotriazol-1-yl)-uronium-hexafluorophosphate) were added and the mixture was stirred for 30 min. Then a solution of compound 24 in abs. DMF was added and the mixture was stirred for 20 hours at 25° C. After removal of solvent in vacuum the residue was dissolved in methylene chloride. The methylene chloride solution was washed twice with 5% aqueous citric acid solution, twice with aqueous 5% sodium bicarbonate solution and twice with water. The organic layer was dried over magnesium sulphate and then evaporated to dryness to give a residue, which was purified by chromatography on silica gel to give pure 25.

(h)

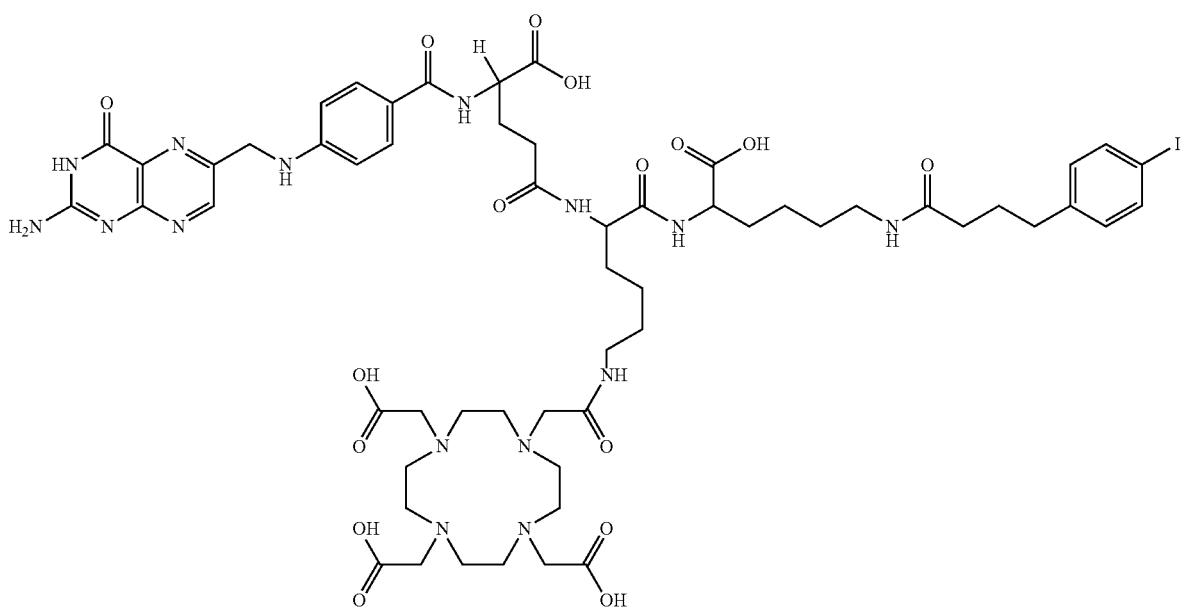

26

Compound 25 (1 equivalent) was dissolved in tetrahydrofuran and an aqueous solution of lithium hydroxide (3 equivalents) in water was added. After 4 hours at 25° C. the mixture was acidified to pH=1 by addition of aqueous hydrochloric acid. After heating to 50° C. for 2 hours the mixture was cooled to 25° C. and the precipitated product was isolated by centrifugation.

Example 3

Alternative Synthesis of Trifunctional DOTA-Lys-Conjugate 26

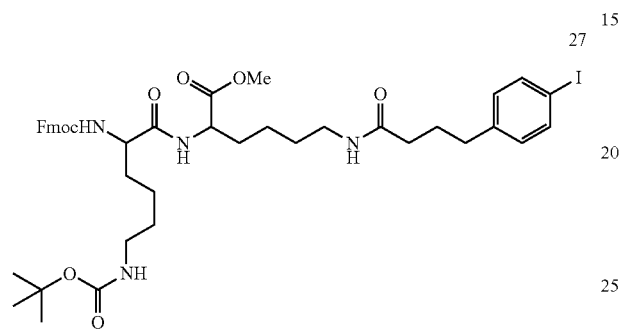

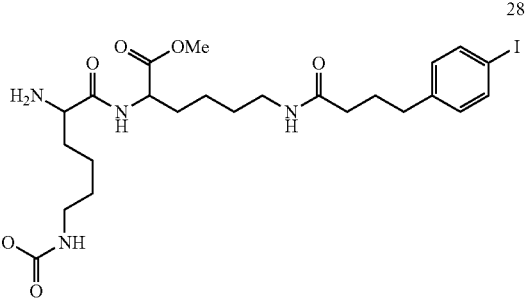

To compound 27 (7.2 g crude product) in dry methylene chloride (36 ml) was added diethylamine (36 ml). The mixture was stirred 2 hours at room temperature and then evaporated to dryness in vacuum at 40° C. Then a mixture of methylene chloride/methanol 90:10 (50 ml) was added to the residue and solids were removed. The filtrate was evaporated to dryness and the residue was purified by column chromatography using $SiO_2$ (70 g) and methylene chloride/methanol 90:10 as eluent to give compound 28 (4.1 g, 76% yield) as a white solid ($SiO_2$, $R_f$=0.34 ($CH_2Cl_2$/MeOH/90:10).

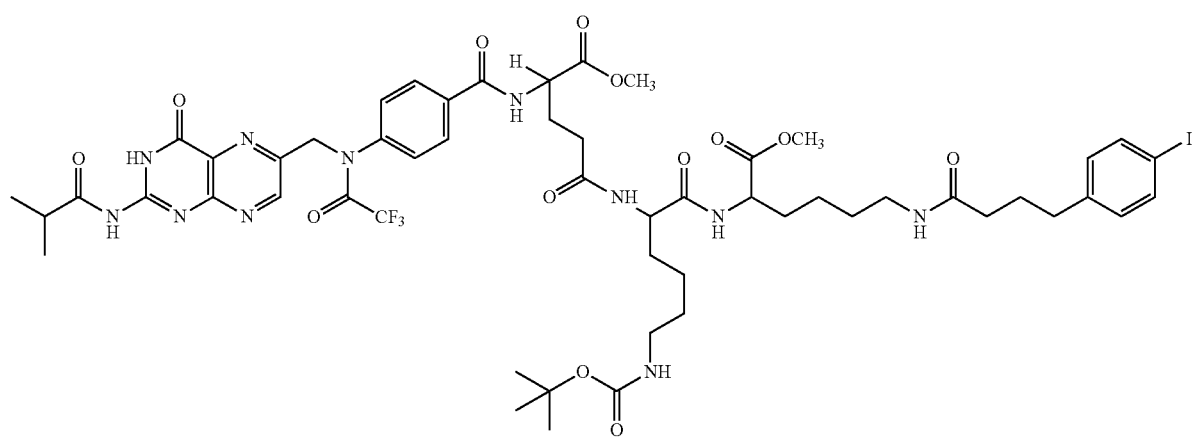

Fmoc-Lys(Boc)-OH (6.4 g, 13.7 mmol) was dissolved in dry N,N-dimethylformamide (53 ml). After addition of triethylamine (3.75 ml) and HBTU (N,N,N',N'-tetramethyl-O-(1H-benzotriazol-1-yl)-uronium-hexafluoro-phosphate, 5.2 g) the solution was stirred at room temperature for 15 min. A mixture of compound 8 (6.4 g, 13.7 mmol) in dry N,N-dimethylformamide (64 ml) and triethylamine (3.75 ml) was added. The reaction mixture was stirred for 17 hours at room temperature. Then the solids were drawn off and the filtrate was evaporated in vacuum at 40° C. to give an oily residue. The residue was dissolved in methylene chloride (100 ml) and washed with 5% aqueous citric acid (3×50 ml), with 5% aqueous sodium hydrogen carbonate (3×50 ml) and water (50 ml). The organic layer was dried over magnesium sulphate and evaporated to dryness in vacuum at 40° C. to give compound 27 (7.2 g, 60% yield) which was used without further purification for the synthesis of compound 28.

To a solution of $N^2$-isobutyryl-10-trifluoroacetyl-folic acid-α-methylester (3.4 g, 5.54 mmol, prepared according to WO 2009/082606) in dry N,N-dimethylformamide (34 ml) was added triethylamine (1.5 ml) and HBTU (N,N,N',N'-tetramethyl-O-(1H-benzotriazol-1-yl)-uronium-hexafluoro-phosphate, 2.1 g) and the mixture was stirred for 10 min. at room temperature. Then a solution of compound 28 (3.8 g, 5.8 mmol) in dry N,N-dimethylformamide (38 ml) was added and the mixture was stirred for 20 hours at room temperature. The reaction mixture was evaporated to dryness in vacuum at 40° C. The residue was dissolved in methylene chloride (128 ml) and washed with 5% aqueous citric acid (50 ml), with 5% aqueous sodium hydrogen carbonate (50 ml) and water (50 ml). The organic layer was dried over magnesium sulphate and evaporated to dryness in vacuum at 40° C. to give an off-white foam (7.2 g) which was purified by column chromatography using $SiO_2$ (210 g) and methylene chloride/ methanol 93:7 as eluent to give an off-white foam, which was purified a second time by column chromatography using SiO$_2$ (250 g) and methylene chloride/methanol 95:5 as eluent to give compound 29 (3.7 g, 53% yield) as an off-white foam, R$_f$=0.33 (SiO$_2$, CH$_2$Cl$_2$/MeOH/90:10).

for 5 min. at room temperature a solution of compound 30 (500 mg, 0.39 mmol) in dry N,N-dimethylformamide (5 ml) and triethylamine (54.2 µl) was added. The reaction mixture was stirred for 20 hours at room temperature and then evaporated to dryness in vacuum at 40° C. The residue was dis-

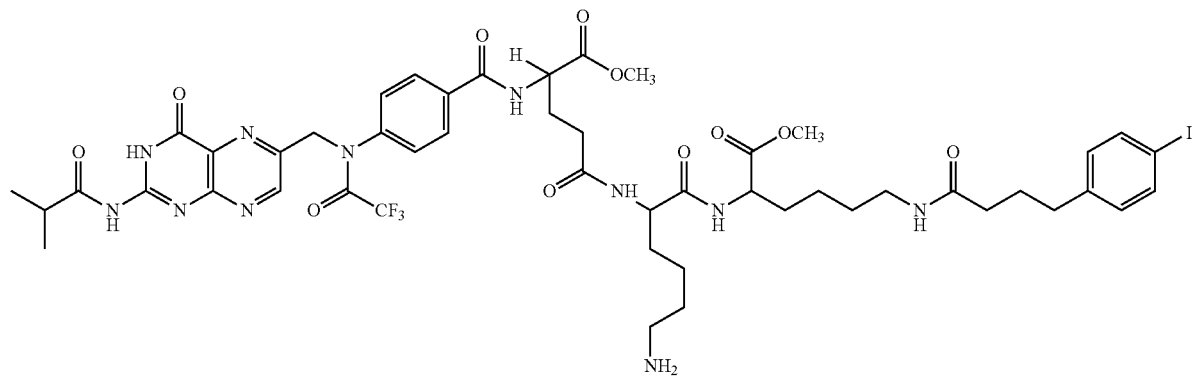

30

To a solution of compound 29 (3.5 g, mmol) in methylene chloride (88 ml) was added trifluoroacetic acid (8.8 ml) and triisopropylsilane (0.88 ml). The mixture was stirred at room temperature for 30 min. and then evaporated to dryness in vacuum at 40° C. The residue was purified by column chromatography using SiO$_2$ (235 g) and methylene chloride/methanol 90:10 as eluent to give compound 30 as an off-white foam (2.8 g, 79% yield), R$_f$=0.16 (SiO$_2$, CH$_2$Cl$_2$/MeOH/90:10).

solved in methylene chloride (25 ml) and washed with 5% aqueous citric acid (2×5 ml), with 5% aqueous sodium hydrogen carbonate (2×5 ml) and water (2×5 ml). The organic layer was dried over magnesium sulphate and evaporated to dryness in vacuum at 40° C. to give a yellow foam (0.5 g) which was purified by column chromatography using SiO$_2$ (17 g) and methylene chloride/methanol 93:7 as eluent to give compound 31 as an off-white foam (0.43 g, 64% yield), R$_f$=0.45 (SiO$_2$, CH$_2$Cl$_2$/MeOH/90:10).

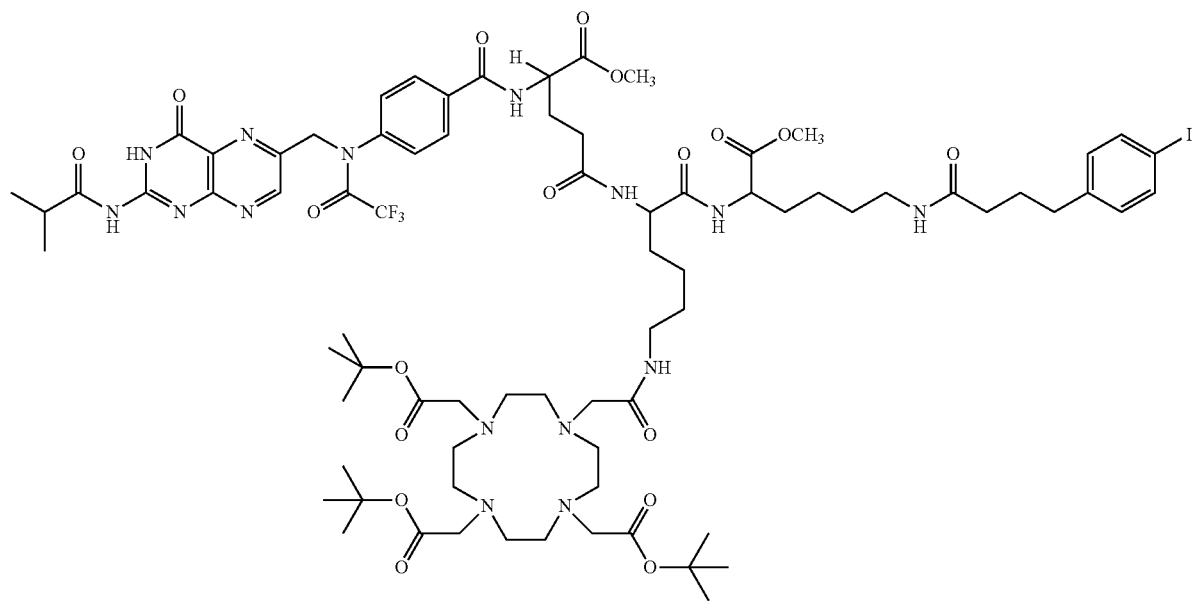

31

To a solution of DOTA-tris (tBu)ester (224 mg, 0.39 mmol, purchased from Macrocyclics, No. B-260) in dry N,N-dimethylformamide (12.5 ml) was added HBTU (N,N,N',N'-tetramethyl-O-(1H-benzotriazol-1-yl)-uronium-hexafluorophosphate, 148 mg) and triethylamine (54.2 µl). After stirring Compound 26 was obtained from compound 31 according to the following procedure: To a solution of compound 31 (0.43 g, 0.25 mmol) in methylene chloride (20 ml) was added trifluoroacetic acid (20 ml) and the resulting solution was stirred for 20 hours at room temperature. The reaction mixture was evaporated to dryness in vacuum at 40° C. and the residue was dissolved in tetrahydrofurane (20 ml). Then a solution of lithium hydroxide (120 mg) in water (20 ml) was added and the reaction mixture was stirred for 20 hours. The tetrahydrofurane was removed under reduced pressure at 40° C. and to the residual aqueous solution was added aqueous 1M hydrochloric acid (2.6 ml) until pH=3. The precipitated product was isolated by centrifugation (5000 rounds per min.) and washed with water (4×3 ml). The product was dried at 40° C. in vacuum for 48 hours to give compound 26 as an orange-yellow solid (279 mg, 82% yield). HPLC: 97.0% area. (5.9 mg product were dissolved in 5 ml water and 3 drops buffer (4 g Na2CO3 and 4 g KHCO3 dissolved in 200 ml water), Injection volume: 2 μl, column: Phenomenex, XB-C18, 75×4.6 mm, 2.6 μm, eluent A: 0.1% trifluoroacetic acid in water, eluent B: 0.1% trifluoroacetic acid acetonitrile in water/90:10, flow: 2.0 ml/min., pressure: 230 bar, gradient: in 20 min. from 0% eluent B to 100% eluent B. UV-detector, wavelength 230 nm.). LC-MS: [M+H]+=1356.8 (calc. for $C_{57}H_{78}IN_{18}O_{16}$, 1355.5).

Example 4

Synthesis of Trifunctional DOTA-Lys-α-Conjugate 32

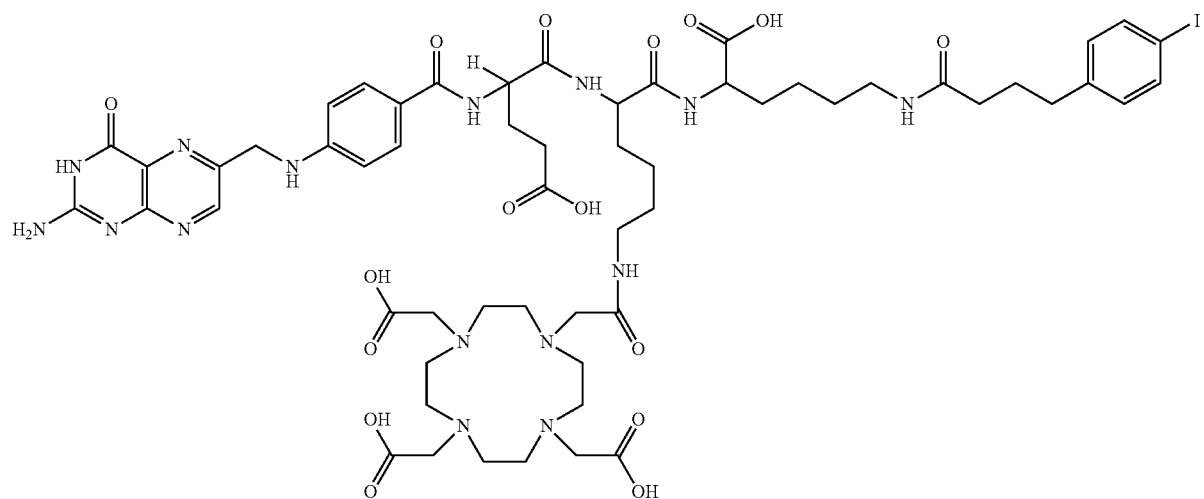

The synthesis was achieved in analogy to example 4 using $N^2$-isobutyryl-10-trifluoroacetyl-folic acid-7-methylester instead of $N^2$-isobutyryl-10-trifluoroacetyl-folic acid-α-methylester (the $N^2$-isobutyryl-10-trifluoroacetyl-folic acid-7-methylester was prepared in analogy to the $N^2$-isobutyryl-10-trifluoroacetyl-folic acid-α-methylester according to WO 2009/082606.)

Compound 32 was obtained as an orange-yellow solid. HPLC: 95.0% area (same method as described for analysis of compound 26). LC-MS: [M+H]+=1356.6 (calc. for $C_{57}H_{78}IN_{18}O_{16}$, 1355.5).

Example 5
Synthesis of Trifunctional Conjugate
[$^{18}$F]FDG-AB-Folate 34

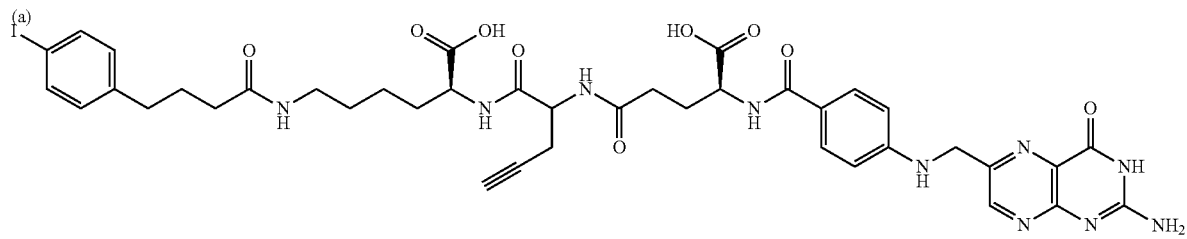

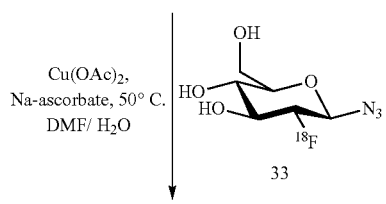

-continued

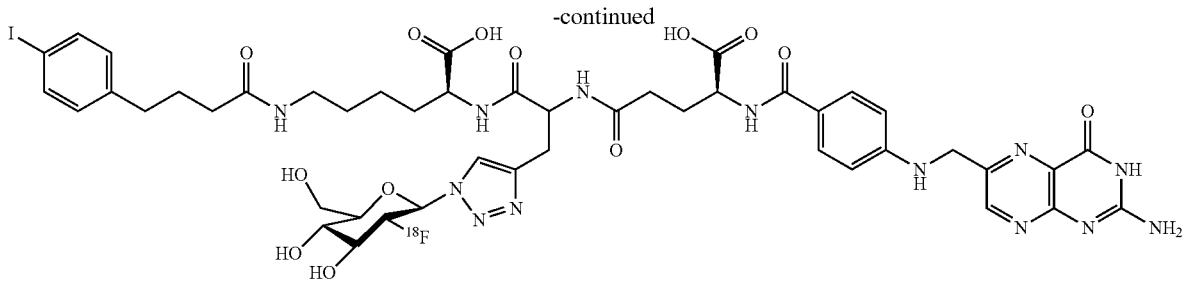

34

The 3,4,6-tri-O-acetyl-2-O-trifluoromethanesulfonyl-β-D-mannopyranosyl azide precursor used for coupling the $^{18}$F-substituted glucose via click reaction to the folate, was obtained according to literature procedures (e.g. Maschauer and Prante, Carbohydr. Res. 2009, 753; Takatani et al Carbohydr. Res. 2003, 1073).

(b) Radiosynthesis of 2-[$^{18}$F]fluoroglucopyranosyl azide 33

To the dry $^{18}$F-fluoride-cryptate complex the precursor, 3,4,6-tri-O-acetyl-2-O-trifluoromethanesulfonyl-β-D-mannopyranosyl azide (3.0 mg, 6.5 pmol), in 0.30 mL of anhydrous acetonitrile was added. The mixture was stirred for 5 min at 80° C. to afford a $^{18}$F-incorporation of maximum 75% according to radio-UPLC analysis. After 5 min of cooling and addition of 8 mL of water, the mixture was passed through a reversed-phase cartridge (Sep-Pak C18 Plus; Waters; preconditioned with MeOH and H$_2$O). The cartridge was washed with 5 ml of water. The $^{18}$F-labelled protected intermediate, 3,4,6-tri-O-acetyl-2-deoxy-2-[$^{18}$F]fluoroglucopyranosyl azide, was eluted with 2.0 mL of acetonitrile into another 10 ml sealed reaction vessel and dried under reduced pressure and a nitrogen stream at 80° C. For hydrolysis, 0.25 ml of 60 mM sodium hydroxide solution was added and the mixture was heated to 65° C. for 5 min to complete the deacetylation. After cooling, the mixture was neutralized with 0.25 ml of 60 mM hydrogen chloride solution and directly used for the click reaction without further purification.

(c) Coupling to Folate Alkyne Precursor 14

The deprotected 2-deoxy-2-[$^{18}$F]fluoroglucopyranosyl azide 33 obtained in step (b) was transferred into another reaction vessel containing the folate alkyne 14 in 300 μl DMF, followed by addition of 10 μl 0.1 M Cu(OAc)$_2$ solution and 20 μl 0.1 M sodium ascorbate solution. The reaction mixture was stirred at 50° C. for 15 min. After addition of 3 ml of 0.05 M NH$_4$HCO$_3$ solution the mixture was submitted to the semi-preparative radio-HPLC system. The product fraction [$^{18}$F] FDG-albuminbinder folate (R$_T$=19.3 min) was collected into 20 ml of water and the mixture was passed through a reversed-phase cartridge (Sep-Pak C18 light; Waters; preconditioned with EtOH (5 ml) and H$_2$O (5 ml)). The cartridge was washed with 10 ml of water and the $^{18}$F-labeled product [$^{18}$F]FDG-albuminbinder folate 34 was eluted with 1.0 ml of ethanol into a sterile, pyrogen-free vial. After evaporation of the ethanol, the final product solution was diluted with 2 ml PBS for injection.

The overall decay-corrected yield of the isolated product reached 1-2% after a total synthesis time of 3 h with a radiochemical purity always greater than 95%. The specific activity of [$^{18}$F]FDG-albuminbinder folate 34 was around 40-50 GBq/μmol.

The log D$_{7.4}$ value of [$^{18}$F]FDG-albuminbinder folate was found to be −3.2±0.4 by the shake flask method.

Example 6

Radiolabelling of Compounds of Example 1(f) and 1(p)

(a) with $^{67}$Ga and $^{177}$Lu

A volume of 15 μl of compound 16 and 6 (1 mM) were mixed with 250 μl of Na-acetate buffer (0.4 M, pH 5) and $^{67}$GaCl$_3$ solution (40 MBq, 2.7×10$^{-11}$ mol) or $^{177}$LuCl$_3$ solution (50 MBq, 0.7×10$^{-11}$ mol for 30 nmol compound). The mixture was incubated for 30 min at 90° C., then cooled to RT. DTPA solution (10 μl, 5 mM, pH 5) was added for complexation of potential traces of unreacted $^{67}$Ga or $^{177}$Lu respectively. Quality control was performed by HPLC. The HPLC system comprised a Waters system with a tunable absorbance detector and a Unispec multichannel analyser γ-detector and a Waters XTerraR MS C18 (5 μm, 4.6 mm×150 mm) with an eluent that consisted of aqueous 0.05 M triethylammonium phosphate buffer, at pH 2.25 or pH 7.5, and methanol with a linear gradient to 80% methanol over 30 min. For in vitro cell experiments and the albumin binding assay compounds $^{67}$Ga-16 and $^{67}$Ga-6 or $^{177}$Lu-16 and $^{177}$Lu-6 respectively were purified by HPLC.

For all the in vitro experiments the radioactive compounds were purified via HPLC. The radioactive peak was collected and diluted with PBS. MeOH was removed under a flow of N$_2$.

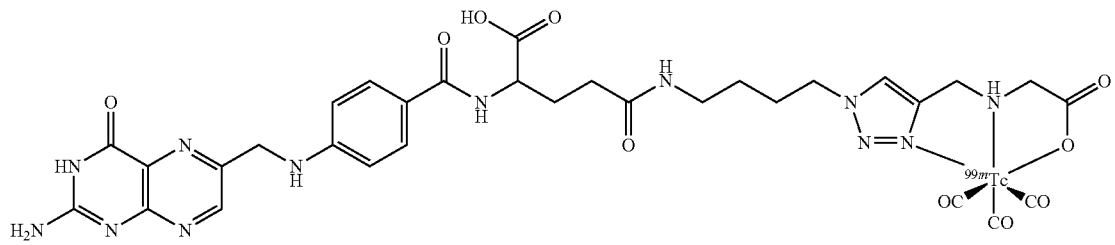

$^{99m}$Tc(CO)$_3$—FA2

-continued

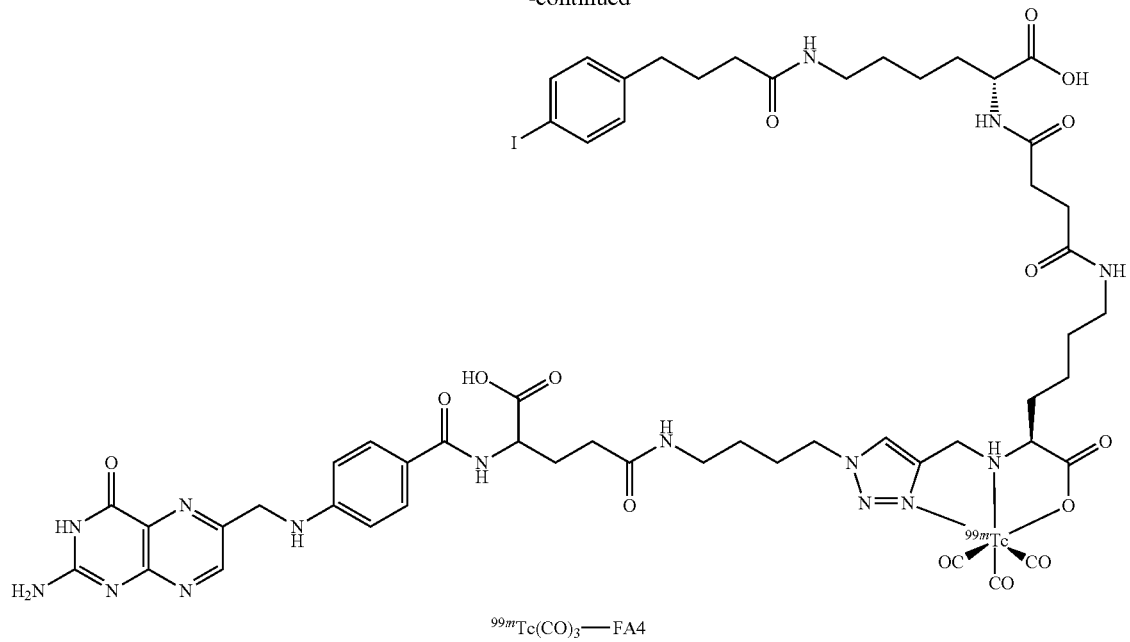

$^{99m}$Tc(CO)$_3$—FA4

(b) with $^{99m}$Tc(CO)$_3$

Eluted [Na][$^{99m}$TcO$_4$] in 0.9% saline solution (1 ml, 2-10 GBq) was added to an Isolink Kit (4.5 mg BC, 2.9 Borax, 7.8 mg Na$_2$(CO)$_3$, 9 mg Na—K-Tartrate under N$_2$ atmosphere. The solution was heated for min to 100° C., then cooled to RT and neutralized using an acidic HCl/phosphate buffer. PBS (250 µl of 1×, pH 7.4), 50 nmol of compound FA2, FA4 or 22 and 200 µl of $^{99m}$Tc(CO)$_3$(H$_2$O)$_3$ (around 0.8 GBq) were mixed in a penicilline vial and heated for 45 min to 80° C. Quality of the radiolabelling was analyzed via HPLC according to above mentioned protocol.

Example 7

In Vitro Stability of $^{177}$Lu-Radiolabeled DOTA-AB-Folate 16

The $^{177}$Lu-radiolabeled DOTA-AB-folate 16 displayed higher stability in human plasma and PBS than the control compound (FIG. 1, filled squares: $^{177}$Lu-DOTA-folate in PBS, filled triangles: $^{177}$Lu-DOTA-folate in plasma, filled circles: $^{177}$Lu-DOTA-AB-folate in PBS, filled diamonds: $^{177}$Lu-DOTA-AB-folate in plasma). The reason for the relatively quick degradation of the control compound $^{177}$Lu-DOTA-folate in PBS is still unknown. Both of the radiofolates showed FR-specific binding to KB tumor cells (human cervical carcinoma cell line overexpressing the FR). The uptake was high and comparable for both compounds. About 75% of total added radiotracer per 0.5 mg cell protein was bound at steady state (after 2 h incubation at 37° C.) whereof about 30% were internalized in the case of $^{177}$Lu-DOTA-AB-folate and 15% in the case of the control compound.

Example 8

Figure 2:
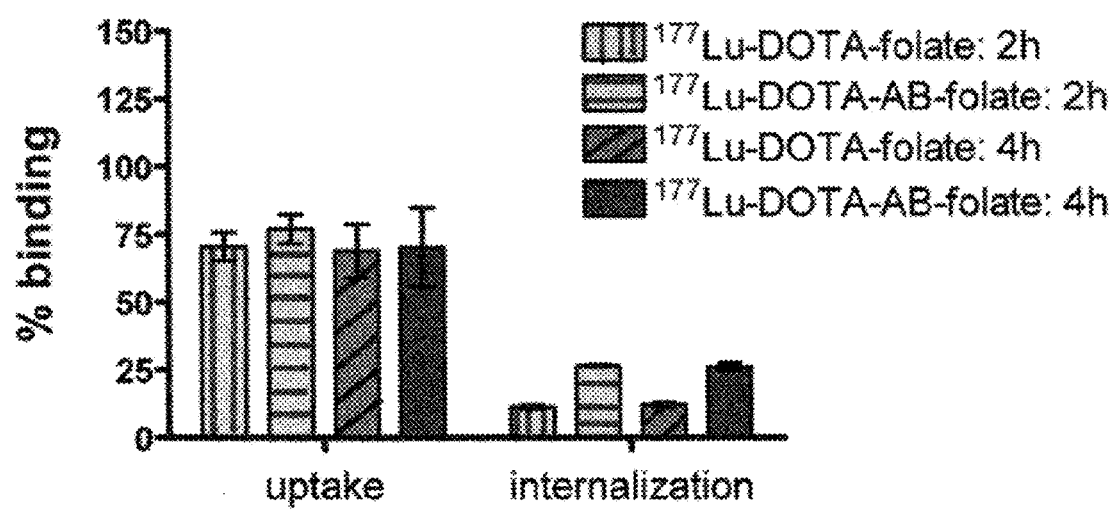
FIG. 2: Cell uptake and internalization of $^{177}$Lu-DOTA-folate and $^{177}$Lu-DOTA-AB-folate 16 in FR-positive KB-cells at 2 h and 4 h (vertically striped bars represent $^{177}$Lu-DOTA-folate at 2 h, horizontally striped bars represent $^{177}$Lu-DOTA-AB-folate at 2 h, diagonally striped bars represent $^{177}$Lu-DOTA-folate at 4 h, filled bars represent $^{177}$Lu-DOTA-AB-folate at 4 h).

Cell Uptake and Internalization of $^{177}$Lu-Radiolabeled DOTA-AB-Folate 16 in FR-Positive KB-Cells Determination octanol/PBS pH 7.4 distribution coefficient (log D value) showed high negative values (−4.04±0.01 for $^{177}$Lu-DOTA-AB-folate 16 and −4.44±0.29 for $^{177}$Lu-DOTA-folate). Filter tests performed for the determination of the albumin bound fraction of the radiotracers revealed about 90% binding of $^{177}$Lu-DOTA-AB-folate whereas the control compound did not show binding to albumin (FIG. 2 (from left to right): columns 1 (vertically striped) and 3 (diagonally striped): $^{177}$Lu-DOTA-folate at 2 h and 4 h, respectively; columns 2 (horizontally striped) and 4 (filled): $^{177}$Lu-DOTA-AB-folate at 2 h and 4 h respectively).

Example 9

Figure 3:
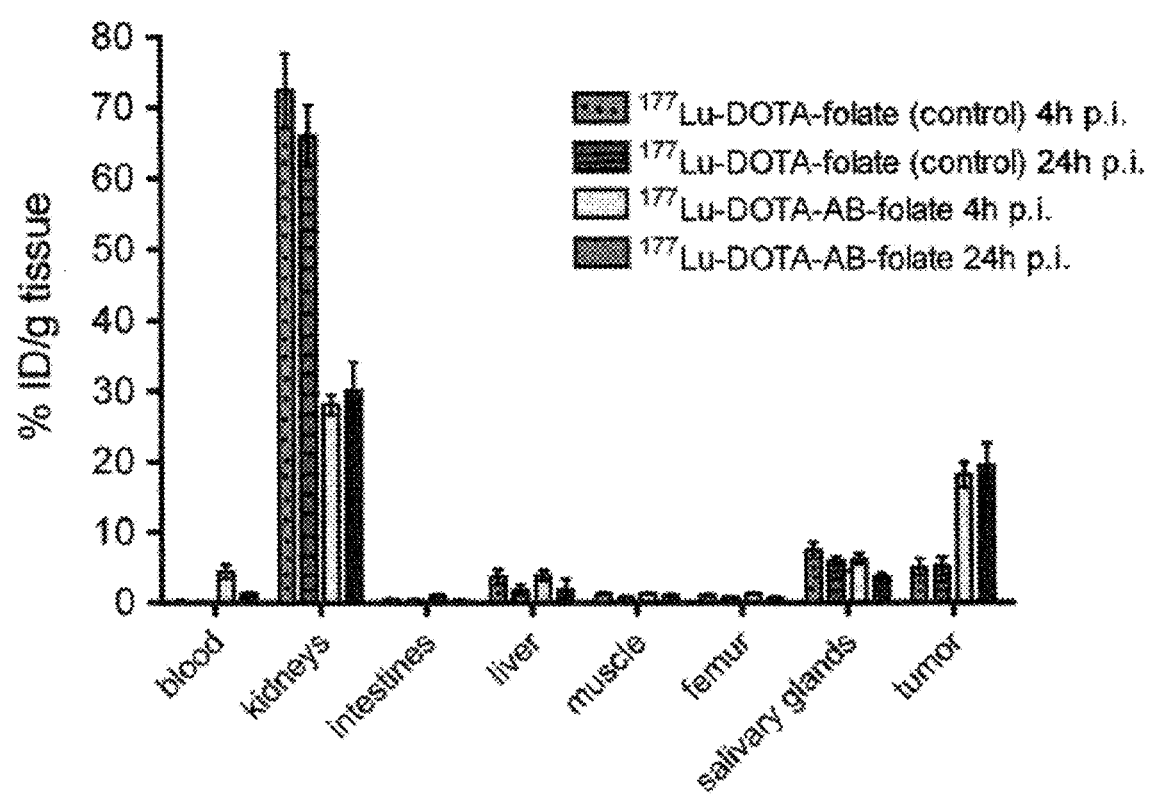
FIG. 3: Biodistribution study in KB-tumor bearing mice 4 h and h after injection of $^{177}$Lu-DOTA-AB-folate and the control compound $^{177}$Lu-DOTA-folate (dotted bars represent $^{177}$Lu-DOTA-folate at 4 h p.i., striped bars represent $^{177}$Lu-DOTA-folate at 24 h p.i., empty bars represent $^{177}$Lu-DOTA-AB-folate at 4 h p.i., filled bars represent $^{177}$Lu-DOTA-AB-folate at 24 h p.i.).
Figure 4:
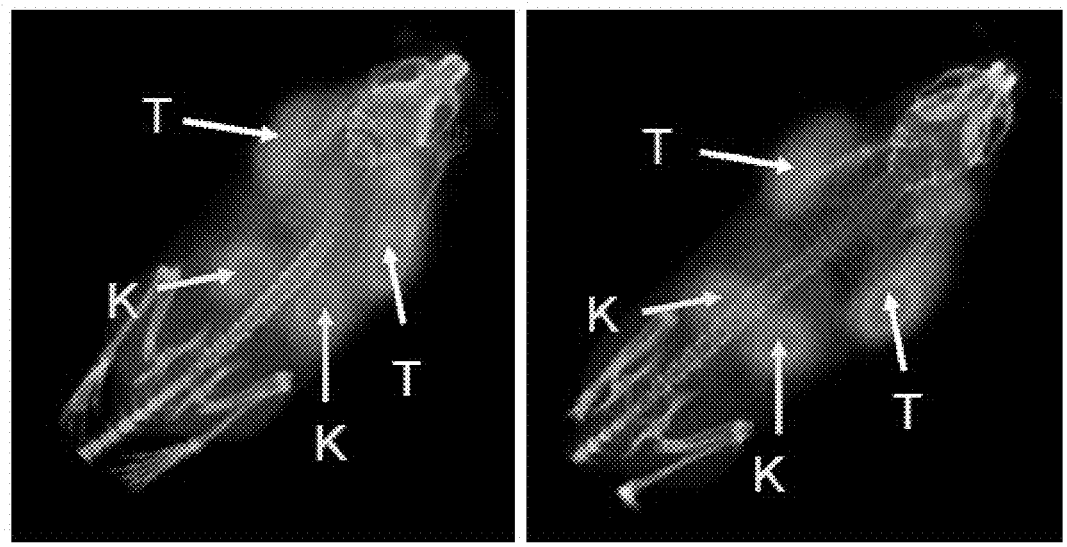
FIG. 4(A), (B): SPECT/CT Images of tumor-bearing mice: Uptake of a $^{177}$Lu-radiolabeled (A) and $^{161}$Tb-radiolabeled DOTA-AB-folate (B) in a KB tumor xenograft (T) and in the kidneys (K) at 4 h p.i. (left) and 24 h p.i. (right).
Figure 4:
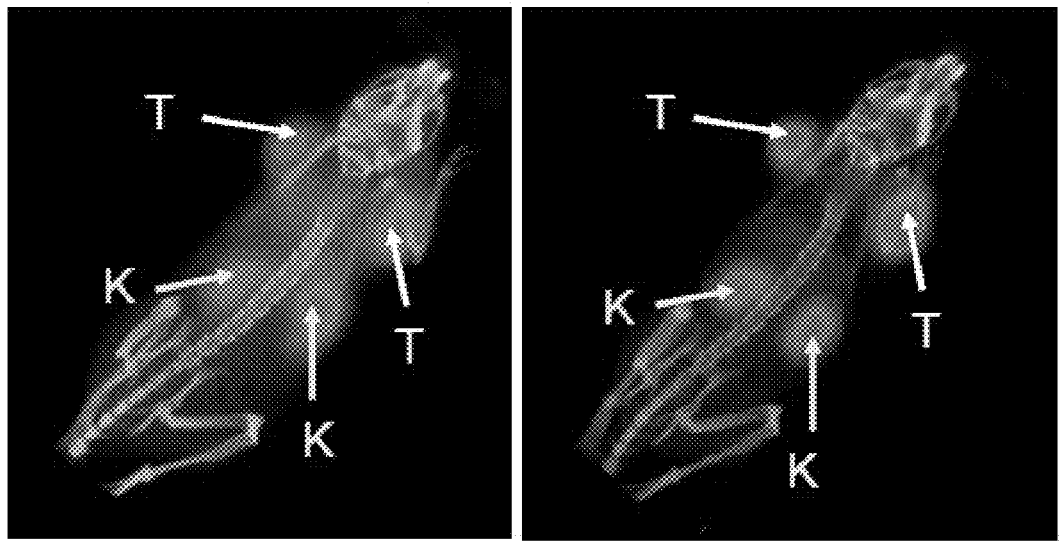

Biodistribution Study of $^{177}$Lu-Radiolabeled DOTA-AB-Folate 16 in KB-Tumor Bearing Mice In vivo experiments were performed in female nude mice bearing KB tumor xenografts. Mice have been euthanized at different time points after injection of either $^{177}$Lu-radiolabeled DOTA-AB-folate 16 or the control compound $^{177}$Lu-DOTA-folate, respectively. As expected, we found an increased circulation time of the $^{177}$Lu-DOTA-AB-folate 16 in the blood (>4% ID/g and >1% ID/g at 4 h and 24 h p.i.) compared to the control compound (~0.2% ID/g and ~0.05 ID/g at 4 h and 24 h p.i.). The tumor uptake of $^{177}$Lu-DOTA-AB-folate 16 was very high already h after injection (18.12±1.80% ID/g) and retained over time. This was about 4-fold higher the uptake achieved with the control compound (4.98±1.21% ID/g, 4 h p.i.). In contrast, kidney uptake was only about 30% ID/g at 4 h and 24 h p.i. of $^{177}$Lu-DOTA-AB-folate compared to more than 70% ID/g for the control compound. Thanks to the albumin binding moiety the tissue distribution of the DOTA-folate could be significantly improved in that the tumor-to-kidney ratio was increased severalfold (see FIG. 3: Biodistribution in KB-tumor bearing mice 4 h and 24 h after injection of $^{177}$Lu-DOTA-AB-folate (white and black, columns 3 and 4 from left to right) and the control compound $^{177}$Lu-DOTA-folate (dotted and striped, columns 1 and 2 from left to right). FIG. 4(A) illustrates the uptake in a KB tumor xenograft (T) and in the kidneys (K) of a $^{177}$Lu-radiolabeled DOTA-AB-folate 16 at 3 h p.i. (left image) and at h p.i. (right image) at a dosage of 59 MBq. FIG. 4(B) illustrates the uptake in a KB tumor xenograft (T) and in the kidneys (K) of a $^{161}$Tb-radiolabeled DOTA-AB-folate 16 at 2 h p.i. (left image) and at 48 h p.i. (right image) at a dosage of 58 MBq.

Figure 5:
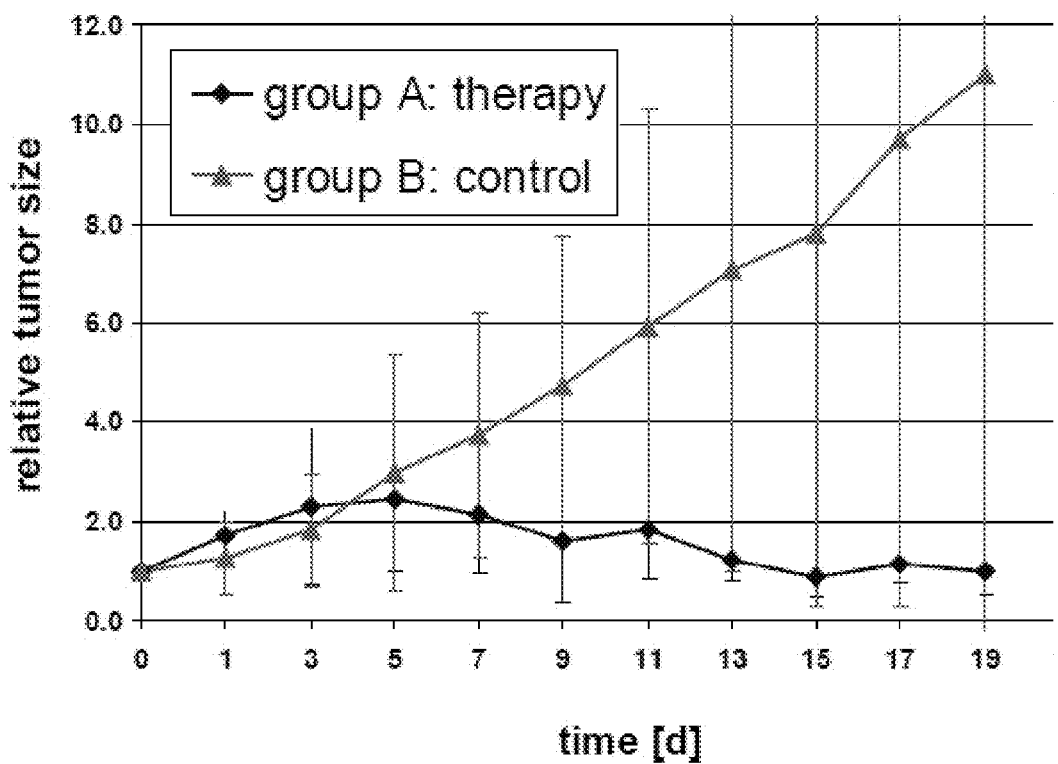
FIG. 5(A), (B): Effect of $^{177}$Lu-radiolabeled DOTA-AB-folate 16 (group A) or the control $^{177}$Lu-radiolabeled DOTA-folate (group B) in KB tumor bearing nude mice over time, i.e. 19 days (-▲- represents group A, -♦- represents group B).
Figure 5:
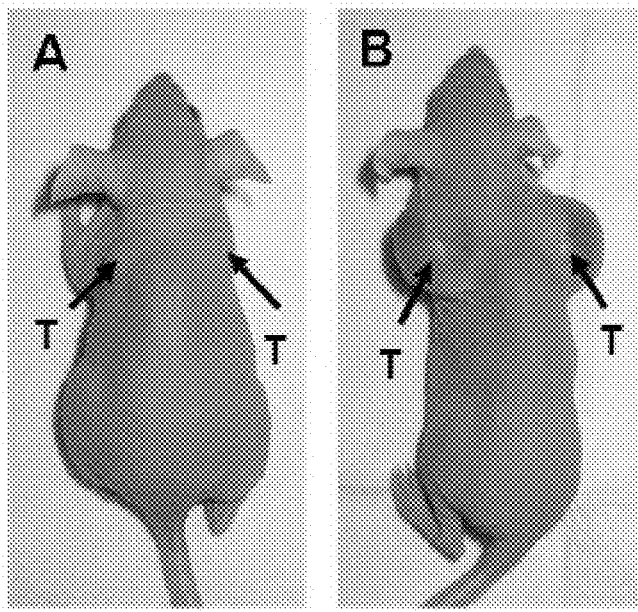

FIG. 5 illustrates the efficacy of therapy in KB tumor bearing nude mice over time (19 days). The mice were inoculated with 4.5 Mio KB tumor cells on each shoulder 5 days before therapy. Group A represents the mice injected at t=0 days with $^{177}$Lu-radiolabeled DOTA-AB-folate 16. Group B represents the control group, i.e. mice injected at t=0 with PBS pH 7.4. FIG. 5(A) illustrates the relative tumor size (y-axis) of group A (filled diamonds) and group B (filled triangles) over time (x-axis). FIG. 5(B) shows the results on t=17 days.

Example 10

Biodistribution Study of $^{18}$F-FDG-AB-Folate 34 in KB-Tumor Bearing Mice

In vivo experiments were performed in female nude mice bearing KB tumor xenografts.

Animals were injected with ~3 MBq of [$^{18}$F]FDG-AB-folate 34 via a lateral tail vein. Animals were sacrificed 2 h after radiotracer injection. Organs- and tissues were dissected and measured in the γ-counter (Wizard, PerkinElmer). The incorporated radioactivity was expressed as percentage injected dose (% ID) per gram of tissue. The biodistribution data is summarized in Table 1.

TABLE 1

Ex vivo biodistribution studies with [$^{18}$F]FDG-AB-folate in nude mice bearing KB tumor xenografts 2 h after injection

| Organ or tissue | 2 h p.i. (n = 3) |
|---|---|
| % ID/g in: | |
| Blood | 2.93 ± 0.55 |
| Brain | 0.89 ± 0.17 |
| Heart | 3.20 ± 0.53 |
| Lungs | 2.44 ± 0.58 |
| Spleen | 0.81 ± 0.03 |
| Liver | 7.14 ± 0.78 |
| Gallbladder | 83.78 ± 16.78 |
| Kidneys | 14.98 ± 1.47 |
| Stomach | 1.93 ± 0.51 |
| Intestine | 8.84 ± 7.07 |
| Feces | 53.02 ± 26.52 |
| Salivary glands | 7.55 ± 0.08 |
| Bone | 1.50 ± 0.24 |
| Muscle | 1.62 ± 0.26 |
| Tumor | 9.51 ± 0.08 |
| Ratios: | |
| Tumor/Liver | 1.34 ± 0.16 |
| Tumor/Kidneys | 0.64 ± 0.07 |
| Tumor/Blood | 3.33 ± 0.59 |

The invention claimed is:

1. A compound of formula I,

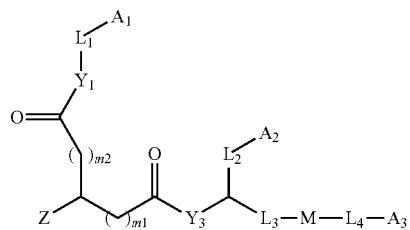

I wherein

Z is a pteroate or derivative thereof, $L_1$, $L_4$ are independently of each other a covalent bond or a straight-chain or branched C(1-8)alkyl, which is unsubstituted or substituted by at least one CN, Hal, OR', NHR', $CO_2R'$ or $NO_2$, R' represents H or C(1-8)alkyl, $L_2$ is a covalent bond or a linking group, which is a straight-chain or branched C(1-8)alkyl, which is unsubstituted or substituted by at least one OR', NHR', or $CO_2R'$, and wherein one or more of the non-adjacent $CH_2$ groups are optionally independently replaced by —O—, —CO—, —CO—O—, —O—CO—, —NR'—, —NR'—CO—, or —CO—NR', $L_3$ is a covalent bond or a linking group, which is a straight-chain or branched C(1-8)alkyl, which is unsubstituted or substituted by at least one CN, Hal, OR', NHR', $CO_2R'$ or $NO_2$, and wherein one or more of the non-adjacent $CH_2$ groups are optionally independently replaced by a group selected from the group consisting of —O—, —CO—, —CO—O—, —O—CO—, —NR'—, —NR'—CO—, —CO—NR'—, —NR'—CO—O—, —O—CO—NR'—, —NR'—CO—NR'—, —CH═CH—, —C≡C—, —O—CO—O—, —S—R'—, —$SO_3$R'—, and a five-membered azaheterocycle, $Y_1$, $Y_3$ are independently of each other O, N or S, $A_1$, $A_2$, $A_3$ are independently of each other H, a capping group, or an albumin binder, M is a radionuclide-based therapeutic or diagnostic moiety, $m_1$, $m_2$ are independently of each other 0, 1, 2 or 3, with the proviso that at least one, of $A_1$, $A_2$ and $A_3$ is an albumin binder.

2. The compound according to claim 1 having formula II

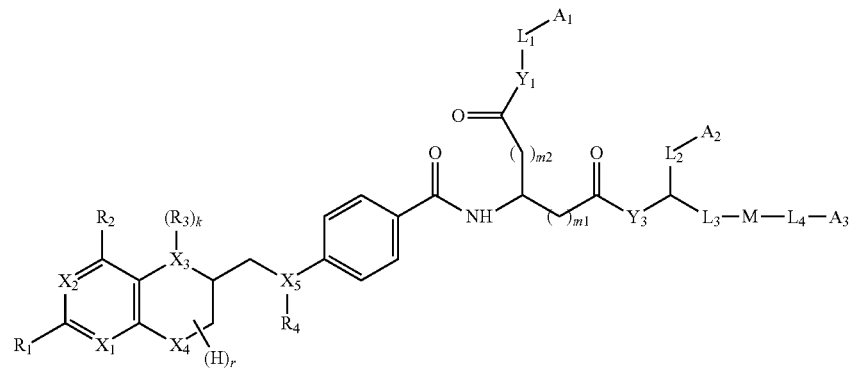

II wherein $X_1$ to $X_5$ are independently of each other C, N or O, $R_1$, $R_2$ are independently of each other H, halogen, C(1-12)alkyl, C(2-12)alkenyl, C(2-12)alkynyl, —OR$_5$, —COR$_5$, —COOR$_5$, —NHR$_5$, —CONHR$_5$, —CONHR$_5$, $R_5$ represents H, halo, C(1-12)alkyl, C(2-12)alkenyl, C(2-12)alkynyl, —OR', —COR', —COOR', or —NHR', R' is H or C(1-8)alkyl, $R_3$, $R_4$ are independently of each other H, nitroso, C(1-12)alkyl, —OR', —COR' or halosubstituted —COR', $L_1$, $L_4$ are independently of each other a covalent bond or a straight-chain or branched C(1-8)alkyl, which is unsubstituted or substituted by at least one CN, Hal, OR', NHR', CO$_2$R' or NO$_2$, $L_2$ is a covalent bond or a linking group, which is a straight-chain or branched C(1-8)alkyl, which is unsubstituted or substituted by at least one OR', NHR', or CO$_2$R', and wherein one or more of the non-adjacent CH$_2$ groups are optionally independently replaced by —O—, —CO—, —CO—O—, —O—CO—, —NR'—, —NR'—CO—, or —CO—NR', $L_3$ is a covalent bond or a linking group, which is a straight-chain or branched C(1-8)alkyl, which is unsubstituted or substituted by at least one CN, Hal, OR', NHR', CO$_2$R' or NO$_2$, and wherein one or more of the non-adjacent CH$_2$ groups are optionally independently replaced by a group selected from the group consisting of —O—, —CO—, —CO—O—, —O—CO—, —NR'—, —NR'—CO—, —CO—NR'—, —NR'—CO—O—, —O—CO—NR'—, —NR'—CO—NR'—, —CH=CH—, —C≡C—, —O—CO—O—, —S—R'—, —SO$_3$R'—, and a five-membered azaheterocycle, $Y_1$, $Y_3$ are independently of each other O, N or S, $A_1$, $A_2$, $A_3$ are independently of each other H, a capping group, or an albumin binder, M is a radionuclide-based therapeutic or diagnostic moiety, $m_1$, $m_2$ are independently of each other 0, 1, 2 or 3, k is 0 or 1, r has a value of 1 to 7.

with the proviso that at least one of $A_1$, $A_2$ and $A_3$ is an albumin binder.

3. The compound according to claim 2, wherein $R_3$ is H, C(1-12)alkyl, or —CO—C(1-8)alkyl.

4. The compound according to claim 2, wherein $R_4$ is H, nitroso, —O—C(1-8)alkyl, or —CO—C(1-8)alkyl.

5. The compound according to claim 2, wherein $R_1$ and $R_2$ are independently of each other H, C(1-12)alkyl, —OR$_5$, —NHR$_5$, wherein $R_5$ is H, C(1-12)alkyl, C(2-12)alkenyl, or C(2-12)alkynyl.

6. The compound according to claim 2, wherein $X_1$ to $X_5$ are independently of each other N or O, M is a imaging moiety $M_1$ or $M_2$, $M_1$ is a chelated metal radionuclide, and $M_2$ is a gamma- or positron-emitting non-metal radionuclide optionally in combination with a prosthetic group.

7. The compound according to claim 1 wherein the albumin binder is a linear or branched lipophilic group having 12-40 carbon atoms and a distal acidic group.

8. The compound according to claim 1, having formula IVa, IVb or IVc

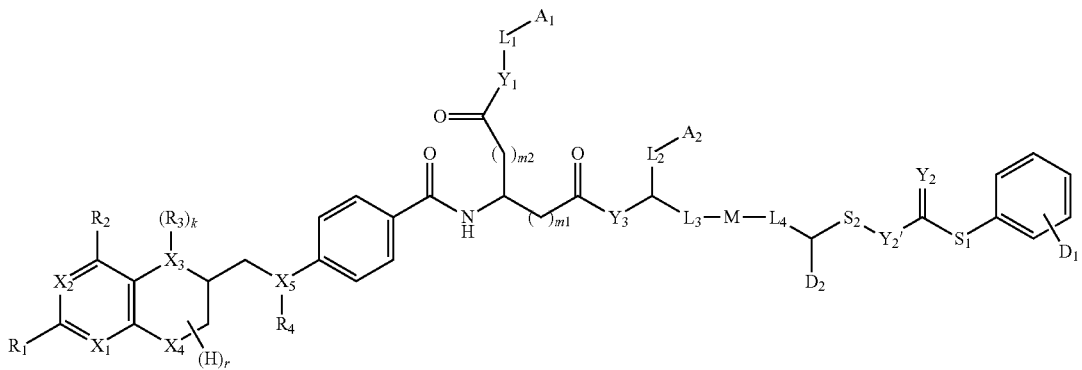

IVa

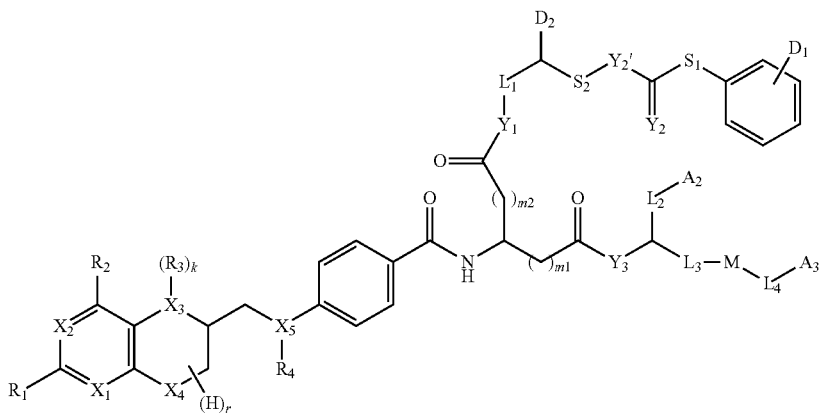

IVb

-continued

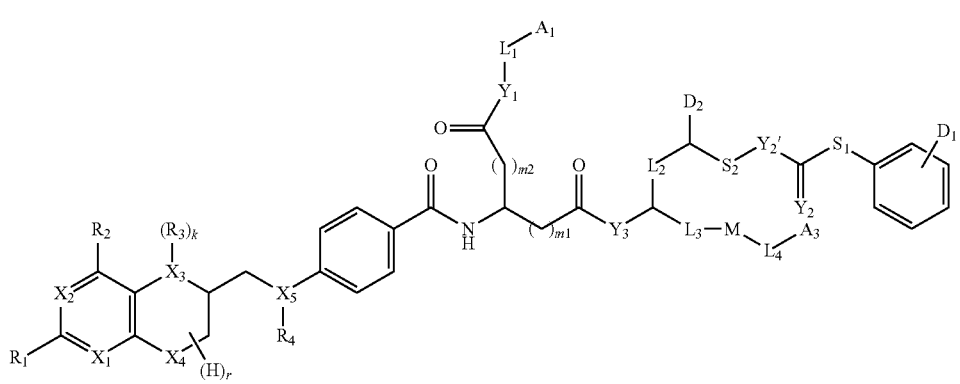

IVc wherein
X$_1$ to X$_5$ are independently of each other C, N or O,
Y$_1$, Y$_3$ are independently of each other N, O or S,
Y$_2$, Y$_2'$ are independently of each other N, O or S,
R$_1$, R$_2$ are independently of each other H, halogen, C(1-12)alkyl, C(2-12)alkenyl, C(2-12)alkynyl, —OR$_5$, —COR$_5$, —COOR$_5$, —NHR$_5$, —CONHR$_5$,
R$_5$ represents H, halo, C(1-12)alkyl, C(2-12)alkenyl, C(2-12)alkynyl, —OR', —COR', —COOR', or —NHR',
R' is H or C(1-8)alkyl,
R$_3$, R$_4$ are independently of each other H, nitroso, C(1-12)alkyl, —OR', —COR' or halosubstituted —COR',
A$_1$ is H or a capping group,
A$_2$ is H or a capping group,
A$_3$ is H or a capping group,
M is a radionuclide-based therapeutic or diagnostic moiety,
m$_1$, m$_2$ are independently of each other 0, 1, 2 or 3,
L$_1$, L$_4$ are independently of each other a covalent bond or a straight-chain or branched C(1-8)alkyl, which is unsubstituted or substituted by at least one CN, Hal, OR', NHR', CO$_2$R' or NO$_2$,
L$_2$ is a covalent bond or a linking group, which is a straight-chain or branched C(1-8)alkyl, which is unsubstituted or substituted by at least one OR', NHR', or CO$_2$R', and wherein one or more of the non-adjacent CH$_2$ groups are optionally independently replaced by —O—, —CO—, —CO—O—, —O—CO—, —NR'—, —NR'—CO—, —CO—NR',
L$_3$ is a covalent bond or a linking group, which is a straight-chain or branched C(1-8)alkyl, which is unsubstituted or substituted by at least one CN, Hal, OR', NHR', CO$_2$R' or NO$_2$, and wherein one or more of the non-adjacent CH$_2$ groups are optionally independently replaced by a group selected from the group consisting of —O—, —CO—, —CO—O—, —O—CO—, —NR'—, —NR'—CO—, —CO—NR'—, —NR'—CO—O—, —O—CO—NR'—, —NR'—CO—NR'—, —CH═CH—, —C≡C—, —O—CO—O—, —S—R'—, —SO$_3$R'—, and a five-membered azaheterocycle,
S$_1$, S$_2$ are independently of each other a single bond or a spacer which is straight-chain or branched C(1-12)alkyl, which is unsubstituted or substituted by at least one CN, Hal, OR', NHR', CO$_2$R', SH, SO$_3$H or NO$_2$, and wherein one or more of the non-adjacent CH$_2$ groups are optionally independently replaced by —O—, —CO—, —CO—O—, —O—CO—, —NR'—, —NR'—CO—, —CO—NR'—, —NR'—CO—O—, —O—CO—NR'—, —NR'—CO—NR'—, —CH═CH—, —C≡C—, —O—CO—O—, —S—R'—, or —SO$_3$R'—, D$_1$ is H, halogen, C(1-12)alkyl, C(2-12)alkenyl, C(2-12)alkynyl, —OR$_{5*}$, —COR$_{5*}$, —COOR$_{5*}$, —NHR$_{5*}$, or —CONHR$_{5*}$,
R$_{5*}$ represents H, C(1-12)alkyl, C(2-12)alkenyl, or C(2-12)alkynyl,
D$_2$ is an acidic group,
k is 0 or 1,
r has a value of 1 to 7.

9. The compound according to claim 8, wherein the acidic group is a group capable of ionizing to donate a hydrogen ion to a base to form a salt, which is —COOH, —SO$_3$H, —SO$_2$H, —NR'SO$_3$H, —P(O)(OH)$_2$, wherein R' represents H or C(1-8)alkyl.

10. The compound according to claim 8, wherein L$_2$ is a covalent bond or straight-chain or branched C(1-6)alkyl.

11. The compound according to claim 8, wherein
X$_1$ to X$_5$ are independently of each other N or O,
M is an imaging moiety M$_1$ or M$_2$, M$_1$ is a chelated metal radionuclide, and M$_2$ is a gamma- or positron-emitting non-metal radionuclide optionally in combination with a prosthetic group.

12. The compound according to claim 1, wherein m$_1$ is 2 and m$_2$ is 0 or wherein m$_1$ is 0 and m$_2$ is 2.

13. The compound according to claim 1, wherein M is a radionuclide-based therapeutic or diagnostic moiety M$_1$ or M$_2$, wherein M$_1$ is a chelated metal radionuclide, and M$_2$ is a gamma- or positron-emitting non-metal radionuclide optionally in combination with a prosthetic group.

14. The compound according to claim 1, with the proviso that when A$_2$ is an albumin binder, M is a chelated metal radionuclide M$_1$.

15. The compound according to claim 14, wherein the metal radionuclide is selected from the group consisting of $^{99}$Tc, $^{51}$Cr, $^{67}$Ga, $^{68}$Ga, $^{47}$Sc, $^{51}$Cr, $^{167}$Tm, $^{141}$Ce, $^{111}$In, $^{168}$Yb, $^{175}$Yb, $^{140}$La, $^{90}$Y, $^{88}$Y, $^{153}$Sm, $^{166}$Ho, $^{165}$Dy, $^{166}$Dy, $^{62}$Cu, $^{64}$Cu, $^{67}$Cu, $^{97}$Ru, $^{103}$Ru, $^{186}$Re, $^{188}$Re, $^{203}$Pb, $^{211}$Bi, $^{213}$Bi, $^{214}$Bi, $^{105}$Rh, $^{109}$Pd, $^{117}$mSn, $^{149}$Pm, $^{161}$Tb, $^{177}$Lu, $^{198}$Au and $^{199}$Au.

16. The compound according to claim 14, wherein the metal chelator is a bidentate, tridentate, or tetradentate, linear, tripodal or macrocyclic ligand.

17. The compound according to claim 14, wherein the metal chelator is a linear or macrocyclic polyaminocarboxylate chelator.

18. The compound according to claim 14, wherein the metal chelator is DTPA, DOTA, DO3A, HP-DO3A, EDTA, TETA, EHPG, HBED, NOTA, DOTMA, TETMA, PDTA, TTHA, LICAM, or MECAM.

19. The compound according to claim 1, wherein the imaging moiety M is a chelated metal radionuclide M$_1$ comprising a metal radionuclide and a metal chelator.

20. The compound according to claim 1, wherein the imaging moiety M is a gamma- or positron-emitting non-metal radionuclide $M_2$ selected from the group consisting of $^{11}C$, $^{13}N$, $^{15}O$, $^{17}F$, $^{18}F$, $^{75}Br$, $^{76}Br$, $^{77}Br$, $^{123}I$, $^{124}I$, and $^{131}I$, optionally in combination with a prosthetic group.

21. The compound according to claim 1, wherein $L_1$ is a covalent bond or straight-chain or branched C(1-6)alkyl.

22. The compound according to claim 1, wherein $Y_1$ is O or N and/or $Y_3$ is N.

23. The compound according to claim 1, wherein $L_3$ is a straight-chain or branched C(1-8)alkyl, which is unsubstituted or substituted by at least one Hal, OR', NHR', or $CO_2R'$, and wherein one or more of the non-adjacent $CH_2$ groups are optionally independently replaced by a group selected from the group consisting of —O—, —CO—, —CO—O—, —NR'—, —NR'—CO—, and a five-membered azaheterocycle, which is a triazolyl or tetrazolyl group, and wherein R' represents H or C(1-8)alkyl.

24. The compound according to claim 1, wherein $L_3$ is a straight-chain or branched C(1-8)alkyl, which is unsubstituted or substituted by at least one Hal, OR', NHR', or $CO_2R'$, and wherein one or more of the non-adjacent $CH_2$ groups are optionally independently replaced by —O—, —CO—, —CO—O—, —NR'—, —NR'—CO—, or $L_3$ is a group of formulae (a), (b), or (c)

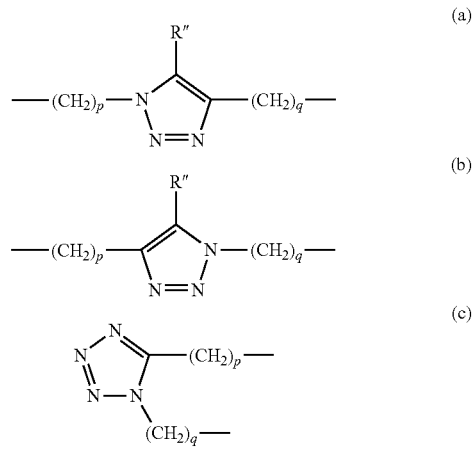

wherein
R" is H or a straight-chain or branched C(1-8)alkyl, which is unsubstituted or substituted by at least one CN, Hal, or $NO_2$,
p,q are independently of each other 0, 1, 2, 3, 4, 5 or 6.

25. The compound according to claim 1 having formulae VI a-e

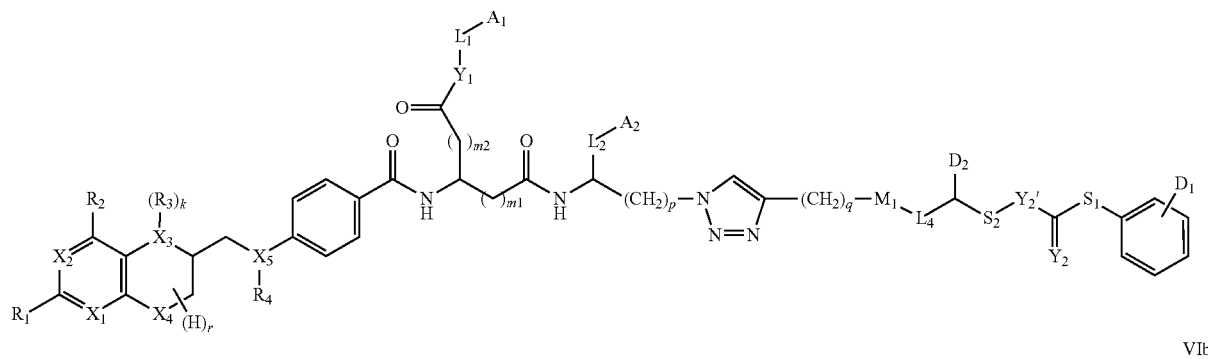

VIa

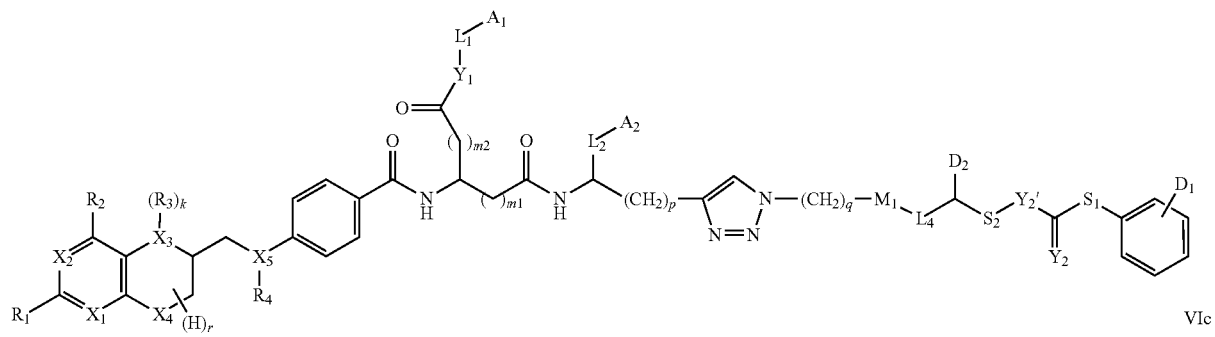

VIb

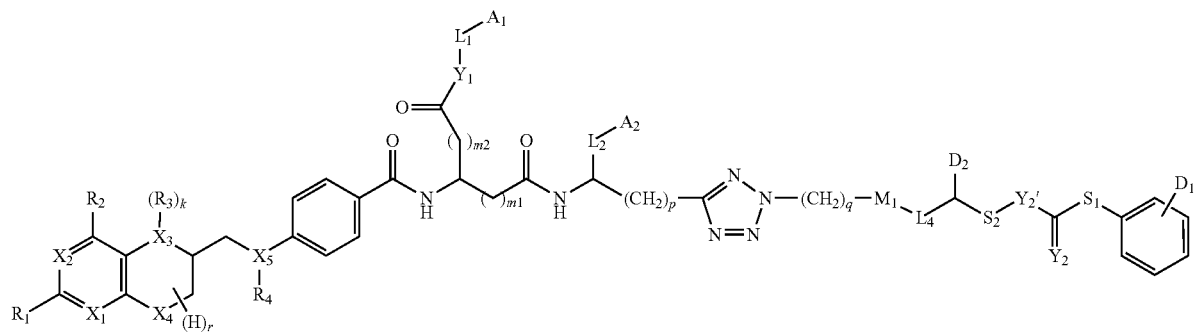

VIc

-continued

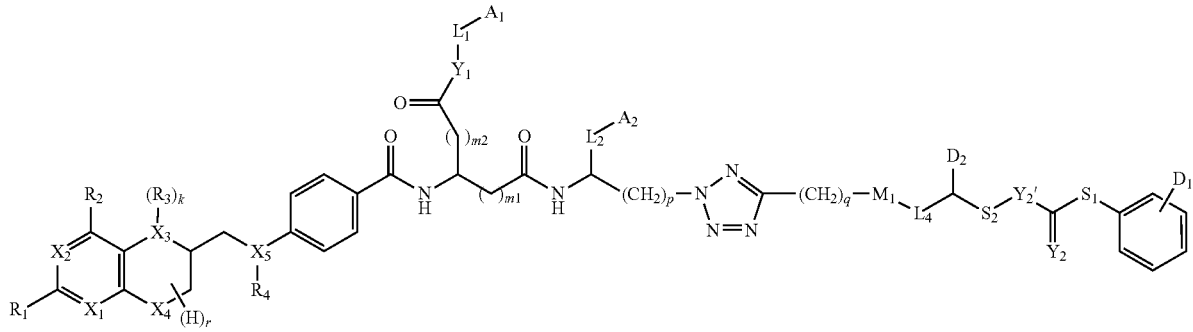

VId

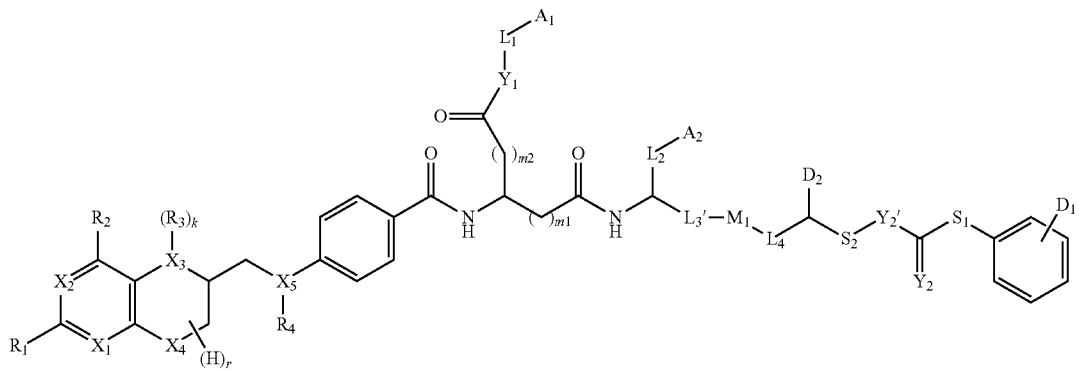

VIe wherein $X_1$ to $X_5$ are independently of each other C, N or O, $Y_1, Y_2, Y_{2'}$ are independently of each other N, O or S, $R_1, R_2$ are independently of each other H, halogen, C(1-12)alkyl, C(2-12)alkenyl, C(2-12)alkynyl, —$OR_5$, —$COR_5$, —$COOR_5$, —$NHR_5$, —$CONHR_5$, $R_5$ represents H, halo, C(1-12)alkyl, C(2-12)alkenyl, C(2-12)alkynyl, —OR', —COR', —COOR', or —NHR', R' is H or C(1-8)alkyl, $R_3, R_4$ are independently of each other H, nitroso, C(1-12)alkyl, —OR', —COR' or halosubstituted —COR', $A_1$ is H or a capping group, $A_2$ is H or a capping group, $M_1$ is a linear or macrocyclic polyaminocarboxylate, complexed with a radioimaging metal ion, $m_1, m_2$ are independently of each other 0, 1, 2 or 3, $L_1, L_4$ are independently of each other a covalent bond or a straight-chain or branched C(1-8)alkyl, which is unsubstituted or substituted by at least one CN, Hal, OR', NHR', $CO_2R'$ or $NO_2$, $L_2$ is a covalent bond or a linking group, which is a straight-chain or branched C(1-8)alkyl, which is unsubstituted or substituted by at least one OR', NHR', or $CO_2R'$, and wherein one or more of the non-adjacent $CH_2$ groups are optionally independently replaced by —O—, —CO—, —CO—O—, —O—CO—, —NR'—, —NR'—CO—, —CO—NR', $S_1, S_2$ are independently of each other a single bond or a spacer which is a straight-chain or branched C(1-12)alkyl, which is unsubstituted or substituted by at least one CN, Hal, OR', NHR', $CO_2R'$, SH, $SO_3H$ or $NO_2$, and wherein one or more of the non-adjacent $CH_2$ groups are optionally independently replaced by —O—, —CO—, —CO—O—, —O—CO—, —NR'—, —NR'—CO—, —CO—NR'—, —NR'—CO—O—, —O—CO—NR'—, —NR'—CO—NR'—, —CH=CH—, —C≡C—, —O—CO—O—, —S—R'—, —$SO_3R'$—, $D_1$ is H, halogen, C(1-12)alkyl, C(2-12)alkenyl, C(2-12)alkynyl, —$OR_{5*}$, —$COR_{5*}$, —$COOR_{5*}$, —$NHR_{5*}$, or —$CONHR_{5*}$, $R_{5*}$ represents H, C(1-12)alkyl, C(2-12)alkenyl, or C(2-12)alkynyl, $D_2$ is an acidic group, $L_{3'}$ is straight-chain or branched C(1-8)alkyl, which is unsubstituted or substituted by at least one Hal, OR', NHR', or $CO_2R'$, and wherein one or more of the non-adjacent $CH_2$ groups are optionally independently replaced by —O—, —CO—, —CO—O—, —NR'—, or —NR'—CO—, p, q are independently of each other 0, 1, 2, 3, 4, 5 or 6, k is 0 or 1, r has a value of 1 to 7.

26. The compound according to claim 25, wherein $X_1$ to $X_5$ are independently of each other N or O, and $M_1$ is DTPA, DOTA, DO3A, HP-DO3A, EDTA, TETA, NOTA, or DOTMA complexed with a radioimaging metal ion.

27. The compound according to claim 1 having formulae VII a-e
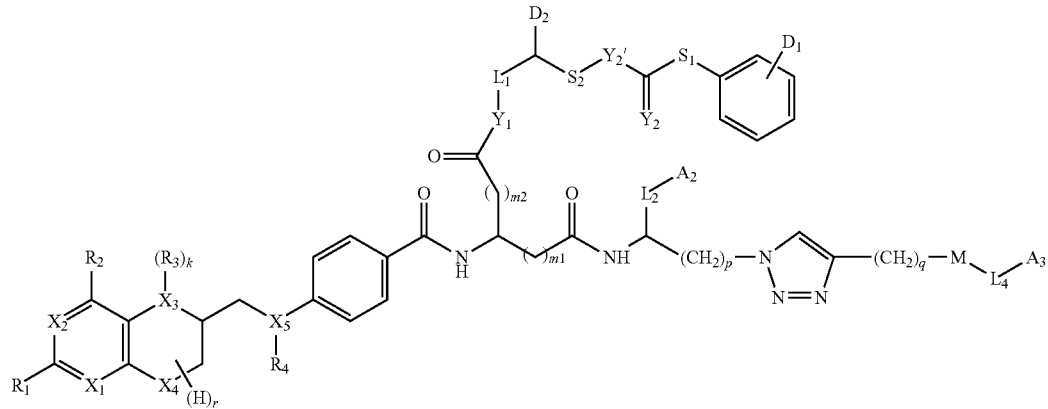
VIIa
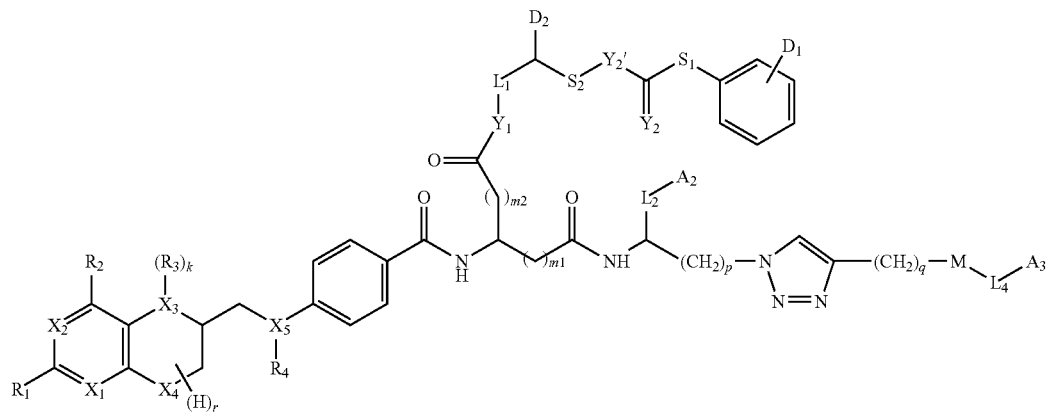
VIIb
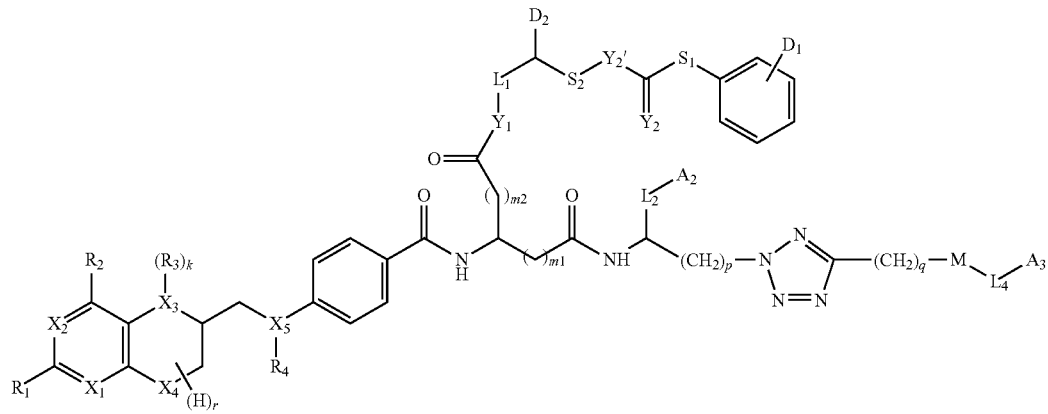
VIIc
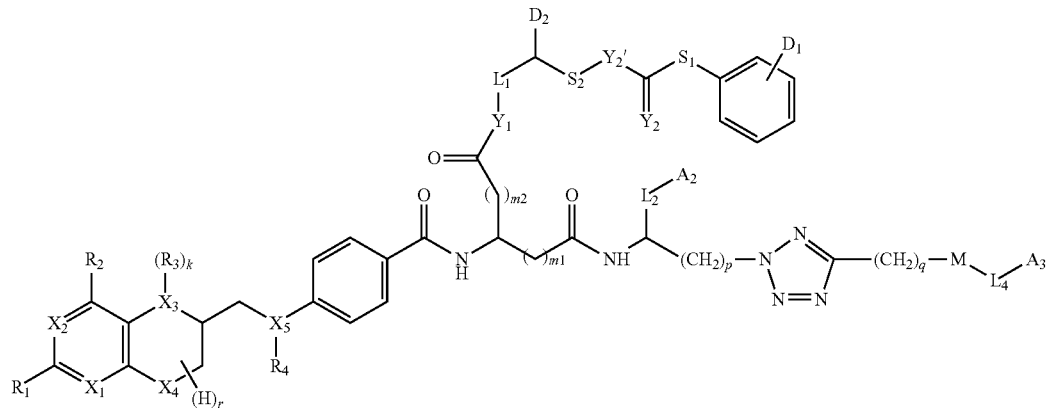
VIId VIIe

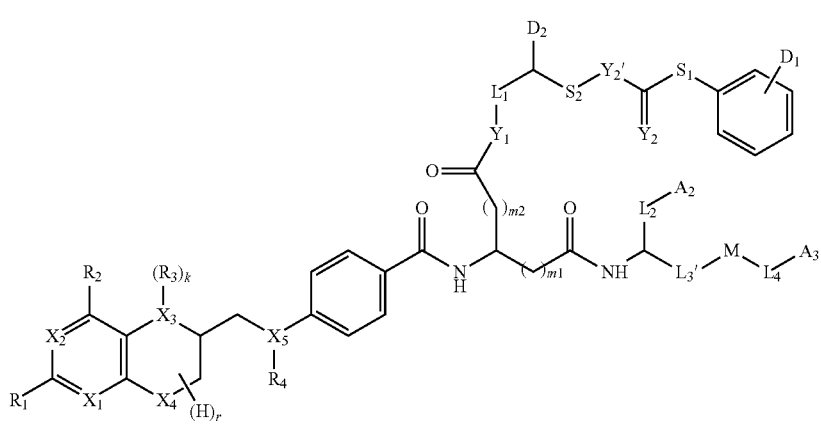

wherein
$X_1$ to $X_5$ are independently of each other C, N or O,
$Y_1, Y_2, Y_{2'}$ are independently of each other N, O or S,
$R_1, R_2$ are independently of each other H, halogen, C(1-12)alkyl, C(2-12)alkenyl, C(2-12)alkynyl, —$OR_5$, —$COR_5$, —$COOR_5$, —$NHR_5$, —$CONHR_5$,
$R_5$ represents H, halo, C(1-12)alkyl, C(2-12)alkenyl, C(2-12)alkynyl, —OR', —COR', —COOR', or —NHR',
R' is H or C(1-8)alkyl,
$R_3, R_4$ are independently of each other H, nitroso, C(1-12)alkyl, —OR', —COR' or halosubstituted —COR',
$A_2$ is H or a capping group,
$A_3$ is H or a capping group,
M is an imaging moiety $M_1$ or $M_2$,
$M_1$ is a chelated metal radionuclide which is a linear or macrocyclic polyaminocarboxylate, complexed with a metal radionuclide ion,
$M_2$ is a gamma- or positron-emitting non-metal radionuclide, optionally in combination with a prosthetic group,
$m_1, m_2$ are independently of each other 0, 1, 2 or 3,
$L_1, L_4$ are independently of each other a covalent bond or a straight-chain or branched C(1-8)alkyl, which is unsubstituted or substituted by at least one CN, Hal, OR', NHR', $CO_2R'$ or $NO_2$,
$L_2$ is a covalent bond or a linking group, which is a straight-chain or branched C(1-8)alkyl, which is unsubstituted or substituted by at least one OR', NHR', or $CO_2R'$, and wherein one or more of the non-adjacent $CH_2$ groups are optionally independently replaced by —O—, —CO—, —CO—O—, —O—CO—, —NR'—, —NR'—CO—, —CO—NR',
$S_1, S_2$ are independently of each other a single bond or a spacer which is a straight-chain or branched C(1-12) alkyl, which is unsubstituted or substituted by at least one CN, Hal, OR', NHR', $CO_2R'$, SH, $SO_3H$ or $NO_2$, and wherein one or more of the non-adjacent $CH_2$ groups are optionally independently replaced by —O—, —CO—, —CO—O—, —O—CO—, —NR'—, —NR'—CO—, —CO—NR'—, —NR'—CO—O—, —O—CO—NR'—, —NR'—CO—NR'—, —CH=CH—, —C≡C—, —O—CO—O—, —S—R'—, or —$SO_3R'$—,
$D_1$ is H, halogen, C(1-12)alkyl, C(2-12)alkenyl, C(2-12) alkynyl, —$OR_{5^*}$, —$COR_{5^*}$, —$COOR_{5^*}$, —$NHR_{5^*}$, or —$CONHR_{5^*}$,
$R_{5^*}$ represents H, C(1-12)alkyl, C(2-12)alkenyl, or C(2-12)alkynyl,
$D_2$ is an acidic group,
$L_{3'}$ is straight-chain or branched C(1-8)alkyl, which is unsubstituted or substituted by at least one Hal, OR', NHR', or $CO_2R'$, and wherein one or more of the non-adjacent $CH_2$ groups are optionally independently replaced by —O—, —CO—, —CO—O—, —NR'—, —NR'—CO—,
p, q are independently of each other 0, 1, 2, 3, 4, 5 or 6,
k is 0 or 1,
r has a value of 1 to 7.

28. The compound according to claim 27, wherein
$X_1$ to $X_5$ are independently of each other N or O,
$M_1$ is a chelated metal radionuclide which is DTPA, DOTA, DO3A, HP-DO3A, EDTA, TETA, NOTA, or DOTMA complexed with a metal radionuclide ion, and
$M_2$ is a gamma- or positron-emitting non-metal radionuclide, which is $^{11}C$, $^{13}N$, $^{15}O$, $^{17}F$, $^{18}F$, $^{75}Br$, $^{76}Br$, $^{77}Br$, $^{123}I$, $^{124}I$, or $^{131}I$, optionally in combination with a prosthetic group.

29. The compound according to claim 1 having formulae VIII a-e

VIIIa

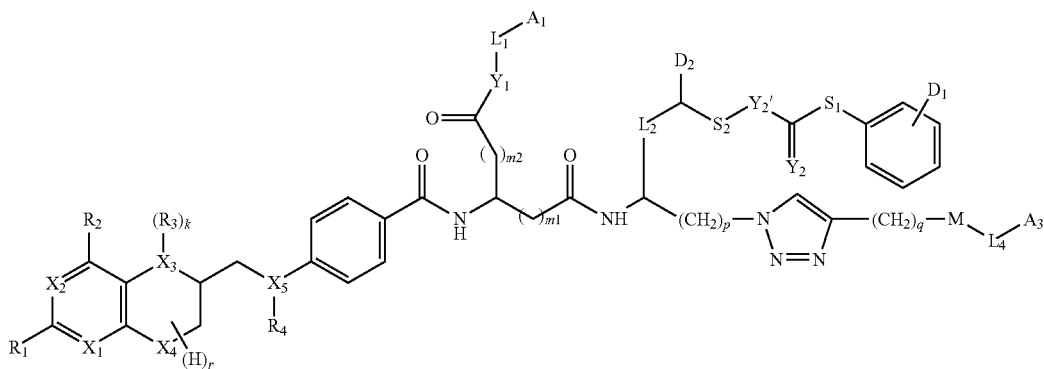

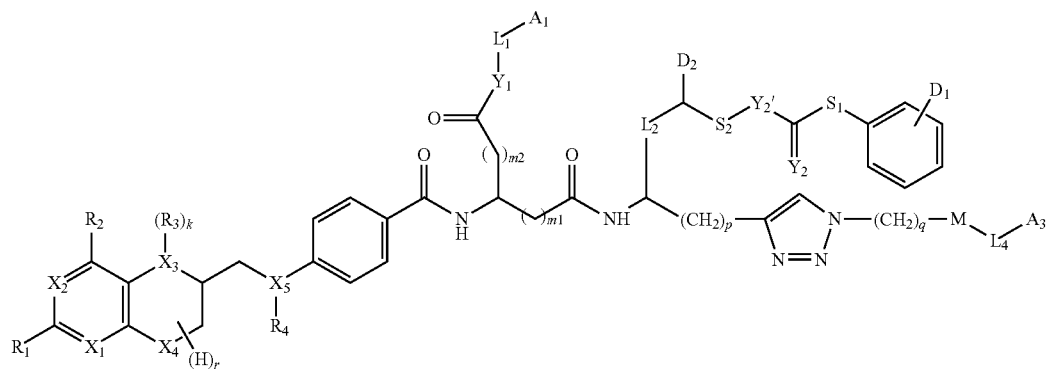
VIIIb
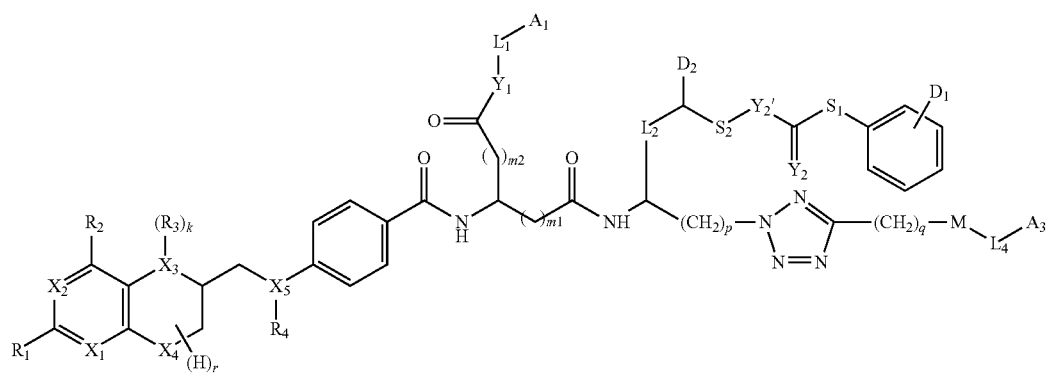
VIIIc
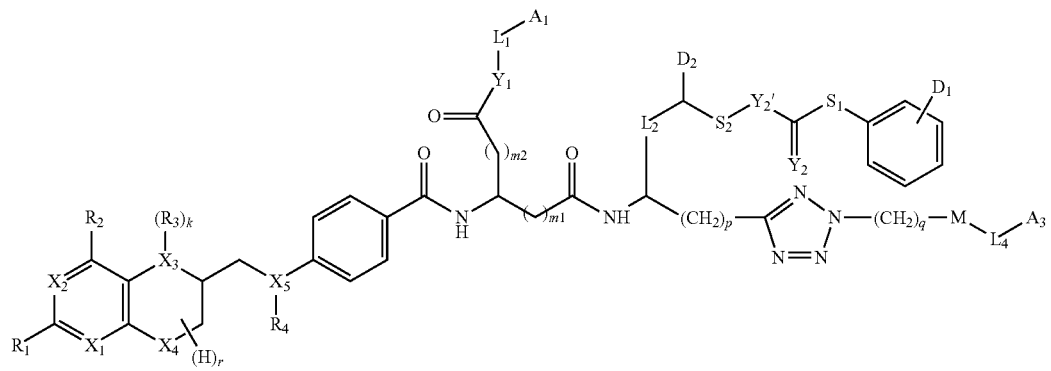
VIIId
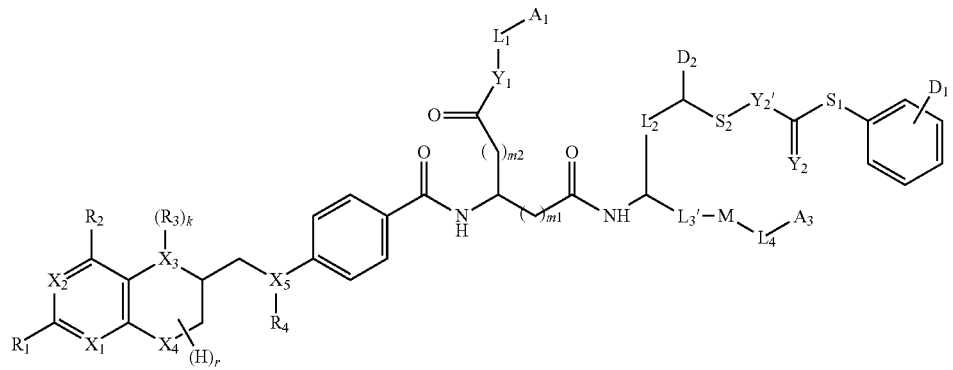
VIIIe wherein

X₁ to X₅ are independently of each other C, N or O,

Y₁, Y₂, Y₂' are independently of each other N, O or S,

R₁, R₂ are independently of each other H, halogen, C(1-12)alkyl, C(2-12)alkenyl, C(2-12)alkynyl, —OR₅, —COR₅, —COOR₅, —NHR₅, —CONHR₅, R₅ represents H, halo, C(1-12)alkyl, C(2-12)alkenyl, C(2-12)alkynyl, —OR', —COR', —COOR', or —NHR', R' is H or C(1-8)alkyl, R₃, R₄ are independently of each other H, nitroso, C(1-12)alkyl, —OR', —COR' or halosubstituted —COR', A₁ is H or a capping group, A₃ is H or a capping group, M is an imaging moiety M₁ or M₂, M₁ is a chelated metal radionuclide which is a linear or macrocyclic polyaminocarboxylate complexed with a radioimaging metal ion, M₂ is a gamma- or positron-emitting non-metal radionuclide optionally in combination with a prosthetic group, m₁, m₂ are independently of each other 0, 1, 2 or 3, L₁, L₄ are independently of each other a covalent bond or a straight-chain or branched C(1-8)alkyl, which is unsubstituted or substituted by at least one CN, Hal, OR', NHR', CO₂R' or NO₂, L₂ is a covalent bond or a linking group, which is straight-chain or branched C(1-8)alkyl, which is unsubstituted or substituted by at least one OR', NHR', or CO₂R', and wherein one or more of the non-adjacent CH₂ groups are optionally independently replaced by —O—, —CO—, —CO—O—, —O—CO—, —NR'—, —NR'—CO—, or —CO—NR', S₁, S₂ are independently of each other a single bond or a spacer which is a straight-chain or branched C(1-12)alkyl, which is unsubstituted or substituted by at least one CN, Hal, OR', NHR', CO₂R', SH, SO₃H or NO₂, and wherein one or more of the non-adjacent CH₂ groups are optionally independently replaced by —O—, —CO—, —CO—O—, —O—CO—, —NR'—, —NR'—CO—, —CO—NR'—, —NR'—CO—O—, —O—CO—NR'—, —NR'—CO—NR'—, —CH═CH—, —C≡C—, —O—CO—O—, —S—R'—, or —SO₃R'—, D₁ is H, halogen, C(1-12)alkyl, C(2-12)alkenyl, C(2-12)alkynyl, —OR₅*, —COR₅*, —COOR₅*, —NHR₅*, or —CONHR₅*, R₅* represents H, C(1-12)alkyl, C(2-12)alkenyl, or C(2-12)alkynyl, D₂ is an acidic group, L₃' is straight-chain or branched C(1-8)alkyl, which is unsubstituted or substituted by at least one Hal, OR', NHR', or CO₂R', and wherein one or more of the non-adjacent CH₂ groups are optionally independently replaced by —O—, —CO—, —CO—O—, —NR'—, or —NR'—CO—, p, q are independently of each other 0, 1, 2, 3, 4, 5 or 6, k is 0 or 1, r has a value of 1 to 7.

30. The compound according to claim 29, wherein

X₁ to X₅ are independently of each other N or O,

M₁ is a chelated metal radionuclide which is DTPA, DOTA, DO3A, HP-DO3A, EDTA, TETA, NOTA, or DOTMA, complexed with a radioimaging metal ion, and M₂ is a gamma- or positron-emitting non-metal radionuclide which is ¹¹C, ¹³N, ¹⁵O, ¹⁷F, ¹⁸F, ⁷⁵Br, ⁷⁶Br, ⁷⁷Br, ¹²³I, ¹²⁴I or ¹³¹I, optionally in combination with a prosthetic group.

31. A pharmaceutical composition comprising at least one compound according to claim 1 and one or more pharmaceutically acceptable carriers.

32. A method for diagnostic imaging of a cell or population of cells expressing a folate-receptor, said method comprising administering at least one compound according to claim 1 in a diagnostic imaging amount, performing diagnostic imaging by PET, detcecting a signal from said at least one compound, and obtaining a diagnostic image of said cell or population of cells.

33. The method according to claim 32, wherein the diagnostic imaging is performed of a cell or population of cells expressing a folate-receptor in vitro.

34. The method according to claim 32, wherein the diagnostic imaging is performed of a cell or population of cells expressing a folate-receptor in vivo.

35. A method for in vitro detection of a cell expressing the folate receptor in a tissue sample which includes contacting said tissue sample with a compound according to claim 1 in effective amounts and for sufficient time and conditions to allow binding to occur and detecting such binding by PET imaging.

36. A method of diagnostic imaging or monitoring a subject comprising administering at least one compound according to claim 1 in a diagnostic imaging amount, and performing diagnostic imaging by PET, and detecting a signal from said at least one compound.

37. The compound according to claim 1, wherein only one of A₁, A₂ and A₃ is an albumin binders.

38. The compound according to claim 1, wherein the albumin binder is a compound of formula III

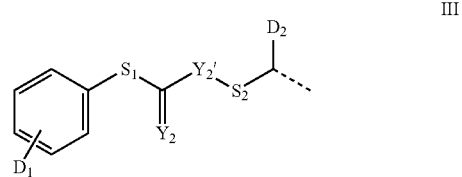

wherein

Y₂, Y₂' are independently of each other N, 0 or S, S₁, S₂ are independently of each other a single bond or a spacer which is a straight-chain or branched C(1-12)alkyl, which is unsubstituted or substituted by at least one CN, Hal, OR', NHR', CO₂R', SH, SO₃H or NO₂, and wherein one or more of the non-adjacent CH₂ groups are optionally independently replaced by —O—, —CO—, —CO—O—, —O—CO—, —NR'—, —NR'—CO—, —CO—NR'—, —NR'—CO—O—, —O—CO—NR'—, —NR'—CO—NR'—, —CH═CH—, —C≡C—, —O—CO—O—, —S—R'—, or —SO₃R'—, R' represents H or C(1-8)alkyl, D₁ is H, halogen, C(1-12)alkyl, C(2-12)alkenyl, C(2-12)alkynyl, —OR₅, —COR₅, —COOR₅, —NHR₅, —CONHR₅, R₅ represents H, C(1-12)alkyl, C(2-12)alkenyl, or C(2-12)alkynyl, and D₂ is an acidic group, and the broken line represents the linkage to L₁, L₂ or L₄.

39. The compound according to claim 38, wherein S₁ and S₂ are independently of each other a single bond or a spacer which is a straight-chain or branched C(1-8)alkyl, wherein one or more of the non-adjacent CH₂ groups are optionally independently replaced by —O—, —CO—, —COO—, —NR'—NR'—CO—, —CO—NR'—, —CH═CH—, wherein R' represents H or C(1-8)alkyl.

40. The compound according to claim 38, wherein Y₂ is O and/or Y₂' is N.

* * * * *